(12) United States Patent
Muramatsu et al.

(10) Patent No.: US 11,097,544 B2
(45) Date of Patent: Aug. 24, 2021

(54) LIQUID DISCHARGING HEAD AND LIQUID DISCHARGING APPARATUS

(71) Applicants: Koichi Muramatsu, Kanagawa (JP); Takahiko Matsumoto, Kanagawa (JP); Shinnosuke Koshizuka, Kanagawa (JP); Satoshi Okano, Kanagawa (JP); Satoshi Nakazawa, Kanagawa (JP); Yuzuru Kuramochi, Kanagawa (JP); Ryuya Mashiko, Tokyo (JP); Takeshi Akai, Kanagawa (JP); Daisuke Takagi, Kanagawa (JP); Tomoaki Nakayama, Tokyo (JP); Hidekazu Yaginuma, Kanagawa (JP); Hiroshi Fujie, Kanagawa (JP); Manabu Yamanaka, Kanagawa (JP)

(72) Inventors: Koichi Muramatsu, Kanagawa (JP); Takahiko Matsumoto, Kanagawa (JP); Shinnosuke Koshizuka, Kanagawa (JP); Satoshi Okano, Kanagawa (JP); Satoshi Nakazawa, Kanagawa (JP); Yuzuru Kuramochi, Kanagawa (JP); Ryuya Mashiko, Tokyo (JP); Takeshi Akai, Kanagawa (JP); Daisuke Takagi, Kanagawa (JP); Tomoaki Nakayama, Tokyo (JP); Hidekazu Yaginuma, Kanagawa (JP); Hiroshi Fujie, Kanagawa (JP); Manabu Yamanaka, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/672,572

(22) Filed: Nov. 4, 2019

(65) Prior Publication Data
US 2020/0139704 A1      May 7, 2020

(30) Foreign Application Priority Data

Nov. 5, 2018    (JP) .............................. JP2018-208204
Nov. 30, 2018   (JP) .............................. JP2018-225878
Jul. 31, 2019   (JP) .............................. JP2019-141773

(51) Int. Cl.
*B41J 2/14*          (2006.01)

(52) U.S. Cl.
CPC .................................. *B41J 2/1433* (2013.01)

(58) Field of Classification Search
CPC ............ B41J 2/1433; B41J 2002/14362; B41J 2002/1437; B41J 2/14298; B41J 2202/15;
(Continued)

(56) References Cited

U.S. PATENT DOCUMENTS

| 4,167,742 A | 9/1979 | Head et al. |
| 5,746,373 A | 5/1998 | Sanada |

(Continued)

FOREIGN PATENT DOCUMENTS

| DE | 29 05 063 A1 | 8/1980 |
| EP | 0 510 648 A2 | 10/1992 |

(Continued)

OTHER PUBLICATIONS

IP.com search (Year: 2020).*
Extended European Search Report dated Mar. 16, 2020, in Patent Application No. 19206871.6, 12 pages.

*Primary Examiner* — Lisa Solomon
(74) *Attorney, Agent, or Firm* — Oblon, McClelland, Maier & Neustadt, L.L.P.

(57) ABSTRACT

Provided is a liquid discharging head including: a membranous member including a discharging port through which a liquid is discharged; and a displacement member disposed at membranous member's one side at which the liquid to be discharged through the discharging port is provided and (Continued)

configured to displace a position of the membranous member to cause the liquid to be discharged through the discharging port.

18 Claims, 38 Drawing Sheets

(58) Field of Classification Search
CPC .............. B41J 2/14048; B05B 17/0676; B05B 17/0646; B05B 17/0607; B05B 15/20; B01L 2200/0647; B01L 2200/027; B01L 2300/0645; B01L 3/0268; C12M 33/00
See application file for complete search history.

(56) References Cited

U.S. PATENT DOCUMENTS

| | | | |
|---|---|---|---|
| 5,828,394 | A | 10/1998 | Khuri-Yakub et al. |
| 2005/0212863 | A1 | 9/2005 | Sanada |
| 2007/0051827 | A1 | 3/2007 | Shen et al. |
| 2014/0110500 | A1 | 4/2014 | Crichton et al. |
| 2016/0175834 | A1 | 6/2016 | Seo et al. |
| 2016/0176191 | A1 | 6/2016 | Kuramochi et al. |
| 2017/0120604 | A1 | 5/2017 | Seo et al. |
| 2017/0128971 | A1 | 5/2017 | Paunescu et al. |
| 2018/0169650 | A1 | 6/2018 | Somada et al. |
| 2018/0340880 | A1 | 11/2018 | Matsumoto et al. |
| 2019/0232661 | A1 | 8/2019 | Akai et al. |
| 2019/0283402 | A1 | 9/2019 | Kuramochi et al. |

FOREIGN PATENT DOCUMENTS

| | | |
|---|---|---|
| EP | 1 424 199 A1 | 6/2004 |
| EP | 2 058 129 A1 | 5/2009 |
| JP | H07-314665 | 12/1995 |
| JP | 2009-113255 | 5/2009 |
| JP | 2010-017856 | 1/2010 |
| JP | 2010-164502 | 7/2010 |
| JP | 5706610 | 3/2015 |
| JP | 2016-116489 | 6/2016 |
| JP | 2016-123309 | 7/2016 |
| JP | 2016-203157 | 12/2016 |
| JP | 2017-070247 | 4/2017 |
| JP | 2017-077197 | 4/2017 |
| JP | 2017-083439 | 5/2017 |
| JP | 2017-228643 | 12/2017 |
| JP | 2018-148817 | 9/2018 |
| JP | 2019-155269 | 9/2019 |
| WO | WO 93/01404 A1 | 1/1993 |
| WO | WO1997/012689 A1 | 4/1997 |

* cited by examiner

US 11,097,544 B2

LIQUID DISCHARGING HEAD AND LIQUID DISCHARGING APPARATUS

CROSS-REFERENCE TO RELATED APPLICATIONS

The present application claims priority under 35 U.S.C. § 119 to Japanese Patent Application No. 2018-208204 filed Nov. 5, 2018, Japanese Patent Application No. 2018-225878 filed Nov. 30, 2018, and Japanese Patent Application No. 2019-141773 filed Jul. 31, 2019. The contents of which are incorporated herein by reference in their entirety.

BACKGROUND OF THE INVENTION

Field of the Invention

The present disclosure relates to a liquid discharging head and a liquid discharging apparatus.

Description of the Related Art

In recent years, techniques for forming cell chips and three-dimensional tissues by discharging cell solutions containing cells from inkjet heads have been being developed actively.

Examples of mechanisms of inkjet heads include a piezoelectrically pressurizing mechanism using a piezoelectric element, a thermal mechanism using a heater, and an electrostatic mechanism configured to draw a liquid with an electrostatic attractive force. Among these mechanisms, piezoelectrically pressurizing-type inkjet heads can be used suitably for discharging liquid droplets of cell solutions, because these inkjet heads hardly give the cells damages due to heat and electric field.

However, common piezoelectrically pressurizing-type inkjet heads are configured to form liquid droplets by utilizing compression of the liquid in a pressurizing liquid chamber. Therefore, when bubbles are mixed in the pressurizing liquid chamber, these piezoelectrically pressurizing-type inkjet heads may not be able to discharge liquid droplets because bubbles may make the liquid hard to compress.

Further, surfactants used in common inkjet inks may give damages to cells, and may not be used in cell solutions. Therefore, water is often used as the solvent of the cell solutions. However, when water is used as the solvent, bubbles are likely to be mixed because water has a high surface tension.

Furthermore, when particle-suspending liquids such as cell solutions are discharged from inkjet heads, the number of particles contained in liquid droplets discharged may greatly vary due to, for example, sedimentation of the particles.

In order to overcome these problems, there has been proposed a liquid droplet forming device provided with an atmospherically exposed portion for exposing the interior of a liquid retaining unit to the atmosphere and configured to form liquid droplets by vibrating a membranous member in which a nozzle portion is formed (for example, see Japanese Unexamined Patent Application Publication No. 2016-116489).

SUMMARY OF THE INVENTION

According to one aspect of the present disclosure, a liquid discharging head includes a membranous member including a discharging port through which a liquid is discharged, and a displacement member disposed at membranous member's one side at which the liquid to be discharged through the discharging port is provided and configured to displace a position of the membranous member to cause the liquid to be discharged through the discharging port.

According to another aspect of the present disclosure, a liquid discharging head includes a membranous member including a discharging port through which a liquid is discharged, and a displacement member coupled to at least a part of a perimeter of the membranous member and configured to displace a position of the membranous member to cause the liquid to be discharged through the discharging port. The membranous member does not deform by being displaced by the displacement member.

According to another aspect of the present disclosure, a liquid discharging head includes a membranous member including a discharging port through which a liquid is discharged, a displacement member configured to displace a position of the membranous member to cause the liquid to be discharged through the discharging port, and a coupling member configured to couple the membranous member and the displacement member to each other in a manner that the membranous member is mountable and demountable.

According to another aspect of the present disclosure, a liquid discharging head includes a liquid retaining unit including a discharging port through which a liquid is discharged, and a displacement member configured to displace a position of the liquid retaining unit to cause the liquid to be discharged through the discharging port.

Figure 1A:
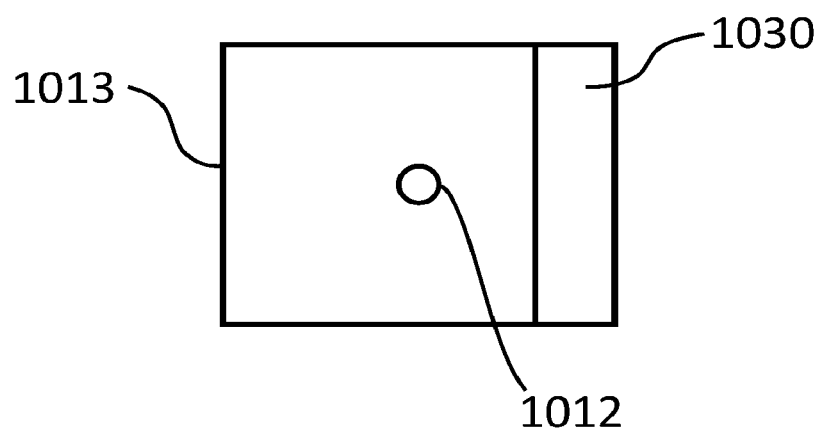
FIG. 1A is a schematic top view of an example liquid discharging head according to a first embodiment.

DESCRIPTION OF THE EMBODIMENTS (Liquid Discharging Head)

According to one aspect, a liquid discharging head (liquid discharging unit) of the present disclosure includes a membranous member including a discharging port through which a liquid is discharged, and a displacement member disposed at membranous member's one side at which the liquid to be discharged through the discharging port is provided and configured to displace a position of the membranous member to cause the liquid to be discharged through the discharging port. The liquid discharging head preferably further includes a securing member, a liquid containing chamber, an electrode, a cover, and a coupling member, and includes other members as needed.

According to another aspect, the liquid discharging head of the present disclosure includes a membranous member including a discharging port through which a liquid is discharged, and a displacement member coupled to at least a part of a perimeter of the membranous member and configured to displace a position of the membranous member to cause the liquid to be discharged through the discharging port. The membranous member does not deform while the displacement member is displacing the position of the membranous member. The liquid discharging head preferably further includes a securing member, a liquid containing chamber, an electrode, and a cover, and includes other members as needed.

According to another aspect, the liquid discharging head of the present disclosure includes a membranous member including a discharging port through which a liquid is discharged, a displacement member configured to displace the position of the membranous member to cause the liquid to be discharged through the discharging port, and a coupling member configured to couple the membranous member and the displacement member to each other in a manner that the membranous member is mountable and demountable. The liquid discharging head preferably further includes a securing member, a liquid containing chamber, an electrode, and a cover, and includes other members as needed.

In addition, according to another aspect, the liquid discharging head of the present disclosure includes a liquid retaining unit including a discharging port through which a liquid is discharged, and a displacement member disposed at a side of the liquid retaining unit opposite to a liquid discharging side through the discharging port and configured to displace a position of the liquid retaining unit to cause the liquid to be discharged through the discharging port. The liquid discharging head preferably further includes a securing member, an electrode, a cover, and a coupling member, and includes other members as needed.

The liquid discharging head of the present disclosure is based on a finding that existing liquid discharging heads cannot be reduced in size because the existing liquid discharging heads have complicated structures and may not also be able to have a sufficient maintenance convenience.

Existing liquid discharging heads as disclosed in Japanese Unexamined Patent Application Publication No. 2016-116489 are configured to form liquid droplets by vibrating a membranous member (nozzle plate) in which a nozzle portion is formed. Specifically, the existing liquid discharging heads are configured to largely vibrate (deform) a portion near a nozzle portion (discharging port) of the membranous member by means of, for example, a piezoelectric element installed on the membranous member, to form and discharge a liquid droplet. More specifically, in the existing liquid discharging heads, for example, the discharging port is displaced along with deformation of the membranous member, to induce an increase in the pressure in the liquid to be discharged, to cause a liquid droplet to be discharged through the discharging port. Therefore, in the existing liquid discharging heads, the membranous member needs to have some length in order to enable the discharging port to be deformed, making it difficult to simplify the structure and reduce the size. Moreover, in order for the discharging port to be deformed, it has been hard to apply a membranous member having a high stiffness. Hence, there has been a problem that the size and thickness of the membranous member are limited.

Further, the structures of the existing liquid discharging heads as disclosed in Japanese Unexamined Patent Application Publication No. 2016-116489 cannot be simplified because a ring-shaped piezoelectric element is disposed on the perimeter of the membranous member at the lower surface of the membranous member, so there have been cases where it is difficult to maintain (clean) the discharging port disposed in the center of the membranous member. Furthermore, there has been a problem that discharging stability degradation such as unstable discharging directions or discharging failures occurs, if stains are kept adhering to the discharging port.

Hence, the present inventors have conducted earnest studies into, for example, a liquid discharging head having a simple structure that can overcome the problems described above, and conceived the present disclosure. That is, the present inventors have found that liquid discharging heads according to some aspects described below can discharge a liquid with a simple structure.

Here, in one aspect of the liquid discharging head of the present disclosure, the liquid discharging head includes a membranous member including a discharging port through which a liquid is discharged, and a displacement member disposed at membranous member's one side at which the liquid to be discharged through the discharging port is provided and configured to displace a position of the membranous member to cause the liquid to be discharged through the discharging port. In the following description, the aspect including the membranous member including a discharging port through which a liquid is discharged, and the displacement member disposed at membranous member's one side at which the liquid to be discharged through the discharging port is provided and configured to displace a position of the membranous member to cause the liquid to be discharged through the discharging port may be referred to as "first aspect".

In the first aspect, because the displacement member is disposed at a side at which the liquid to be discharged through the discharging port is provided on the membranous member in which the discharging port is formed is disposed at the lower side of the liquid discharging head. Therefore, there is no need for disposing any other member such as the displacement member at a liquid discharging side of the membranous member (i.e., the lower surface side of the membranous member), making it possible to simplify the structure and facilitate maintenance (cleaning) of the portion near the discharging port at the lower surface side of the flat membranous member, providing an excellent maintenance convenience.

Further, in the first aspect, because the displacement member is configured to displace a position of the membranous member to cause the liquid to be discharged through the discharging port, there is no need for largely vibrating (deforming) a portion near the discharging port of the membranous member unlike in the existing liquid discharging head described above, and it is possible to cause the liquid to be discharged, by, for example, displacing the position of the whole membranous member. Furthermore, in the first aspect, for example, displacement is performed at the position of the edge portion (circumferential portion) of the membranous member unlike in the existing liquid discharging heads. That is, in the first aspect, for example, along with the position of the membranous member being displaced, the discharging port is displaced, to induce an increase in the pressure in the liquid to be discharged, to cause a liquid droplet to be discharged through the discharging port. Therefore, in the first aspect, it is not indispensable to deform the membranous member, making it possible to simplify the structure and use a smaller (shorter) membranous member than hitherto used. Hence, in the first aspect, the liquid discharging head can be reduced in size as compared with existing liquid discharging heads.

Next, in another aspect of the liquid discharging head of the present disclosure, the liquid discharging head includes a membranous member including a discharging port through which a liquid is discharged, and a displacement member coupled to at least a part of a perimeter of the membranous member and configured to displace a position of the membranous member to cause the liquid to be discharged through the discharging port, wherein the membranous member does not deform while the displacement member is displacing the position of the membranous member. In the following description, the aspect including a membranous member including a discharging port through which a liquid is discharged, and a displacement member coupled to at least a part of a perimeter of the membranous member and configured to displace a position of the membranous member to cause the liquid to be discharged through the discharging port, wherein the membranous member does not deform while the displacement member is displacing the position of the membranous member, may be referred to as "second aspect".

In the second aspect, the membranous member does not deform while the displacement member is displacing the position of the membranous member. Therefore, it is possible to apply a membranous member having a high stiffness and appropriately select the size and thickness of the membranous member. This makes it possible to simplify the structure and use a smaller (shorter) membranous member than hitherto used. Hence, in the second aspect, the liquid discharging head can be reduced in size as compared with existing liquid discharging heads. Also in the second aspect as in the first aspect, for example, along with the position of the membranous member being displaced, the discharging port is displaced, to induce an increase in the pressure in the liquid to be discharged, to cause a liquid droplet to be discharged through the discharging port.

Further, in the second aspect, it is possible to apply a membranous member having a high stiffness. Therefore, durability of the membranous member when the liquid discharging head continuously performs liquid discharging can be improved, and the membranous member can be suppressed from being damaged when the liquid discharging side of the membranous member (i.e., the lower surface side of the membranous member) is cleaned with a cleaning device such as a brush. In other words, in the second aspect, applicability of a membranous member having a high stiffness enables a simple structure and a high durability, providing a better maintenance convenience than obtained with the existing liquid discharging heads.

Next, in another aspect of the liquid discharging head of the present disclosure, the liquid discharging head includes a membranous member including a discharging port through which a liquid is discharged, a displacement member configured to displace a position of the membranous member to cause the liquid to be discharged through the discharging port, and a coupling member configured to couple the membranous member and the displacement member to each other in a manner that the membranous member is mountable and demountable. In the following description, the aspect including the membranous member including a discharging port through which a liquid is discharged, the displacement member configured to displace a position of the membranous member to cause the liquid to be discharged through the discharging port, and the coupling member configured to couple the membranous member and the displacement member to each other in a manner that the membranous member is mountable and demountable may be referred to as "third aspect".

In the third aspect, because the displacement member is configured to displace the position of the membranous member to cause the liquid to be discharged through the discharging port as in the first aspect, it is not indispensable to deform the membranous member. This makes it possible to simplify the structure and use a smaller (shorter) membranous member than hitherto used. Hence, in the third aspect, the liquid discharging head can be reduced in size as compared with existing liquid discharging heads.

Further, in the third aspect, the coupling member is configured to couple the membranous member and the displacement member to each other in a manner that the membranous member is mountable and demountable. Hence, in the third aspect, because the membranous member is demountable, it is easy to demount only the membranous member when cleaning the liquid discharging head and clean the simple structure attributable to the membranous member. Further, because the membranous member is demountable, it is easy to replace the membranous member when, for example, changing liquids to be discharged (i.e., the membranous member is disposable). Therefore, in the third aspect, it is easy to replace the membranous member when, for example, the membranous member is damaged, making it possible to improve the maintenance convenience of the liquid discharging head. Furthermore, in the third aspect, when there is a need for more reliably suppressing contamination between liquids when changing liquids to be discharged, this need can be met by replacing the membranous member instead of cleaning the membranous member, making it possible to save the time needed for cleaning the membranous member, providing an excellent maintenance convenience.

Next, in another aspect of the liquid discharging head of the present disclosure, the liquid discharging head includes a liquid retaining unit including a discharging port through which a liquid is discharged, and a displacement member configured to displace a position of the liquid retaining unit to cause the liquid to be discharged through the discharging port. In the following description, the aspect including the liquid retaining unit including a discharging port through which a liquid is discharged and the displacement member configured to displace a position of the liquid retaining unit to cause the liquid to be discharged through the discharging port may be referred to as "fourth aspect".

In the fourth aspect, because the displacement member is configured to displace the position of the liquid retaining unit to cause the liquid to be discharged through the discharging port, it is not indispensable to provide a membranous member. This provides a greater latitude in the shape of the liquid retaining unit and makes it possible to simplify the structure and reduce the size of the liquid discharging head as compared with the existing liquid discharging heads described above. Further, in the fourth aspect, for example, along with the position of the liquid retaining unit being displaced, the discharging port is displaced, to induce an increase in the pressure in the liquid to be discharged, to cause a liquid droplet to be discharged through the discharging port. Therefore, even when the fourth aspect includes a membranous member, it is not indispensable to deform the membranous member. This makes it possible to simplify the structure and use a smaller (shorter) membranous member than hitherto used. Hence, in the fourth aspect, the liquid discharging head can be reduced in size as compared with existing liquid discharging heads.

Furthermore, in the fourth aspect, because the displacement member is configured to displace the position of the liquid retaining unit to cause the liquid to be discharged through the discharging port, there is no need for disposing the displacement member near the discharging port of the liquid retaining unit. This makes it possible to simplify the structure and facilitate maintenance (cleaning) of the portion near the discharging port at the lower surface side of the liquid retaining unit, providing an excellent maintenance convenience.

As described above, the liquid discharging head of the present disclosure according to any of the first to fourth aspects can discharge a liquid with a simple structure. Further, as described above, with any of the first to fourth aspects, for example, the liquid discharging head can be reduced in size and maintenance convenience can be improved.

Moreover, if it is possible to reduce the size of the liquid discharging head, it is possible to install many liquid discharging heads in one liquid discharging apparatus. Therefore, when forming a tissue by, for example, discharging a cell solution (cell suspension), a liquid discharging apparatus including the liquid discharging head of the present disclosure can form a tissue formed of a plurality of cells in a shorter time. This makes it possible to suppress the cell survival rate from being lowered during formation.

As described above, the liquid discharging head of the present disclosure is configured to discharge a liquid by displacing the position of the membranous member or the liquid retaining unit. Therefore, when the liquid discharging head of the present disclosure includes a liquid containing chamber or a liquid retaining unit, the liquid discharging head can stir the liquid to be discharged, by displacing the position of the membranous member or the liquid retaining unit when discharging the liquid or by displacing the position of the membranous member or the liquid retaining unit so as not to exceed the limit beyond which the liquid is discharged.

The present disclosure has an object to provide a liquid discharging unit capable of discharging a liquid with a simple structure. The present disclosure can provide a liquid discharging head capable of discharging a liquid with a simple structure.

In the following description, the members according to the first to fourth aspects described above will be described.

[First Aspect]

In the first aspect of the present disclosure, the liquid discharging head includes a membranous member including a discharging port through which a liquid is discharged, and a displacement member disposed at membranous member's one side at which the liquid to be discharged through the discharging port is provided and configured to displace a position of the membranous member to cause the liquid to be discharged through the discharging port.

<Membranous Member>

The membranous member (film-shaped member) of the first aspect is not particularly limited and may be appropriately selected depending on the intended purpose so long as the membranous member includes a discharging port.

The shape of the membranous member is not particularly limited and may be appropriately selected depending on the intended purpose. For example, the shape of the membranous member may be a flat plate shape (film shape). The planar shape of the membranous member is not particularly limited and may be appropriately selected depending on the intended purpose. Examples of the planar shape of the membranous member include an approximately true-circular shape, an elliptic shape, and a polygonal shape. Among these shapes, the planar shape of the membranous member is preferably an approximately true-circular shape. The planar shape refers to the shape of the membranous member in a plan-view perspective.

The size of the membranous member is not particularly limited, may be appropriately selected depending on the intended purpose, and may be, for example, ϕ20 mm (diameter).

The average thickness of the membranous member is not particularly limited, may be appropriately selected depending on the intended purpose, and may be, for example, 0.05 mm.

The material of the membranous member is not particularly limited and may be appropriately selected depending on the intended purpose. Examples of the material of the membranous member include metals such as stainless steel, nickel, and aluminum, plastics (resin materials) such as ABS, polycarbonate, and fluororesins, and ceramics such as silicon dioxide, alumina, and zirconia.

The material of the membranous member is preferably a material having a hardness of a certain degree. When the material of the membranous member has a hardness of a certain degree, there is an advantage that the membranous member does not easily undergo vibration, and can easily stop vibration immediately when there is no need for discharging.

Examples of the material having a hardness of a certain degree include metals, ceramics, and resin (polymeric) materials. Further, among these materials, what is suitable to use is a material having a low adhesiveness with cells or proteins, when the liquid to be discharged contains particles and cells or proteins are used as the particles.

Adhesiveness of a material with cells is said to be dependent on the contact angle of the material with respect to water. When the material has a high hydrophilicity or a high hydrophobicity, the material tends to have a low adhesiveness with cells.

Examples of a material having a high hydrophilicity include metals and ceramics (metal oxides). Examples of a material having a high hydrophobicity include fluororesins.

Examples of metals include stainless steel, nickel, and aluminum. Examples of ceramics includes silicon oxide, alumina, and zirconia.

Further, it is preferable to reduce adhesiveness with cells by coating the surface of the material of the membranous member. Examples of coating over the surface of the material of the membranous member include coating the surface of the material with the metal or metal oxide materials described above, and coating the surface of the material with a synthetic phospholipid polymer mimicking a cellular membrane (e.g., LIPIDURE available from NOF Corporation).

The discharging surface of the membranous member is a surface of the membranous member at a liquid discharging side. For example, the discharging surface is the lower surface of the membranous member.

<<Discharging Port>>

The discharging port (nozzle) refers to a port (hole) through which a liquid provided on the membranous member is discharged. The discharging port is formed as, for example, a through hole that penetrates the membranous member from the upper surface to the lower surface.

The number of rows in which discharging ports are arranged, the manner of arranging discharging ports, the interval (pitch) between discharging ports, the shape of the openings of discharging ports, and the size of the openings of discharging ports are not particularly limited and may be appropriately selected depending on the intended purpose.

The shape of the openings of the discharging ports is not particularly limited, and examples of the shape include a circular (true-circular) shape, an elliptic shape, and a quadrangular shape.

The average diameter of the discharging ports is not particularly limited and may be appropriately selected depending on the intended purpose. When the liquid contains particles, the average diameter of the discharging ports is preferably two or more times greater than the size of the particles in order to avoid clogging the liquid discharging ports with the particles.

When the particles are, for example, animal cells, particularly, human cells, the average diameter of the discharging ports is preferably 10 micrometers or greater but 100 micrometers or less in conformity with the cells used, because human cells typically have a size of from 5 micrometers or greater but 50 micrometers or less.

On the other hand, in order to suppress a liquid droplet from becoming extremely large and facilitate formation of a minute liquid droplet, the average diameter of the discharging ports is preferably 200 micrometers or less. Hence, the average diameter of the discharging ports is more preferably 10 micrometers or greater but 200 micrometers or less.

The position of the discharging port in the membranous member is not particularly limited, may be appropriately selected depending on the intended purpose, and may be, for example, the center of the membranous member in a plan-view perspective, or may be any other position than the center of the membranous member in a plan-view perspective.

<<<Liquid>>>

The liquid to be discharged through the discharging port is not particularly limited and may be appropriately selected depending on the intended purpose. Examples of the liquid include various organic solvents such as ion-exchanged water, distilled water, pure water, a saline, alcohols, mineral oils, and vegetable oils. It is preferable that the liquid to be discharged through the discharging port contain particles.

When water is used as the liquid to be discharged through the discharging port, it is preferable that the liquid contain, for example, a humectant for suppressing evaporation of the water content. For such a prescription, common materials used in inkjet inks can be used.

It is preferable that the liquid to be discharged through the discharging port be discharged through the discharging port in the form of a liquid droplet.

The number of particles contained in a liquid droplet is preferably one or more and more preferably one or more but five or less.

The diameter of a liquid droplet is not particularly limited, may be appropriately selected depending on the intended purpose, and is preferably 25 micrometers or greater but 150 micrometers or less. When the diameter of a liquid droplet is 25 micrometers or greater, the diameter of a particle to be encapsulated in the liquid droplet is adequate, and many kinds of particles can be used. Further, when the diameter of a liquid droplet is 150 micrometers or less, discharging of a liquid droplet is stable.

When the diameter of a liquid droplet is assumed to be R and the diameter of a particle is assumed to be r, it is preferable that a relationship R>3r be satisfied. When the relationship R>3r is satisfied, the relationship between the diameter of a particle and the diameter of a liquid droplet is adequate, and the particle is not affected by the rim of the liquid droplet. This makes it possible to improve the accuracy of counting the number of particles, when the liquid discharging apparatus counts the number of particles contained in a liquid droplet.

The liquid volume of a liquid droplet is not particularly limited, may be appropriately selected depending on the intended purpose, and is preferably 1,000 pL or less and more preferably 100 pL or less.

The liquid volume of a liquid droplet can be measured by, for example, a method of obtaining the size of the liquid droplet from an image of the liquid droplet and calculating the liquid volume.

Examples of the particles to be contained in the liquid or a liquid droplet include cells, metal particles, and inorganic particles. Among these particles, cells are preferable.

—Cells—

Cells are not particularly limited and may be appropriately selected depending on the intended purpose. Examples of the cells include all kinds of cells, regardless of whether the cells are eukaryotic cells, prokaryotic cells, multicellular organism cells, and unicellular organism cells. One of these kinds of cells may be used alone or two or more of these kinds of cells may be used in combination.

The eukaryotic cells are not particularly limited and may be appropriately selected depending on the intended purpose. Examples of the eukaryotic cells include animal cells, insect cells, plant cells, fungi, algae, and protozoans. One of these kinds of eukaryotic cells may be used alone or two or more of these kinds of eukaryotic cells may be used in combination. Among these eukaryotic cells, animal cells and fungi are preferable, and cells derived from humans are more preferable.

Adherent cells may be primary cells directly taken from tissues or organs, or may be cells obtained by passaging primary cells directly taken from tissues or organs a few times. Adherent cells may be appropriately selected depending on the intended purpose. Examples of adherent cells include differentiated cells and undifferentiated cells.

Differentiated cells are not particularly limited and may be appropriately selected depending on the intended purpose. Examples of differentiated cells include: hepatocytes, which are parenchymal cells of a liver; stellate cells; Kupffer cells; endothelial cells such as vascular endothelial cells, sinusoidal endothelial cells, and corneal endothelial cells; fibroblasts; osteoblasts; osteoclasts; periodontal ligament-derived cells; epidermal cells such as epidermal keratinocytes; epithelial cells such as tracheal epithelial cells, intestinal epithelial cells, cervical epithelial cells, and corneal epithelial cells; mammary glandular cells; pericytes; muscle cells such as smooth muscle cells and myocardial cells; renal cells; pancreatic islet cells; nerve cells such as peripheral nerve cells and optic nerve cells; chondrocytes; and bone cells.

Undifferentiated cells are not particularly limited and may be appropriately selected depending on the intended purpose. Examples of undifferentiated cells include: pluripotent stem cells such as embryonic stem cells, which are undifferentiated cells, and mesenchymal stem cells having pluripotency; unipotent stem cells such as vascular endothelial progenitor cells having unipotency; and iPS cells.

Fungi are not particularly limited and may be appropriately selected depending on the intended purpose. Examples of fungi include molds and yeast fungi. One of these kinds of fungi may be used alone or two or more of these kinds of fungi may be used in combination. Among these kinds of fungi, yeast fungi are preferable because the cell cycles are adjustable and monoploids can be used.

The cell cycle means a cell proliferation process in which cells undergo cell division and cells (daughter cells) generated by the cell division become cells (mother cells) that undergo another cell division to generate new daughter cells.

Yeast fungi are not particularly limited, may be appropriately selected depending on the intended purpose, and are preferably Bar1-deficient yeasts with enhanced sensitivity to a pheromone (sex hormone) that controls the cell cycle at a G1 phase. When yeast fungi are Bar1-deficient yeasts, the abundance ratio of yeast fungi with uncontrolled cell cycles can be reduced. This makes it possible to, for example, prevent a specific nucleic acid from increasing in number in the cells contained in a liquid chamber.

The prokaryotic cells are not particularly limited and may be appropriately selected depending on the intended purpose. Examples of the prokaryotic cells include eubacteria and archaea. One of these kinds of prokaryotic cells may be used alone or two or more of these kinds of prokaryotic cells may be used in combination.

As the cells, living cells are preferable.

Further, as the cells, cells that can emit light upon reception of light are preferable. With cells that can emit light upon reception of light, it is possible to land the cells on a landing target while having a highly accurate control on the number of cells.

Reception of light means receiving of light.

An optical sensor means a passive sensor configured to collect, with a lens, any light in the range from visible light rays visible by human eyes to near infrared rays, short-wavelength infrared rays, and thermal infrared rays that have longer wavelengths than the visible light rays, to obtain, for example, shapes of target cells in the form of image data.

——Cells that can Emit Light Upon Reception of Light——

The cells that can emit light upon reception of light are not particularly limited and may be appropriately selected depending on the intended purpose so long as the cells can emit light upon reception of light. Examples of the cells include cells stained with a fluorescent dye, cells expressing a fluorescent protein, and cells labeled with a fluorescent-labeled antibody.

A cellular site stained with a fluorescent dye, expressing a fluorescent protein, or labeled with a fluorescent-labeled antibody is not particularly limited. Examples of the cellular site include a whole cell, a cell nucleus, and a cellular membrane.

——Fluorescent Dye——

Examples of the fluorescent dye include fluoresceins, azo dyes, rhodamines, coumarins, pyrenes, cyanines. One of these fluorescent dyes may be used alone or two or more of these fluorescent dyes may be used in combination. Among these fluorescent dyes, fluoresceins, azo dyes, and rhodamines are preferable, and eosin, Evans blue, trypan blue, rhodamine 6G, rhodamine B, and rhodamine 123 are more preferable.

As the fluorescent dye, a commercially available product may be used. Examples of the commercially available product include product name: EOSIN Y (available from Wako Pure Chemical Industries, Ltd.), product name: EVANS BLUE (available from Wako Pure Chemical Industries, Ltd.), product name: TRYPAN BLUE (available from Wako Pure Chemical Industries, Ltd.), product name: RHODAMINE 6G (available from Wako Pure Chemical Industries, Ltd.), product name: RHODAMINE B (available from Wako Pure Chemical Industries, Ltd.), and product name: RHODAMINE 123 (available from Wako Pure Chemical Industries, Ltd.).

——Fluorescent Protein——

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

——Fluorescent-Labeled Antibody——

The fluorescent-labeled antibody is not particularly limited and may be appropriately selected depending on the intended purpose so long as the fluorescent-labeled antibody is fluorescent-labeled. Examples of the fluorescent-labeled antibody include CD4-FITC and CD8-PE. One of these fluorescent-labeled antibodies may be used alone or two or more of these fluorescent-labeled antibodies may be used in combination.

It is preferable that the cells include a specific nucleic acid. The cell number of cells including the specific nucleic acid is not particularly limited and may be appropriately selected depending on the intended purpose, so long as the cell number is a plural number.

——Specific Nucleic Acid——

The specific nucleic acid is not particularly limited and may be appropriately selected depending on the intended purpose. Examples of the specific nucleic acid include base sequences used for infectious disease testing, naturally non-existent nucleic acids, animal cell-derived base sequences, and plant cell-derived base sequences. One of these nucleic acids may be used alone or two or more of these nucleic acids may be used in combination. As the specific nucleic acid, plasmids can also be suitably used.

The nucleic acid means a polymeric organic compound in which a nitrogen-containing base derived from purine or pyrimidine, sugar, and phosphoric acid are bonded with one another regularly.

The specific nucleic acid is not particularly limited and may be appropriately selected depending on the intended purpose. Examples of the specific nucleic acid include DNA and RNA. Of these, DNA corresponding to RNA derived from a region to which an infectious disease such as norovirus is immobilized, and naturally non-existent DNA can be suitably used.

The specific nucleic acid may be a specific nucleic acid derived from the cells to be used, or a specific nucleic acid introduced by transgenesis. When a specific nucleic acid introduced by transgenesis and a plasmid are used as the specific nucleic acid, it is preferable to confirm that one copy of the specific nucleic acid is introduced per cell. The method for confirming that one copy of the specific nucleic acid is introduced is not particularly limited and may be appropriately selected depending on the intended purpose. Examples of the method include a sequencer, a PCR method, and a Southern blotting method.

The method for transgenesis is not particularly limited and may be appropriately selected depending on the intended purpose so long as the method can introduce the specific nucleic acid sequences at an intended position by an intended number of molecules. Examples of the method include homologous recombination, CRISPR/Cas9, TALEN, Zinc finger nuclease, Flip-in, and Jump-in. In the case of yeast fungi, homologous recombination is preferable in terms of a high efficiency and ease of controlling.

—Metal Particles—

Metal particles are not particularly limited and may be appropriately selected depending on the intended purpose. Examples of the metal particles include silver particles and copper particles. The metal particles can be used for drawing wirings with liquid droplets discharged.

—Inorganic Particles—

Inorganic particles are not particularly limited and may be appropriately selected depending on the intended purpose. For example, titanium oxide and silicon oxide are used for purposes as white inks and purposes of coating spacer materials.

In event that aggregation of particles occurs, adjusting the concentration of particles in a liquid containing the particles enables an appropriate adjustment of the number of particles in the liquid, based on a theory that the concentration of particles in a liquid and the number of particles in the liquid conform to a Poisson distribution.

<Displacement Member>

The displacement member (displacement unit) according to the first aspect is disposed at membranous member's one side at which the liquid to be discharged through the discharging port is provided and configured to displace the position of the membranous member to cause the liquid to be discharged through the discharging port.

In the liquid discharging head according to the first aspect, the displacement member displaces the position of the membranous member to apply an inertial force to the liquid provided on the membranous member, and this enables the liquid provided on the membranous member to be discharged through the discharging port. That is, in the liquid discharging head according to the first aspect, for example, along with the position of the membranous member being displaced, the discharging port is displaced, to induce an increase in the pressure in the liquid to be discharged, to cause a liquid droplet to be discharged through the discharging port.

Further, the liquid discharging head may perform preparatory discharging for stabilizing discharging of the liquid, by letting the displacement member displace the position of the liquid container. Further, the liquid discharging head may stir the liquid contained in a liquid containing chamber described below by letting the displacement member displace the position of the membranous member.

When the liquid discharging head includes a coupling member described below, it is preferable that the displacement member displace the positions of the membranous member, the liquid containing chamber, and the coupling member together.

The direction in which the displacement member displaces the position of the membranous member is not particularly limited and may be appropriately selected depending on the intended purpose. When the liquid discharging head performs discharging of the liquid, it is preferable that the displacement member displace the position of the membranous member in the liquid discharging direction. It is preferable that the liquid discharging direction be approximately the gravity direction.

When the displacement member displaces the position of the membranous member, it is preferable that the displacement member reciprocate the membranous member (reciprocating movement), and more preferably vibrate the membranous member.

In the first aspect, it is preferable that the displacement member displace the position of the membranous member by reciprocating the membranous member in a direction approximately parallel with a direction in which the liquid is discharged through the discharging port. In this way, in the first aspect, it is possible to discharge the liquid more efficiently and discharge the liquid more truly to the desired position.

Here, in the case of displacing the position of the membranous member to cause the liquid to be discharged through the discharging port, the position of the whole membranous member may be displaced, or the membranous member may be deformed such that the position of the discharging port in the membranous member may be displaced. In other words, in the present disclosure, the displacement member may displace the position of the whole membranous member to cause the liquid to be discharged, or the displacement member may deform the membranous member such that the position of the discharging port in the membranous member may be displaced, to cause the liquid to be discharged.

The shape, size, material, and structure of the displacement member are not particularly limited and may be appropriately selected depending on the intended purpose.

As the displacement member, a piezoelectric element is suitably used.

The piezoelectric material is not particularly limited and may be appropriately selected depending on the intended purpose. Examples of the piezoelectric material include lead titanate zirconate (PZT), bismuth iron oxide, niobic acid metal, barium titanate, or materials obtained by adding metals or different oxides to these materials. Among these piezoelectric materials, lead titanate zirconate (PZT) is preferable because a high inverse piezoelectric effect can be obtained.

The vibration mode of the piezoelectric element is not particularly limited and may be appropriately selected depending on the intended purpose. Examples of the vibration mode include a longitudinal mode and a shear mode.

As a longitudinal mode piezoelectric element, for example, a laminated piezoelectric element configured to elongate in the longitudinal direction and contract in the lateral direction in response to application of a voltage can be used. As a shear mode piezoelectric element, for example, a bimorph-type (bend-type) piezoelectric element configured to deform and bend in response to application of a voltage to cause the position of one end of the piezoelectric element to be displaced may be used.

As the displacement member, a material having a different coefficient of linear expansion from the coefficient of linear expansion of the membranous member may be pasted over the membranous member and heated, in order to displace the position of the discharging port. In this case, a heater may be disposed near the material having the different coefficient of linear expansion, and the heater may be heated through electrification to displace the position of the discharging port.

In the first aspect, the position at which the displacement member is disposed is not particularly limited and may be appropriately selected depending on the intended purpose so long as the position is at membranous member's one side at which the liquid to be discharged through the discharging port is provided.

Further, in the first aspect, it is preferable that the displacement member contact the membranous member. By the displacement member contacting the membranous member, for example, it is possible to enable the liquid to be discharged by means of at least the membranous member and the displacement member. This makes it possible to more simplify the structure of the liquid discharging head.

The position at which the displacement member contacts the membranous member is not particularly limited and may be appropriately selected depending on the intended purpose so long as the position is a position at which it is possible for the liquid to be discharged in response to the position of the membranous member being displaced by the displacement member.

Further, in the first aspect, it is preferable that the displacement member be disposed in a manner to surround the perimeter of the membranous member to be capable of retaining the liquid to be provided on the membranous member. In this way, in the first aspect, the displacement member is capable of retaining the liquid to be discharged through the discharging port, making it possible to provide the liquid in a greater amount above the membranous member. Further, by the displacement member being capable of retaining the liquid, the liquid discharging head can retain the liquid by a predetermined thickness on the membranous member. This stabilizes the water pressure of the liquid above the membranous member when the liquid is to be discharged through the discharging port and enables more stable discharging of the liquid.

Here, as the perimeter of the membranous member, for example, the region about the external edge of the membranous member (external being distal from the discharging port) can be selected. By the displacement member being positioned in a manner to surround the perimeter of the membranous member, the liquid can be retained in a greater amount.

When the displacement member is positioned (disposed) in a manner to surround the perimeter of the membranous member, the planar shape of the displacement member may be, for example, an annular (ring-like) shape, or the same shape as the perimeter of the membranous member.

In the first aspect, it is preferable that at least part of the surface of the displacement member have a coating film to shield contact with the liquid. More specifically, for example, when part of the surface of the displacement member is in a positional relationship of having contact with the liquid to be discharged through the discharging port, it is preferable that a coating film for shielding contact with the liquid be provided at part of the displacement member having a possibility of contacting the liquid.

In this way, in the first aspect, for example, the displacement member can be prevented from having contact with the liquid. Hence, when a displacement member having no resistance to the liquid to be discharged through the discharging port is used, a greater protection is provided against troubles that may occur if the displacement member contacts the liquid.

Further, it is preferable that the coating film be of a material and a thickness that do not hinder the movement of the displacement member. For example, when the liquid to be discharged through the discharging port is a liquid mainly formed of water, the coating film may be one that has water resistance.

Here, the coating film is not particularly limited and may be appropriately selected depending on the intended purpose so long as the coating film can shield contact with the liquid to be discharged through the discharging port. Examples of the coating film include organic films such as parylene, epoxy, and melamine, and inorganic films.

The method for forming the coating film over the surface of the displacement member is not particularly limited and may be appropriately selected depending on the intended purpose. Examples of the method include spin coating, dipping, spray coating, vapor deposition, and CVD.

<<Electrodes>>

When a piezoelectric element is used as the displacement member, for example, it is preferable that the displacement member have a structure including electrodes across which a voltage is applied to the piezoelectric material. In this case, application of a voltage by a driving unit across the electrodes of the piezoelectric element makes the piezoelectric element vibrate, making it possible to vibrate the membranous member.

For example, it is preferable that the positions at which the electrodes across which a voltage is applied to the displacement member are provided be positions that do not contact the liquid to be discharged through the discharging port. Further, it is preferable that the positions at which the electrodes are provided be outside a liquid containing chamber, when the liquid discharging head include the liquid containing chamber described below. In other words, in the first aspect, when the liquid discharging head includes a liquid containing chamber, it is preferable that the electrodes across which a voltage is applied to the displacement member be provided outside the liquid containing chamber. In this way, the liquid discharging head can prevent the liquid to be discharged through the discharging port from contacting the electrodes and have a greater protection against troubles that may occur if the liquid to be discharged through the discharging port contacts the electrodes.

<Securing Member>

In the first aspect of the liquid discharging head of the present disclosure, it is preferable that the liquid discharging head include a securing member (securing unit) disposed at membranous member's one side at which the liquid is provided and configured to secure a side of the displacement member opposite to a side of the displacement member contacting the membranous member. By including the securing member, the liquid discharging head can be improved in the latitude in selection of the position at which the liquid discharging head is disposed. For example, this makes it easier to dispose a plurality of liquid discharging heads side by side.

Here, the shape, size, material, and structure of the securing member are not particularly limited and may be appropriately selected depending on the intended purpose so long as the securing member can secure the side of the displacement member opposite to the side of the displacement member contacting the membranous member.

In the first aspect, it is preferable that the securing member be formed of a material that has a high stiffness and does not easily deform. Examples of the material that can be applied as the securing member, and has a high stiffness and does not easily deform include metal materials such as stainless steel (SUS) and ceramic materials.

The securing member formed of the material that has a high stiffness and does not easily deform can suppress loss of displacing energy of the displacement member, making it possible to displace the position of the membranous member efficiently and cause the liquid to be discharged through the discharging port more efficiently.

<Liquid Containing Chamber>

In the first aspect of the liquid discharging head of the present disclosure, it is preferable that the liquid discharging head include a liquid containing chamber (liquid chamber, liquid container) that can contain the liquid to be provided on at least any one of the membranous member and the displacement member.

By including the liquid containing chamber, the liquid discharging head can contain the liquid to be discharged through the discharging port and have the liquid provided in a greater amount on the membranous member. Hence, the liquid discharging head can contain the liquid by a predetermined thickness above the membranous member and stabilize the water pressure of the liquid above the membranous member when the liquid is to be discharged through the discharging port, making it possible to more stably discharge the liquid. Further, by including the liquid containing chamber, the liquid discharging head can provide the liquid in a greater amount above the membranous member. This makes it possible to reduce the number of times of supplying the liquid into the liquid discharging head and discharge more liquid droplets in a shorter time. Particularly, when forming a tissue formed of a plurality of cells by discharging a cell solution (cell suspension) from the liquid discharging head, it is possible to form the tissue in a shorter time, making it possible to suppress the cell survival rate from being lowered during formation.

The shape, size, material, and structure of the liquid containing chamber are not particularly limited and may be appropriately selected depending on the intended purpose so long as the liquid containing chamber can contain the liquid to be provided on at least any one of the membranous member and the displacement member.

Here, for example, the liquid containing chamber may be a cylindrical member closely attached on the displacement member contacting the membranous member.

It is preferable that the liquid containing chamber be capable of letting a gas pass through at least part of the liquid containing chamber. The liquid containing chamber capable of letting a gas pass through at least part of the liquid containing chamber means that the liquid containing chamber can let a gas pass through between the inside and the outside of the liquid chamber of the liquid containing chamber.

The liquid containing chamber is not particularly limited and may be appropriately selected depending on the intended purpose. It is preferable that the liquid containing chamber further include a ventilation port, and more preferably further include at least any one of an opening and an adhesion preventing member.

Examples of the material of the liquid containing chamber include metals such as stainless steel, nickel, and aluminum, plastics (resin materials) such as ABS, polycarbonate, and fluororesins, and ceramics such as silicon dioxide, alumina, and zirconia. Among these materials, what is suitable to use is a material having a low adhesiveness with cells or proteins, when the liquid contained in the liquid containing chamber contains particles and cells or proteins are used as the particles.

Adhesiveness of a material with cells is said to be dependent on the contact angle of the material with respect to water. When the material has a high hydrophilicity or a high hydrophobicity, the material tends to have a low adhesiveness with cells. Examples of a material having a high hydrophilicity include various metals and ceramics (metal oxides). Examples of a material having a high hydrophobicity include fluororesins.

Further, it is preferable to reduce adhesiveness with cells by coating the surface of the material of the liquid chamber. Examples of coating over the surface of the material of the liquid chamber include coating the surface of the material with the metal or metal oxide materials described above, and coating the surface of the material with a synthetic phospholipid polymer mimicking a cellular membrane (e.g., LIPIDURE available from NOF Corporation).

<<Ventilation Port>>

The ventilation port (atmospherically exposed portion) means a port (hole) through which a gas can pass between the inside and the outside of the liquid containing chamber. With the ventilation port present in the liquid containing chamber, the atmospheric pressure inside the liquid containing chamber becomes approximately the same as the atmospheric pressure (typically, standard atmosphere) outside the liquid containing chamber. This makes it possible to discharge the liquid contained in the liquid containing chamber stably by suppressing the inside of the liquid containing chamber from being a negative pressure.

The ventilation port is not particularly limited and may be appropriately selected depending on the intended purpose so long as a gas can pass through the ventilation port between the inside and the outside of the liquid containing chamber.

The ventilation port may be, for example, a through hole penetrating the liquid containing chamber, or an opening for ventilation formed by partially opening the liquid containing chamber. The ventilation port may be covered with a member through which a gas can pass. Examples of the member through which a gas can pass include a meshed member and a spongy member.

With a gas enabled to pass between the inside and the outside of the liquid containing chamber, it is possible to prevent the inside of the liquid containing chamber from being a negative pressure when discharging the liquid, making it easier for the liquid to be discharged. Further, it is also possible to evacuate bubbles mixed in the liquid contained in the liquid containing chamber, making it possible for the liquid to be discharged stably.

Moreover, with a gas enabled to pass between the inside and the outside of the liquid containing chamber, when the liquid contained in the liquid containing chamber contains cells as particles, cells can be suppressed from being damaged by pressurization when the liquid is discharged. If it is possible to suppress cells from being damaged by pressurization when the liquid is discharged, there is an advantage that the cell survival rate can be suppressed from being lowered during, for example, formation of a tissue formed of a plurality of cells.

<<Opening>>

It is preferable that the liquid containing chamber include an opening.

The opening is not particularly limited and may be appropriately selected depending on the intended purpose. The opening is preferably an opening through which at least part of the liquid contained in the liquid containing chamber is exposed to the outside of the liquid containing chamber. The opening may be served by the ventilation port described above (i.e., the opening and the ventilation port are the same as each other), or may be provided separately from the ventilation port. When the opening is provided separately from the ventilation port described above, for example, the opening may be provided in the adhesion preventing member described below.

With the opening present in the liquid containing chamber, it is possible to operate the liquid contained in the liquid containing chamber without demounting the liquid containing chamber from a supporting member described below.

When it is possible to operate the liquid contained in the liquid containing chamber without demounting the liquid containing chamber from the supporting member described below, the time taken to operate the liquid can be reduced, making it possible to consequently improve the efficiency of discharging liquid droplets. When it is possible to improve the efficiency of discharging liquid droplets, there is an advantage that the cell survival rate can be suppressed from being lowered during, for example, formation of a tissue formed of a plurality of cells.

Examples of the operation of the liquid include replenishment of the liquid and stirring of the liquid, which can be performed with an operation tool. Examples of the operation tool include: pipettes such as a Komagome type pipette, a whole pipette, a measuring pipette, and a micropipette; a glass tube; and a glass rod.

It is preferable that the position at which the opening is provided be a position at which it is easy to insert the operation tool into the opening, and at which the operation of the operation tool is not limited by, for example, the coupling member described below and the displacement member.

<<Adhesion Preventing Member>>

It is preferable that the liquid containing chamber include an adhesion preventing member for preventing the liquid contained in the liquid containing chamber from adhering to the outside of the liquid containing chamber.

The adhesion preventing member is not particularly limited and may be appropriately selected depending on the intended purpose. For example, the adhesion preventing member may be a form of a cover covering at least part of the top of the liquid containing chamber (in a manner to allow a gas to pass through) or a form of a hood (canopy) partially opened.

With the adhesion preventing member provided on the liquid containing chamber, it is possible to prevent the liquid from being scattered to the outside of the liquid containing chamber in response to displacement (vibration) of the liquid containing chamber when discharging the liquid, and from adhering to any other members than the liquid containing chamber to constitute a factor of contamination.

Further, as described above, it is preferable that the opening be provided in the adhesion preventing member. With the opening provided in the adhesion preventing member, it is possible to prevent the liquid from being adhering to any other members than the adhesion preventing member and constituting a factor of contamination due to the operation tool coming into contact with such members when operating the liquid contained in the liquid containing chamber.

<<Cover>>

It is preferable that the liquid discharging head of the present disclosure include a cover disposed at the membranous member's one side at which the liquid is provided in a manner to face the membranous member. This makes it possible to reduce the amount by which the liquid contained in the liquid discharging head of the present disclosure is evaporated. Further, it is preferable that the cover include a ventilation port. Furthermore, the cover may be served by the adhesion preventing member.

The shape, size, material, and structure of the cover are not particularly limited and may be appropriately selected depending on the intended purpose.

It is preferable that the liquid discharging head of the present disclosure further include a stirring member attached on the cover and configured to stir the contained liquid by conveying the liquid. For example, when the liquid contains particles, this makes it possible for the liquid discharging head of the present disclosure to disperse the particles when the particles have precipitated in the contained liquid and the discharging port is likely to be clogged with the particles during discharging.

The stirring member (stirring unit) is not particularly limited and may be appropriately selected depending on the intended purpose so long as the stirring member can stir the liquid. Examples of the stirring member (stirring unit) include a stirring member including: a first liquid delivering unit; a second liquid delivering unit; a flow path linking the first liquid delivering unit to the liquid retaining unit; and a flow path linking the second liquid delivering unit to the liquid retaining unit. In this case, flow paths provided with water stop valves can be used as the flow paths. Here, it is preferable that the first liquid delivering unit and the second liquid delivering unit function as a pair of liquid conveying units, the flow path and the flow path function as a pair of liquid reservoirs, and the water stop valve and the water stop valve function as a pair of opening/closing units.

It is preferable that the liquid to be discharged through the discharging port be supplied into the liquid discharging head of the present disclosure by the stirring member. Hence, the liquid discharging head of the present disclosure can be quickly supplied with the liquid when the amount of the contained liquid is reduced through repeated discharging of the liquid.

<Coupling Member>

In the first aspect of the liquid discharging head of the present disclosure, it is preferable that the liquid discharging head include a coupling member (supporting member) configured to couple the liquid containing chamber and the displacement member to each other. In other words, it is preferable that the liquid discharging head of the present disclosure include the liquid containing chamber that can contain the liquid to be provided on at least any one of the membranous member and the displacement member, and the coupling member configured to couple the liquid containing chamber and the displacement member to each other. With the liquid discharging head provided with the coupling member, it is possible to better improve the latitude in selection of the shape and disposition of the liquid discharging head, and make it easier to dispose many liquid discharging heads side by side.

The shape, size, material, and structure of the coupling member are not particularly limited and may be appropriately selected depending on the intended purpose.

Examples of the material of the coupling member include metals such as stainless steel, nickel, and aluminum, plastics such as ABS, polycarbonate, and fluororesins, and ceramics such as silicon dioxide, alumina, and zirconia.

The method by which the coupling member couples (supports) the liquid containing chamber is not particularly limited and may be appropriately selected. Examples of the method include a method of supporting the liquid containing chamber in a manner that at least part of the ventilation port of the liquid containing chamber is opened, and a method of forming a ventilation port also in the coupling member and making the coupling member couple (support) the liquid containing chamber in a manner that a gas can circulate through the ventilation port of the liquid containing chamber and the ventilation port of the coupling member.

It is preferable that the coupling member couple (support) the liquid containing chamber in a manner that the liquid containing chamber is mountable and demountable. In other words, it is preferable that the coupling member include a demounting member configured to support (couple) the liquid containing chamber in a manner that the liquid containing chamber is mountable and demountable. With the coupling member coupling the liquid containing chamber in a manner that the liquid containing chamber is mountable and demountable, it is possible to perform replacement of the membranous member and the liquid containing chamber, making it possible to suppress contamination of liquids, when liquids to be discharged are changed.

When forming a cell chip or a three-dimensional tissue using the liquid discharging head or a liquid discharging apparatus, there is a case when it is needed to discharge a plurality of different kinds of liquids from one liquid discharging head. In such a case, in order to prevent contamination of different liquids, it is preferable to replace the liquid to be discharged together with the membranous member and the liquid containing chamber when changing the liquids to be discharged, and dispose of the membranous member and the liquid containing chamber.

Japanese Unexamined Patent Application Publication No. 2010-164502 describes, for example, a disposable liquid containing chamber. Because this technique forms a liquid droplet by utilizing compression of a liquid in a liquid chamber, the technique may not be able to compress the liquid and discharge a liquid droplet when bubbles are mixed in the pressurizing liquid chamber. Further, according to the technique described in Japanese Unexamined Patent Application Publication No. 2010-164502, a piezoelectric element may be broken because the piezoelectric element repeatedly collides with a displacement regulating plate via a pressure plate.

Further, according to an existing liquid discharging head (for example, the one described in Japanese Unexamined Patent Application Publication No. 2016-116489), a displacement member such as a piezoelectric element is provided in a liquid containing chamber (a liquid droplet forming device in Japanese Unexamined Patent Application Publication No. 2016-116489). Therefore, the existing liquid discharging head is not cost-effective, because the expensive displacement member is also thrown away when the membranous member and the liquid containing chamber are disposed of. Moreover, because a displacement member is provided in a liquid containing chamber in an existing liquid discharging head, there is a need for operations for detaching or attaching electrical wires for operating the displacement member and adjustment for suppressing operational variation from piezoelectric element to piezoelectric element when replacing (exchanging) membranous members and liquid containing chambers. Therefore, the existing liquid discharging head has a problem of difficulty replacing the membranous member and the liquid containing chamber in a short time.

In a preferable aspect of the liquid discharging head of the present disclosure, i.e., in an aspect in which the coupling member couples the liquid containing chamber in a manner that the liquid containing chamber is mountable and demountable, the displacement member displaces the position of the whole membranous member via the coupling member to cause the liquid to be discharged. Hence, the displacement member is not provided on the membranous member and the liquid containing chamber. Therefore, in this aspect, the coupling member that couples the liquid containing chamber in a manner that the liquid containing chamber is mountable and demountable enables replacement of the membranous member and the liquid containing chamber in a short time when replacement of the membranous member and the liquid containing chamber is needed.

Further, it is particularly advantageous to be capable of replacing the membranous member and the liquid containing chamber in a short time, because the cell survival rate can be suppressed from being lowered during, for example, formation of a tissue formed of a plurality of cells.

The demounting member is not particularly limited and may be appropriately selected depending on the intended purpose. Examples of the demounting member include a threaded coupling member such as a screw configured to support the liquid containing chamber in a biasing manner, an elastic body configured to support the liquid containing chamber in a biasing manner, and a magnetic body configured to support the liquid containing chamber with a magnetic force. One of these members may be used alone or two or more of these members may be used in combination. Among these members, the elastic body configured to support the liquid containing chamber in a biasing manner and the magnetic body configured to support the liquid containing chamber with a magnetic force are preferable as the demounting member.

It is preferable that the demounting member include an elastic body and that the elastic body bias the liquid containing chamber to support the liquid containing chamber in a non-detachable manner. With the demounting member including the elastic body and the elastic body biasing the liquid containing chamber to support the liquid containing chamber in a non-detachable manner, it is possible to replace the membranous member and the liquid containing chamber in a shorter time easily.

The elastic body is not particularly limited and may be appropriately selected depending on the intended purpose.

Examples of the elastic body include a rubber, a coil spring, a leaf spring, and a torsion bar. Among these elastic bodies, a leaf spring is preferable. One of these elastic bodies may be used alone or two or more of these elastic bodies may be used in combination.

The liquid containing chamber being supported in a non-detachable manner means that the liquid containing chamber can be mounted or demounted by, for example, a user when replacing the liquid containing chamber, but that the liquid containing chamber can be coupled (supported) by the coupling member when the liquid containing chamber and the coupling member are stationary and when the liquid containing chamber and the coupling member are displaced (vibrated) by the displacement member.

It is also preferable that the demounting member include a magnetic body and that the magnetic body support the liquid containing chamber in a non-detachable manner with a magnetic force. With the demounting member including the magnetic body and the magnetic body supporting the liquid containing chamber in a non-detachable manner with a magnetic force, it is possible to replace the membranous member and the liquid containing chamber in a shorter time easily.

The magnetic body means a body that generates a magnetic field. Examples of the magnetic body include a permanent magnet and an electromagnet. Of these magnetic bodies, a permanent magnet is preferable. One of these magnetic bodies may be used alone or two or more of these magnetic bodies may be used in combination.

When the demounting member includes a magnetic body, it is preferable that the liquid containing chamber include an adsorbing member configured to generate an attractive force with respect to the coupling member by means of the magnetic force generated by the magnetic body. The adsorbing member is not particularly limited and may be appropriately selected depending on the intended purpose. Examples of the adsorbing member include ferromagnetic metals such as iron, cobalt, and nickel. One of these adsorbing members may be used alone or two or more of these adsorbing members may be used in combination.

Further, in the first aspect of the liquid discharging head of the present disclosure, it is preferable that there be a plurality of membranous members and that the coupling member couple the membranous member in a manner that the membranous members can be disposed adjacently. Here, the coupling member coupling the membranous member in a manner that the membranous members can be disposed adjacently means that, for example, when a plurality of membranous members are disposed side by side to form a multichannel, the membranous members can be disposed closely adjacently with each other in a direction in which the membranous members are disposed side by side.

The method by which the coupling member couples the membranous member in a manner that the membranous members can be disposed adjacently is not particularly limited and may be appropriately selected depending on the intended purpose. Examples of the method include a method of making the diameter of the coupling member shorter than the diameters of the membranous member and liquid containing chamber in the direction in which the plurality of membranous members are disposed side by side.

With the coupling member coupling the membranous member in a manner that the membranous members can be disposed adjacently, it is possible to make the liquid discharging head smaller in size. This makes it possible to dispose the membranous members more closely when forming a multichannel by disposing a plurality of membranous members side by side, making it possible to install a greater number of liquid discharging heads in one liquid discharging apparatus. In this way, for example, when forming a tissue formed of a plurality of cells by discharging a cell solution (cell suspension), it is possible to form the tissue in a shorter time and suppress the cell survival rate from being lowered during formation.

<Other Members>

The other members are not particularly limited and may be appropriately selected depending on the intended purpose.

[Second Aspect]

In the second aspect of the present disclosure, a liquid discharging head includes a membranous member including a discharging port through which a liquid is discharged, and a displacement member coupled to at least a part of a perimeter of the membranous member and configured to displace a position of the membranous member to cause the liquid to be discharged through the discharging port, wherein the membranous member does not deform while the displacement member is displacing the position of the membranous member.

In the following description, the matters by which the second aspect is distinguished from the first aspect will be described. Hence, any matters of the second aspect not to be particularly described below may be the same as in the first aspect.

<Membranous Member>

As the membranous member of the second aspect, a membranous member that includes a discharging port through which a liquid is discharged as in the first aspect and further does not deform while the displacement member is displacing the position of the membranous member can be used.

Here, what is meant by that "the membranous member does not deform while the displacement member is displacing the position of the membranous member" is that the membranous member is not deformed by the displacement by the displacement member when the displacement member displaces the position of the membranous member in order to cause the liquid to be discharged through the discharging port. Further, what is meant by that the membranous member does not deform is that the membranous member does not substantially deform.

The material of the membranous member of the second aspect is not particularly limited and may be appropriately selected depending on the intended purpose so long as the material does not deform while the displacement member is displacing the position of the membranous member. Examples of the material of the membranous member include materials having a high stiffness (e.g., metal materials).

Because the membranous member of the second aspect is formed of, for example, a material having a high stiffness, the size and thickness of the membranous member can be appropriately selected, making it possible to simplify the structure and use a smaller (shorter) membranous member than hitherto used. Hence, in the second aspect, the liquid discharging head can be reduced in size as compared with existing liquid discharging heads.

Other respects of the membranous member of the second aspect may be the same as in the first aspect.

<Displacement Member>

The displacement member of the second aspect is coupled to at least a part of a perimeter of the membranous member and configured to displace a position of the membranous member to cause the liquid to be discharged through the discharging port.

Here, as the perimeter of the membranous member, for example, the region about the external edge of the membranous member (external being distal from the discharging port) can be selected as in the first aspect.

In the second aspect, it is not indispensable that the displacement member be disposed at the membranous member's one side at which the liquid to be discharged through the discharging port is provided, unlike in the first aspect. That is, in the second aspect, the position of the displacement member is not particularly limited and may be appropriately selected depending on the intended purpose so long as the displacement member is coupled to at least a part of the perimeter of the membranous member. Examples of the position of the displacement member in the second aspect include a position contacting the membranous member's one side at which the liquid is provided, a position contacting a side surface of the membranous member, and a position contacting a liquid discharging side (discharging surface side) of the membranous member.

The region that is the part of the perimeter of the membranous member in the second aspect may be, for example, a side of a polygon, when the planar shape of the membranous member is a polygon. In addition, in the case of being coupled to the whole perimeter of the membranous member in the second aspect, for example, the displacement member is coupled in a manner to surround the perimeter of the membranous member.

In the second aspect, a displacement member of the same kind as used in the first aspect can be used. For example, a piezoelectric element can be suitably used.

Here, in the second aspect, it is preferable that the displacement member be disposed at membranous member's one side at which the liquid is provided. This makes it possible to obtain a simple structure in which the displacement member is not displaced at the liquid discharging side of the membranous member, as described in the first aspect. This facilitates maintenance (cleaning) of the portion near the discharging port at the lower surface (discharging surface) side of the membranous member, providing a better maintenance convenience.

As obvious from the above, in the second aspect of the liquid discharging head of the present disclosure, it is preferable to dispose the displacement member at the membranous member's one side at which the liquid is provided, because this can further provide the same excellent technical effect as in the first aspect.

In the second aspect of the liquid discharging head of the present disclosure, it is preferable that the liquid discharging head include such members as a securing member, a liquid containing chamber, electrodes, and a cover as in the first aspect. It is preferable to include each of such members, because this can further provide an excellent technical effect as described in the first aspect.

[Third Aspect]

In the third aspect of the present disclosure, a liquid discharging head includes a membranous member including a discharging port through which a liquid is discharged, a displacement member configured to displace a position of the membranous member to cause the liquid to be discharged through the discharging port, and a coupling member configured to couple the membranous member and the displacement member to each other in a manner that the membranous member is mountable and demountable.

In the following description, the matters by which the third aspect is distinguished from the first aspect will be described. Hence, any matters of the third aspect not to be particularly described below may be the same as in the first aspect.

<Membranous Member>

The membranous member of the third aspect is not particularly limited and may be appropriately selected depending on the intended purpose so long as the membranous member includes a discharging port. The same membranous member as in the first aspect can be used.

<Displacement Member>

The displacement member of the third aspect is configured to displace the position of the membranous member to cause the liquid to be discharged through the discharging port.

Here, in the third aspect, the displacement member is coupled to the coupling member. That is, in the third aspect, the position of the displacement member is not particularly limited and may be appropriately selected depending on the intended purpose so long as the displacement member is coupled to the coupling member. It is not indispensable to dispose the displacement member at membranous member's one side at which the liquid to be discharged through the discharging port is provided. Examples of the position of the displacement member in the third aspect include a position at the membranous member's one side at which the liquid is provided, and a position at a liquid discharging side (discharging surface side) of the membranous member.

In the third aspect, a displacement member of the same kind as used in the first aspect can be used. For example, a piezoelectric element can be suitably used.

<Coupling Member>

The coupling member of the third aspect is configured to couple the membranous member and the displacement member to each other in a manner that the membranous member is mountable and demountable. Therefore, in the third aspect, because the membranous member is demountable, it is easy to demount only the membranous member when cleaning the liquid discharging head and clean the simple structure attributable to the membranous member.

The coupling member of the third aspect is not particularly limited and may be appropriately selected depending on the intended purpose so long as the coupling member can couple the membranous member and the displacement member to each other in a manner that the membranous member is mountable and demountable.

In the third aspect, as described below, it is preferable that the liquid discharging head include a liquid containing chamber. In this case, it is preferable that the coupling member couple the membranous member and the displacement member to each other via the liquid containing chamber. That is, it is preferable that the coupling member of the third aspect couple (support) the liquid containing chamber in a manner that the liquid containing chamber is mountable and demountable. In other words, it is preferable that the coupling member include a demounting member configured to couple (support) the liquid containing chamber in a manner that the liquid containing chamber is mountable and demountable.

As the demounting member of the third aspect, the same demounting member as in the first aspect can be used. With the coupling member coupling the liquid containing chamber in a manner that the liquid containing chamber is mountable and demountable, it is possible to perform replacement of the membranous member and the liquid containing chamber, making it possible to suppress contamination of liquids, when liquids to be discharged are changed.

<Liquid Containing Chamber>

As described above, in the third aspect, it is preferable that the liquid discharging head include a liquid containing chamber. As the liquid containing chamber of the third aspect, the same liquid containing chamber as in the first aspect can be used.

By including the liquid containing chamber, the liquid discharging head can contain the liquid to be discharged through the discharging port and have the liquid provided in a greater amount on the membranous member as in the first aspect. Hence, the liquid discharging head can contain the liquid by a predetermined thickness above the membranous member and stabilize the water pressure of the liquid above the membranous member when the liquid is to be discharged through the discharging port, making it possible to more stably discharge the liquid. Further, by including the liquid containing chamber, the liquid discharging head can provide the liquid in a greater amount above the membranous member. This makes it possible to reduce the number of times of supplying the liquid into the liquid discharging head and discharge more liquid droplets in a shorter time. Particularly, when forming a tissue formed of a plurality of cells by discharging a cell solution (cell suspension) from the liquid discharging head, it is possible to form the tissue in a shorter time, making it possible to suppress the cell survival rate from being lowered during formation.

Here, in the third aspect, it is preferable that the displacement member be disposed at membranous member's one side at which the liquid is provided. This makes it possible to obtain a simple structure in which the displacement member is not displaced at the liquid discharging side of the membranous member, as described in the first aspect. This facilitates maintenance (cleaning) of the portion near the discharging port at the lower surface (discharging surface) side of the membranous member, providing a better maintenance convenience.

As obvious from the above, in the third aspect of the liquid discharging head of the present disclosure, it is preferable to dispose the displacement member at the membranous member's one side at which the liquid is provided, because this can further provide the same excellent technical effect as in the first aspect.

In the third aspect of the liquid discharging head of the present disclosure, it is preferable that the liquid discharging head include such members as a securing member, electrodes, and a cover as in the first aspect. It is preferable to include each of such members, because this can further provide an excellent technical effect as described in the first aspect.

[Fourth Aspect]

In the fourth aspect of the present disclosure, a liquid discharging head includes a liquid retaining unit including a discharging port through which a liquid is discharged, and a displacement member configured to displace a position of the liquid retaining unit to cause the liquid to be discharged through the discharging port.

In the following description, the matters by which the fourth aspect is distinguished from the first aspect will be described. Hence, any matters of the fourth aspect not to be particularly described below may be the same as in the first aspect.

<Liquid Retaining Unit>

The liquid retaining unit is not particularly limited and may be appropriately selected depending on the intended purpose so long as the liquid retaining unit includes a discharging port through which a liquid is discharged and can retain the liquid.

As described above, the liquid retaining unit includes a discharging port (nozzle). It is preferable that the liquid retaining unit be capable of letting a gas pass through at least part of the liquid retaining unit. The liquid retaining unit capable of letting a gas pass through at least part of the liquid retaining unit means that the liquid retaining member can let a gas pass through between the inside and the outside of the liquid retaining unit.

It is preferable that the liquid retaining unit further include a ventilation port, and more preferably further include at least any one of an opening and an adhesion preventing member.

The shape, size, material, and structure of the liquid retaining unit are not particularly limited and may be appropriately selected depending on the intended purpose.

Examples of the material of the liquid retaining unit include metals such as stainless steel, nickel, and aluminum, plastics (resin materials) such ash ABS, polycarbonate, and fluororesins, and ceramics such as silicon dioxide, alumina, and zirconia. Among these materials, what is suitable to use is a material having a low adhesiveness with cells or proteins, when the liquid contained in the liquid retaining unit contains particles and cells or proteins are used as the particles.

Adhesiveness of a material with cells is said to be dependent on the contact angle of the material with respect to water. When the material has a high hydrophilicity or a high hydrophobicity, the material tends to have a low adhesiveness with cells. Examples of a material having a high hydrophilicity include various metals and ceramics (metal oxides). Examples of a material having a high hydrophobicity include fluororesins.

Further, it is preferable to reduce adhesiveness with cells by coating the surface of the material of the liquid chamber. Examples of coating over the surface of the material of the liquid chamber include coating the surface of the material with the metal or metal oxide materials described above, and coating the surface of the material with a synthetic phospholipid polymer mimicking a cellular membrane (e.g., LIPIDURE available from NOF Corporation).

Here, for example, the shape of the liquid retaining unit may be a cylindrical shape. When the liquid retaining unit has a cylindrical shape, an opening of the cylindrical shape at one side may be used as is as the discharging port of the liquid retaining unit, or a membranous member (nozzle plate) including a discharging port may be provided on the opening of the cylindrical shape at the one side.

<<Discharging Port>>

The discharging port (nozzle) refers to a port (hole) through which a liquid retained in the liquid retaining unit is discharged.

For example, the number of rows in which nozzles are arranged, the manner of arranging nozzles, the interval (pitch) between nozzles, the shape of the openings of nozzles, and the size of the openings of nozzles are not particularly limited and may be appropriately selected depending on the intended purpose.

When an opening of the cylindrical shape at one side is used as is as the discharging port of the liquid retaining unit, it is preferable to select the diameter of the opening so as not for the liquid retained in the liquid retaining unit to leak while the liquid retaining unit is stationary.

The shape of the openings of the discharging ports is not particularly limited and may be appropriately selected depending on the intended purpose. Examples of the shape include a circular shape, an elliptic shape, and a quadrangular shape.

The average diameter of the discharging ports is not particularly limited and may be appropriately selected depending on the intended purpose. When the liquid contained in the liquid chamber contains particles, the average diameter of the discharging ports is preferably two or more times greater than the size of the particles in order to avoid clogging the liquid discharging ports with the particles.

When the particles are, for example, animal cells, particularly, human cells, the average diameter of the discharging ports is preferably 10 micrometers or greater but 100 micrometers or less in conformity with the cells used, because human cells have a size of from 5 micrometers or greater but 50 micrometers or less.

On the other hand, in order to suppress a liquid droplet from becoming extremely large and facilitate formation of a minute liquid droplet, the average diameter of the discharging ports is preferably 200 micrometers or less. Hence, the average diameter of the discharging ports is more preferably 10 micrometers or greater but 200 micrometers or less.

When the liquid retaining unit has a cylindrical shape and a membranous member including a discharging port is provided on an opening of the cylindrical shape at one side, the same membranous member as in the first aspect can be used as the membranous member.

When the liquid retaining unit has a cylindrical shape, the diameter of the liquid retaining unit is not limited to a constant diameter, but may be varied from place to place. In this case, it is preferable to increase the diameter of the cylindrical shape from the opening of the cylindrical shape functioning as the discharging port toward the opening at the opposite side. In this way, in the fourth aspect, it is possible to suppress the diameter at the discharging port side and make the liquid retaining unit capable of retaining the liquid in a high amount. This makes it possible to make the liquid retaining unit retain the liquid in a high amount without making the liquid discharging head large in size, making it possible to reduce the number of times of supplying the liquid into the liquid discharging head and discharge more liquid droplets in a shorter time.

Further, in the fourth aspect, the liquid retaining unit may have a branched structure and discharge a plurality of kinds of liquids after mixing the liquids in the liquid retaining unit. More specifically, for example, different kinds of liquids may be retained in the flow paths constituting the branched structure of the liquid retaining unit, and the liquids may be mixed at an immediate upstream of the discharging port as a mixture liquid, which may be discharged through the discharging port. In this way, in the fourth aspect, for example, by mixing and discharging liquids that are chemically reactive with each other, it is possible to discharge the liquids while allowing the liquids to undergo a chemical reaction.

As described above, it is preferable that the liquid retaining unit include a ventilation port, and more preferably further include at least any one of an opening and an adhesion preventing member.

The ventilation port, the opening, and the adhesion preventing member of the liquid retaining unit may be the same as the ventilation port, the opening, and the adhesion preventing member of the liquid containing chamber of the first aspect.

Particularly, when the liquid retaining unit has a cylindrical shape, the ventilation port and the opening may be an opening of the cylindrical shape at a side opposite to an opening of the cylindrical shape functioning as the discharging port.

<Displacement Member>

The displacement member of the fourth aspect is configured to displace the position of the liquid retaining unit to cause the liquid to be discharged through the discharging port.

As the displacement member of the fourth aspect, the same displacement member as in the first aspect can be used.

In the liquid discharging head, the displacement member displaces the position of the liquid retaining unit to apply an inertial force to the liquid retained in the liquid retaining unit, and this enables the liquid contained in the liquid retaining unit to be discharged through the discharging port.

Further, the liquid discharging head may perform preparatory discharging for stabilizing discharging of the liquid, by letting the displacement member displace the position of the liquid retaining unit. Further, the liquid discharging head may stir the liquid retained in the liquid retaining unit by letting the displacement member displace the position of the liquid retaining unit.

When the liquid discharging head includes a coupling member, the displacement member displaces the positions of the liquid retaining unit and the coupling member together.

The direction in which the displacement member displaces the position of the liquid retaining unit is not particularly limited and may be appropriately selected depending on the intended purpose. When the liquid discharging head performs discharging of the liquid, it is preferable that the displacement member displace the position of the liquid retaining unit in the liquid discharging direction. It is preferable that the liquid discharging direction be approximately the gravity direction.

When the displacement member displaces the position of the liquid retaining unit, it is preferable that the displacement member reciprocate the liquid retaining unit, and more preferably vibrate the liquid retaining unit.

In the fourth aspect, it is preferable that the displacement member displace the position of the liquid retaining unit by reciprocating the liquid retaining unit in a direction approximately parallel with a direction in which the liquid is discharged through the discharging port. In this way, in the fourth aspect, it is possible to discharge the liquid more efficiently and discharge the liquid more truly to the desired position.

In this way, in the fourth aspect of the liquid discharging head of the present disclosure, the position of the whole liquid retaining unit including the discharging port (nozzle) is displaced, to cause the liquid to be discharged. Hence, in the liquid discharging head of the fourth aspect, there is no need for largely displacing the portion corresponding to the nozzle portion of the membranous member of an existing liquid discharging head. Therefore, the liquid discharging head can use a short (small) nozzle plate (the nozzle plate being the portion corresponding to the membranous member of an existing liquid discharging head). Hence, the liquid discharging head of the fourth embodiment can be reduced in size as compared with existing liquid discharging units. If it is possible to reduce the size of the liquid discharging head, it is possible to install many liquid discharging heads in one liquid discharging apparatus. Therefore, when forming a tissue by, for example, discharging a cell solution (cell suspension), a liquid discharging apparatus including the liquid discharging head of the fourth aspect can form the tissue formed of a plurality of cells in a shorter time. This makes it possible to suppress the cell survival rate from being lowered during formation.

Here, as the displacement member of the fourth aspect, the same displacement member as used in the first aspect can be used. For example, a piezoelectric element can be suitably used.

When a piezoelectric element is used as the displacement member of the fourth aspect, the vibration mode of the piezoelectric element is preferably a longitudinal mode. In this case, for example, coupling the displacement member to the top of the liquid retaining unit or to the coupling member coupled to the top of the liquid retaining unit to vibrate the liquid retaining unit in the approximately gravity direction can cause the liquid to be discharged more efficiently and more truly to the desired position.

It is preferable to provide the displacement member in a manner to contact the coupling member. It is more preferable to provide the displacement member in a manner to contact the supporting member and a securing member configured to secure the displacement member.

<Securing Member>

In the fourth aspect of the liquid discharging head of the present disclosure, it is preferable that the liquid discharging head include a securing member (securing unit) configured to secure a side of the displacement member opposite to a side of the displacement member contacting the liquid retaining unit or the coupling member. By including the securing member, the liquid discharging head can be improved in the latitude in selection of the position at which the liquid discharging head is disposed. For example, this makes it easier to dispose a plurality of liquid discharging heads side by side.

Here, the shape, size, material, and structure of the securing member are not particularly limited and may be appropriately selected depending on the intended purpose so long as the securing member can secure the side of the displacement member opposite to the side of the displacement member contacting the liquid retaining unit.

In the fourth aspect, it is preferable that the securing member be formed of a material that has a high stiffness and does not easily deform. Examples of the material that can be applied as the securing member, and has a high stiffness and does not easily deform include metal materials such as stainless steel and ceramic materials.

The securing member formed of the material that has a high stiffness and does not easily deform can suppress loss of displacing energy of the displacement member, making it possible to displace the position of the liquid retaining unit efficiently and cause the liquid to be discharged through the discharging port more efficiently.

<Coupling Member>

In the fourth aspect of the liquid discharging head of the present disclosure, it is preferable that the liquid discharging head include a coupling member (supporting member) configured to couple the liquid retaining unit and the securing member to each other. With the liquid discharging head provided with the coupling member, it is possible to better improve the latitude in selection of the shape and disposition of the liquid discharging head, and make it easier to dispose many liquid discharging heads side by side.

The shape, size, material, and structure of the coupling member are not particularly limited and may be appropriately selected depending on the intended purpose.

Examples of the material of the coupling member include metals such as stainless steel, nickel, and aluminum, plastics such as ABS, polycarbonate, and fluororesins, and ceramics such as silicon dioxide, alumina, and zirconia.

The method by which the coupling member couples (supports) the liquid retaining unit and the securing member to each other is not particularly limited and may be appropriately selected depending on the intended purpose. Examples of the method include a method of supporting the liquid retaining unit in a manner that at least part of the ventilation port of the liquid retaining unit is opened, and a method of forming a ventilation port also in the coupling member and making the coupling member couple (support) the liquid retaining unit in a manner that a gas can circulate through the ventilation port of the liquid retaining unit and the ventilation port of the coupling member.

It is preferable that the coupling member couple (support) the liquid retaining unit in a manner that the liquid retaining unit is mountable and demountable. In other words, it is preferable that the coupling member include a demounting member configured to couple (support) the liquid retaining unit in a manner that the liquid retaining unit is mountable and demountable. With the coupling member coupling the liquid retaining unit in a manner that the liquid retaining unit is mountable and demountable, it is possible to perform replacement of the liquid retaining unit, making it possible to suppress contamination of liquids, when liquids to be discharged are changed.

In an example of a preferable aspect of the fourth aspect of the liquid discharging head of the present disclosure, i.e., in an aspect in which the coupling member couples the liquid retaining unit in a manner that the liquid retaining unit is mountable and demountable, the displacement member displaces the position of the whole liquid retaining unit via the coupling member to cause the liquid to be discharged. Hence, the displacement member is not provided on the liquid retaining unit. Therefore, in this aspect, the coupling member that couples the liquid retaining unit in a manner that the liquid retaining unit is mountable and demountable enables replacement of the liquid retaining unit in a short time when replacement of the liquid retaining unit is needed.

Further, it is particularly advantageous to be capable of replacing the liquid retaining unit in a short time, because the cell survival rate can be suppressed from being lowered during, for example, formation of a tissue formed of a plurality of cells.

The demounting member is not particularly limited and may be appropriately selected depending on the intended purpose. Examples of the demounting member include a threadedly coupling member such as a screw configured to support the liquid retaining unit in a biasing manner, an elastic body configured to support the liquid retaining unit in a biasing manner, and a magnetic body configured to support the liquid retaining unit with a magnetic force. One of these members may be used alone or two or more of these members may be used in combination. Among these members, the elastic body configured to support the liquid retaining unit in a biasing manner and the magnetic body configured to support the liquid retaining unit with a magnetic force are preferable as the demounting member.

It is preferable that the demounting member include an elastic body and that the elastic body bias the liquid retaining unit to support the liquid retaining unit in a non-detachable manner. With the demounting member including the elastic body and the elastic body biasing the liquid retaining unit to support the liquid retaining unit in a non-detachable manner, it is possible to replace the liquid retaining unit in a shorter time easily.

The elastic body is not particularly limited and may be appropriately selected depending on the intended purpose. Examples of the elastic body include a rubber, a coil spring, a leaf spring, and a torsion bar. Among these elastic bodies, a leaf spring is preferable. One of these elastic bodies may be used alone or two or more of these elastic bodies may be used in combination.

The liquid retaining unit being supported in a non-detachable manner means that the liquid retaining unit can be mounted or demounted by, for example, a user when replacing the liquid retaining unit, but that the liquid retaining unit can be supported when the liquid retaining unit is stationary and when the liquid retaining unit is displaced (vibrated) by the displacement member.

It is also preferable that the demounting member include a magnetic body and that the magnetic body support the liquid retaining unit in a non-detachable manner with a magnetic force. With the demounting member including the magnetic body and the magnetic body supporting the liquid retaining unit in a non-detachable manner with a magnetic force, it is possible to replace the liquid retaining unit in a shorter time easily.

The magnetic body means a body that generates a magnetic field. Examples of the magnetic body include a permanent magnet and an electromagnet. Of these magnetic bodies, a permanent magnet is preferable. One of these magnetic bodies may be used alone or two or more of these magnetic bodies may be used in combination.

When the demounting member includes a magnetic body, it is preferable that the liquid retaining unit include an adsorbing member configured to generate an attractive force with respect to the coupling member by means of the magnetic force generated by the magnetic body. The adsorbing member is not particularly limited and may be appropriately selected depending on the intended purpose. Examples of the adsorbing member include ferromagnetic metals such as iron, cobalt, and nickel. One of these adsorbing members may be used alone or two or more of these adsorbing members may be used in combination.

Further, in the fourth aspect of the liquid discharging head of the present disclosure, it is preferable that there be a plurality of liquid retaining units and that the coupling member couple the liquid retaining units in a manner that the liquid retaining units can be disposed adjacently. Here, the coupling member coupling the liquid retaining units in a manner that the liquid retaining units can be disposed adjacently means that, for example, when forming a multichannel by disposing a plurality of liquid retaining units side by side, the liquid retaining units can be disposed closely adjacently with each other in a direction in which the liquid retaining units are disposed side by side.

The method by which the coupling member couples the liquid retaining units in a manner that the liquid retaining units can be disposed adjacently is not particularly limited and may be appropriately selected depending on the intended purpose. Examples of the method include a method of making the diameter of the coupling member shorter than the diameter of the liquid retaining unit in the direction in which the plurality of liquid retaining units are disposed side by side.

With the coupling member coupling the liquid retaining units in a manner that the liquid retaining units can be disposed adjacently, it is possible to make the liquid discharging head smaller in size. This makes it possible to dispose the liquid retaining units more closely when forming a multichannel by disposing a plurality of liquid retaining units side by side, making it possible to install a greater number of liquid discharging heads in one liquid discharging apparatus. In this way, for example, when forming a tissue formed of a plurality of cells by discharging a cell solution (cell suspension), it is possible to form the tissue in a shorter time and suppress the cell survival rate from being lowered during formation.

The liquid discharging heads according to the second to fourth aspects may include other members like the liquid discharging head according to the first aspect. The other members are not particularly limited and may be appropriately selected depending on the intended purpose.

(Liquid Discharging Apparatus)

A liquid discharging apparatus of the present disclosure includes the liquid discharging head of the present disclosure, preferably includes a driving unit and a particle number counting unit, and further includes other units as needed.

<Driving Unit>

The driving unit is not particularly limited and may be appropriately selected depending on the intended purpose. Examples of the driving unit include a unit configured to input a drive voltage to a liquid discharging unit. In this case, it is possible to discharge minute liquid droplets, by a piezoelectric element being deformed by the driving unit.

<Particle Number Counting Unit>

The particle number counting unit is a unit configured to count the number of particles contained in liquid droplets, and is preferably a unit configured to count the number of particles contained in liquid droplets with a sensor after the liquid droplets are discharged and before the liquid droplets land on a landing target.

A sensor means a device configured to, by utilizing some scientific principles, change mechanical, electromagnetic, thermal, acoustic, or chemical properties of natural phenomena or artificial products or spatial information/temporal information indicated by these properties into signals, which are a different medium easily handleable by humans or machines.

The particle number counting unit is not particularly limited, may be appropriately selected depending on the intended purpose, and may include an operation for observing particles before discharging and an operation for counting particles after landing.

For an operation for counting the number of particles contained in the liquid droplets after the liquid droplets are discharged and before the liquid droplets land on the landing target, it is preferable to observe particles in a liquid droplet at a timing at which the liquid droplet is at a position that is immediately above a well opening and at which the liquid droplet is predicted to enter the well in a plate as the landing target without fail.

The plate is not particularly limited, and a plate that is commonly used in bio fields and in which holes are formed can be used.

The number of wells in the plate is not particularly limited and may be appropriately selected depending on the intended purpose. The number of wells may be a single number or a plural number.

As a plate with a plural number of wells, it is preferable to use plates in which 24, 96, 384, or such a number of wells or holes as commonly used in the industry are formed with dimensions commonly used in the industry.

The material of the plate is not particularly limited and may be appropriately selected depending on the intended purpose. In consideration of a post-treatment, it is preferable to use a material that suppresses adhesion of cells and nucleic acids to wall surfaces.

Examples of the method for observing particles in the liquid droplet include an optical detection method and an electric or magnetic detection method.

<Other Units>

The other units are not particularly limited and may be appropriately selected depending on the intended purpose. Examples of the other units include a control unit, a display unit, and a recording unit.

Here, embodiments of the liquid discharging apparatus of the present disclosure will be described in detail with reference to the drawings.

The liquid discharging apparatus of the present disclosure includes the liquid discharging head of the present disclosure as a liquid discharging head, and the liquid discharging head of the present disclosure is included in the liquid discharging apparatus of the present disclosure. Hence, embodiments of the liquid discharging head of the present disclosure will also be described through the following description of the embodiments of the liquid discharging apparatus of the present disclosure.

In the respective drawings, the same constituents will be denoted by the same reference numerals, and any redundant description may be skipped. For example, the number, position, and shape of the constituents are not limited to as specified in the embodiments, but may be any number, position, and shape that are suitable for working the present disclosure.

Cross-sectional views among the drawings are cross-sectional views taken at a position at which a discharging port (nozzle) is formed in the liquid discharging head.

First Embodiment

Figure 1B:
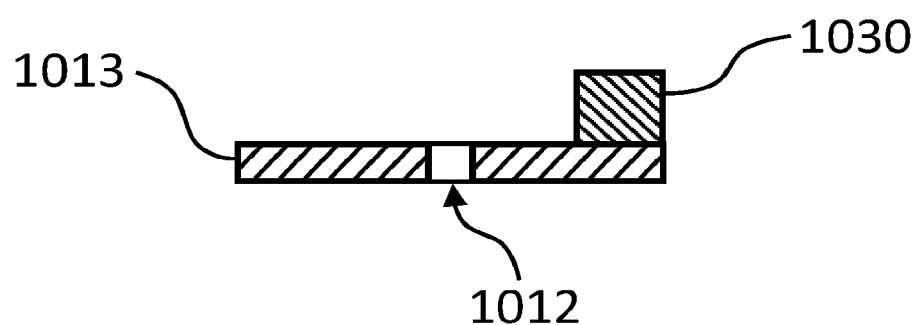
FIG. 1B is a schematic cross-sectional view of an example liquid discharging head according to a first embodiment.

FIG. 1A is a schematic top view of an example liquid discharging head of the first embodiment. FIG. 1B is a schematic cross-sectional view of an example liquid discharging head of the first embodiment.

As illustrated in FIG. 1A and FIG. 1B, in the first embodiment, in a liquid discharging head 1100, a discharging port (nozzle) 1012 is formed in the center of a membranous member 1013 having a quadrangular planar shape, and a piezoelectric element 1030 as an example of a displacement member is bonded in contact with one side of the membranous member 1013.

In the first embodiment, the piezoelectric element 1030 is displaced at a side at which the liquid to be discharged through the discharging port 1012 is provided.

Figure 2:
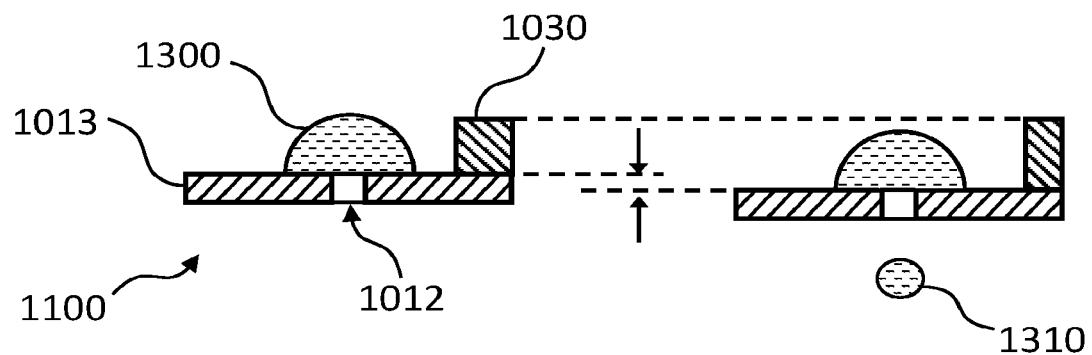
FIG. 2 is a schematic cross-sectional view illustrating an example operation of an example liquid discharging head according to a first embodiment when discharging a liquid through a discharging port.

FIG. 2 is a schematic cross-sectional view illustrating an example operation of an example liquid discharging head according to the first embodiment when discharging a liquid through a discharging port.

In the first embodiment, the piezoelectric element 1030 of a longitudinal mode (laminated type) is elongated and contracted (to elongate in the longitudinal direction and contract in the lateral direction in FIG. 2), to displace the position of the membranous member 1013, to cause a liquid droplet 1310 to be discharged through the discharging port 1012 from the liquid 1300 provided on the membranous member 1013. More specifically, in the first embodiment, the position of the membranous member 1013 is reciprocated by the longitudinal mode piezoelectric element 1030 in a direction in which the liquid droplet 1310 is to be discharged (discharging direction), to cause the liquid droplet 1310 to be discharged through the discharging port 1012.

In the first embodiment, as described above, along with the position of the membranous member 1013 being displaced, the discharging port 1012 is displaced, to induce an increase in the pressure in the liquid 1300 to be discharged, to cause the liquid droplet 1310 to be discharged through the discharging port 1012.

In the first embodiment, because displacement is performed at the edge of the membranous member 1013 to cause the liquid 1300 to be discharged, it is not indispensable to deform the membranous member 1013 while the displacement member 1030 is displacing the position of the membranous member 1013. Therefore, there is no need for deforming the membranous member 1013.

Hence, in the first embodiment, it is possible to simplify the structure and use a smaller (shorter) membranous member, making it possible to make the liquid discharging head smaller in size.

Use of the longitudinal mode piezoelectric element 1030 as in the first embodiment enables use of a piezoelectric element having a small width, making it possible to reduce the width (the size in the horizontal direction) of the liquid discharging head 1100. In the case of using the longitudinal mode piezoelectric element 1030 as in the first embodiment, it is preferable to use a piezoelectric element 1030 having a thickness of a certain degree, in order to make the membranous member 1013 be displaced by a large amount (an amount by which the position is changed).

In this way, in the first embodiment, the longitudinal mode piezoelectric element 1030 as an example of the displacement member is disposed at the side at which the liquid to be discharged through the discharging port 1012 is provided. This may be an example of the first aspect described above. A case of the membranous member 1013 where the membranous member 1013 does not deform while the displacement member 1030 is displacing the position of the membranous member 1013 may be an example of the second aspect described above.

Second Embodiment

Figure 3:
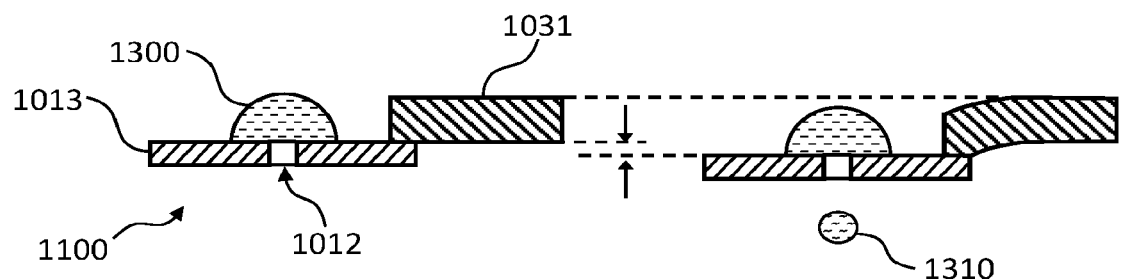
FIG. 3 is a schematic cross-sectional view illustrating an example operation of an example liquid discharging head according to a second embodiment when discharging a liquid through a discharging port.

FIG. 3 is a schematic cross-sectional view illustrating an example operation of an example liquid discharging head according to the second embodiment when discharging a liquid through a discharging port.

In the second embodiment, a piezoelectric element 1031 of a shear mode (bimorph type) is used as an example of the displacement member, unlike in the first embodiment. The second embodiment may be the same as the first embodiment in any other respects than the displacement member.

In the second embodiment, a discharging port (nozzle) 1012 is formed in the center of a membranous member 1013 having a quadrangular planar shape, and a piezoelectric element 1031 as an example of a displacement member is bonded in contact with one side of the membranous member 1013 as in the first embodiment.

In the second embodiment, a shear mode piezoelectric element 1031 is deformed (bent), to displace the position of the membranous member 1013, to cause a liquid droplet 1310 to be discharged through the discharging port 1012. More specifically, in the second embodiment, the position of the membranous member 1013 is reciprocated by the shear mode piezoelectric element 1031 in a direction in which the liquid droplet 1310 is to be discharged (discharging direction), to cause the liquid droplet 1310 to be discharged through the discharging port 1012.

Use of the shear mode piezoelectric element 1031 as in the second embodiment enables use of a thin piezoelectric element, making it possible to reduce the thickness (the size in the vertical direction) of the liquid discharging head 1100. In the case of using the shear mode piezoelectric element 1031 as in the second embodiment, it is preferable to use a piezoelectric element 1031 having a width (length) of a certain degree, in order to make the membranous member 1013 be displaced by a large amount (an amount by which the position is changed).

In this way, in the second embodiment, the shear mode piezoelectric element 1031 as an example of the displacement member is disposed at the side at which the liquid to be discharged through the discharging port 1012 is provided. This may be an example of the first aspect described above. A case of the membranous member 1013 where the membranous member 1013 does not deform while the displacement member 1031 is displacing the position of the membranous member 1013 may be an example of the second aspect described above.

Third Embodiment

Figure 4:
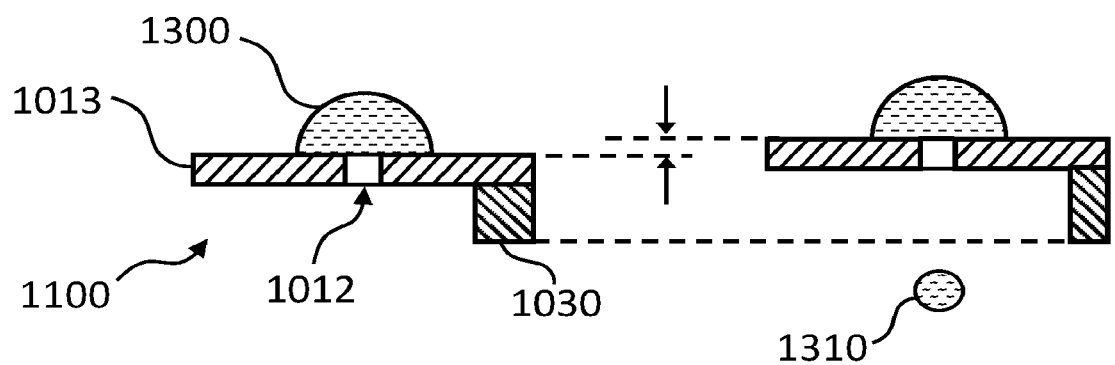
FIG. 4 is a schematic cross-sectional view illustrating an example operation of an example liquid discharging head according to a third embodiment when discharging a liquid through a discharging port.

FIG. 4 is a schematic cross-sectional view illustrating an example operation of an example liquid discharging head according to the third embodiment when discharging a liquid through a discharging port.

In the third embodiment, the piezoelectric element 1030 is disposed at a side (discharging surface side) of a membranous member 1013 opposite to membranous member 1013's one side at which the liquid 1300 is provided unlike in the first embodiment. Further, in the third embodiment, as the membranous member 1013, a membranous member 1013 that does not deform while the displacement member 1030 is displacing the position of the membranous member 1013 is used. The third embodiment may be the same as the first embodiment in any other respects.

As illustrated in FIG. 4, the position of the membranous member 1013 is reciprocated by a longitudinal mode piezoelectric element 1030 in a direction in which the liquid droplet 1310 is to be discharged (discharging direction), to cause the liquid droplet 1310 to be discharged through the discharging port 1012.

In the third embodiment, because a membranous member 1013 that has a high stiffness and does not deform while the displacement member 1030 is displacing the position of the membranous member 1013 is used, the size and thickness of the membranous member 1013 can be appropriately selected. Hence, in the third embodiment, the structure of the liquid discharging head 1100 can be simplified and made small in size.

In the third embodiment, because having a high stiffness, the membranous member 1013 can have an improved durability in continuous discharging of the liquid 1300, and can be suppressed from being damaged when the membranous member 1013 is cleaned with a cleaning device such as a brush.

In the third embodiment, a case of using a longitudinal mode piezoelectric element 1030 has been described. However, a shear mode piezoelectric element may also be used as in the second embodiment.

In this way, in the third embodiment, the membranous member does not deform while the displacement member is displacing the position of the membranous member. This may be an example of the second aspect described above.

Fourth Embodiment

Figure 5A:
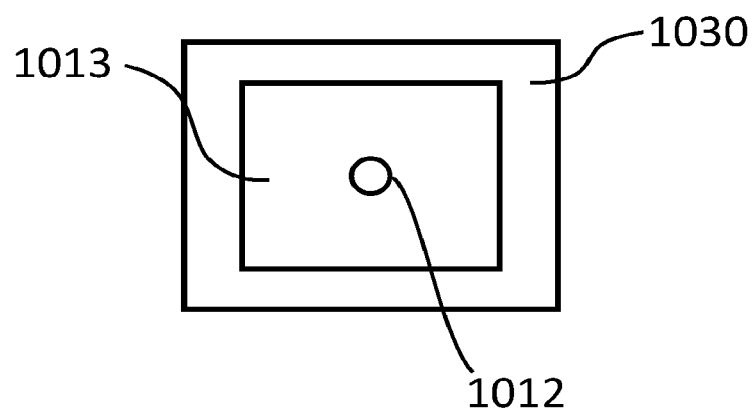
FIG. 5A is a schematic top view of an example liquid discharging head according to a fourth embodiment.
Figure 5B:
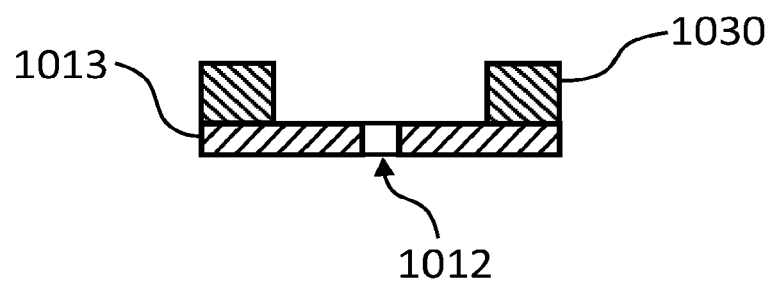
FIG. 5B is a schematic cross-sectional view of an example liquid discharging head according to a fourth embodiment.

FIG. 5A is a schematic top view of an example liquid discharging head according to the fourth embodiment. FIG. 5B is a schematic cross-sectional view illustrating an example liquid discharging head according to the fourth embodiment.

As illustrated in FIG. 5A and FIG. 5B, in the fourth embodiment, in the liquid discharging head 1100, a discharging port (nozzle) 1012 is formed in the center of a membranous member 1013 having a quadrangular planar shape, and a piezoelectric element 1030 as an example of a displacement member is bonded in contact with the membranous member 1013 in a manner to surround the perimeter of the membranous member 1013 and to be capable of retaining the liquid 1300 to be provided on the membranous member 1013.

In the fourth embodiment, the piezoelectric element 1030 is disposed at a side at which the liquid to be discharged through the discharging port 1012 is provided.

Figure 6:
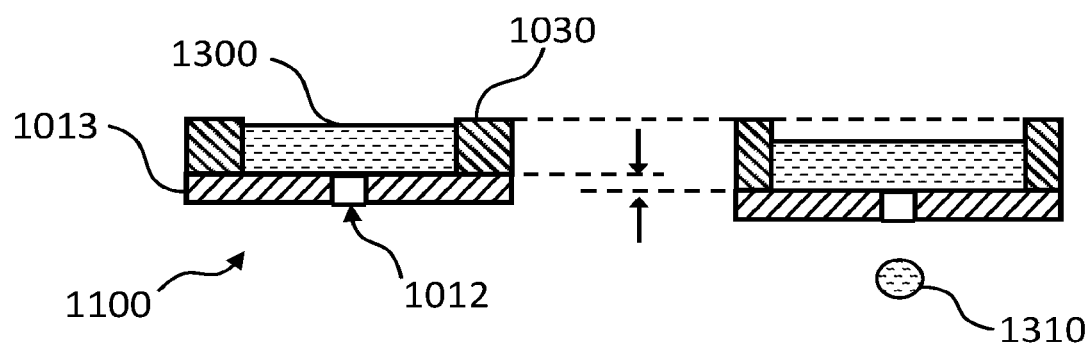
FIG. 6 is a schematic cross-sectional view illustrating an example operation of an example liquid discharging head according to a fourth embodiment when discharging a liquid through a discharging port.

FIG. 6 is a schematic cross-sectional view illustrating an example operation of the example liquid discharging head according to the fourth embodiment when discharging a liquid through a discharging port.

In the fourth embodiment, the piezoelectric element 1030 of a longitudinal mode (laminated type) is elongated and contracted (to elongate in the longitudinal direction and contract in the lateral direction in FIG. 6), to displace the position of the membranous member 1013, to cause a liquid droplet 1310 to be discharged through the discharging port 1012 from the liquid 1300 provided on the membranous member 1013. More specifically, in the fourth embodiment, the position of the membranous member 1013 is reciprocated by the longitudinal mode piezoelectric element 1030 in a direction in which the liquid droplet 1310 is to be discharged (discharging direction), to cause the liquid droplet 1310 to be discharged through the discharging port 1012.

In the fourth embodiment, as described above, along with the position of the membranous member 1013 being displaced, the discharging port 1012 is displaced, to induce an increase in the pressure in the liquid 1300 to be discharged, to cause the liquid droplet 1310 to be discharged through the discharging port 1012.

In the fourth embodiment, because displacement is performed at the edge of the membranous member 1013 to cause the liquid 1300 to be discharged, it is not indispensable to deform the membranous member 1013 while the displacement member 1030 is displacing the position of the membranous member 1013. Therefore, there is no need for deforming the membranous member 1013.

Hence, in the fourth embodiment, it is possible to simplify the structure and use a smaller (shorter) membranous member, making it possible to make the liquid discharging head smaller in size.

Use of the longitudinal mode piezoelectric element 1030 as in the fourth embodiment enables use of a piezoelectric element having a small width, making it possible to reduce the width (the size in the horizontal direction) of the liquid discharging head 1100. In the case of using the longitudinal mode piezoelectric element 1030 as in the fourth embodiment, it is preferable to use a piezoelectric element 1030 having a thickness of a certain degree, in order to make the membranous member 1013 be displaced by a large amount (an amount by which the position is changed).

Here, in the fourth embodiment, because the liquid 1300 is retained by the longitudinal mode piezoelectric element 1030, the liquid 1300 can be provided in a greater amount on the membranous member 1013. With the liquid 1300 retained by the longitudinal mode piezoelectric element 1030, the liquid discharging head 1100 can retain the liquid 1300 by a predetermined thickness above the membranous member 1013 and stabilize the water pressure of the liquid 1300 above the membranous member 1013 when the liquid 1300 is to be discharged through the discharging port 1012. This enables more stable discharging of a liquid droplet 1310.

Further, in the fourth embodiment, because the longitudinal mode piezoelectric element 1030 is used, it is possible to appropriately select the shape of the longitudinal mode piezoelectric element 1030 when disposing the longitudinal mode piezoelectric element 1030 in a manner to surround the perimeter of the membranous member 1013.

Figure 7A:
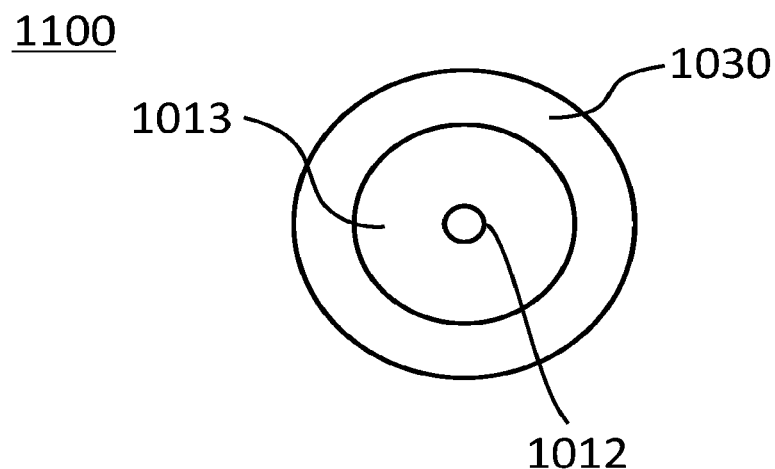
FIG. 7A is a schematic top view of a modified liquid discharging head according to a fourth embodiment.
Figure 7B:
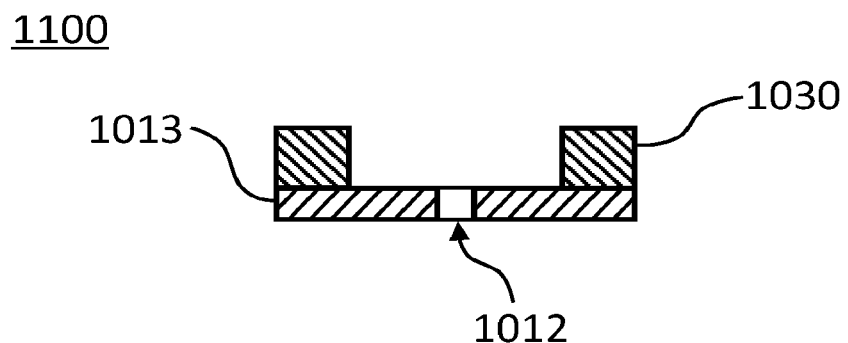
FIG. 7B is a schematic cross-sectional view of a modified liquid discharging head according to a fourth embodiment.

FIG. 7A is a schematic top view of a modified liquid discharging head according to the fourth embodiment. FIG. 7B is a schematic cross-sectional view of a modified liquid discharging head according to the fourth embodiment.

As illustrated in FIG. 7A and FIG. 7B, in the fourth embodiment, in the discharging head 1100, a discharging port (nozzle) 1012 is formed in the center of a membranous member 1013 having a circular planar shape, and a piezoelectric element 1030 as an example of a displacement member is bonded in contact with the membranous member 1013 in a manner to surround the perimeter of the membranous member 1013 and to be capable of retaining the liquid 1300 to be provided on the membranous member 1013. As illustrated in the modified example of FIG. 7A and FIG. 7B, in the fourth embodiment, the planar shape of the membranous member 1013 and the shape of the longitudinal mode piezoelectric element 1030 can be appropriately selected.

In this way, in the fourth embodiment, the longitudinal mode piezoelectric element 1030 as an example of the displacement member is disposed at the side at which the liquid to be discharged through the discharging port 1012 is provided. This may be an example of the first aspect described above. A case of the membranous member 1013 where the membranous member 1013 does not deform while the displacement member 1030 is displacing the position of the membranous member 1013 may be an example of the second aspect described above.

Fifth Embodiment

Figure 8:
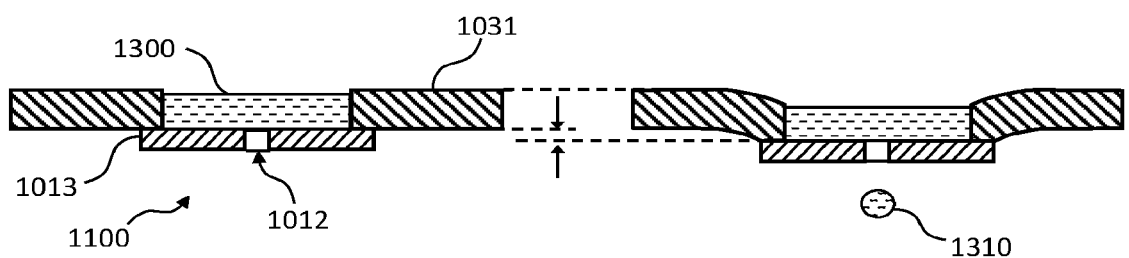
FIG. 8 is a schematic cross-sectional view illustrating an example operation of an example liquid discharging head according to a fifth embodiment when discharging a liquid through a discharging port.

FIG. 8 is a schematic cross-sectional view illustrating an example operation of an example liquid discharging head according to the fifth embodiment when discharging a liquid through a discharging port.

In the fifth embodiment, a piezoelectric element 1031 of a shear mode (bimorph type) is used as an example of the displacement member unlike in the fourth embodiment. The fifth embodiment may be the same as the fourth embodiment in any other respects than the displacement member.

In the fifth embodiment, a discharging port (nozzle) 1012 is formed in the center of a membranous member 1013 having a circular planar shape, and a piezoelectric element 1031 as an example of a displacement member is bonded in contact with the membranous member 1013 in a manner to surround the perimeter of the membranous member 1013 as in the modified example of the fourth embodiment.

In the fifth embodiment, a shear mode piezoelectric element 1031 is deformed (bent), to displace the position of the membranous member 1013, to cause a liquid droplet 1310 to be discharged through the discharging port 1012. More specifically, in the fifth embodiment, the position of the membranous member 1013 is reciprocated by the shear mode piezoelectric element 1031 in a direction in which the liquid droplet 1310 is to be discharged (discharging direction), to cause the liquid droplet 1310 to be discharged through the discharging port 1012.

Use of the shear mode piezoelectric element 1031 as in the fifth embodiment enables use of a thin piezoelectric element, making it possible to reduce the thickness (the size in the vertical direction) of the liquid discharging head 1100. In the case of using the shear mode piezoelectric element 1031 as in the fifth embodiment, it is preferable to use a piezoelectric element 1031 having a width (length) of a certain degree, in order to make the membranous member 1013 be displaced by a large amount (an amount by which the position is changed).

In the fifth embodiment, the shear mode piezoelectric element 1031 is disposed in an annular (ring-like) shape, in order to displace the membranous member 1013 stably.

In this way, in the fifth embodiment, the shear mode piezoelectric element 1031 as an example of the displacement member is disposed at the side at which the liquid to be discharged through the discharging port 1012 is provided. This may be an example of the first aspect described above. A case of the membranous member 1013 where the membranous member 1013 does not deform while the displacement member 1031 is displacing the position of the membranous member 1013 may be an example of the second aspect described above.

Sixth Embodiment

Figure 9A:
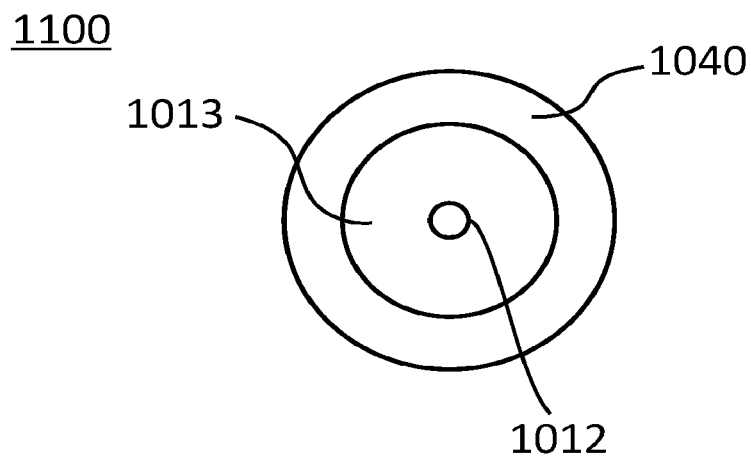
FIG. 9A is a schematic top view of an example liquid discharging head according to a sixth embodiment.
Figure 9B:
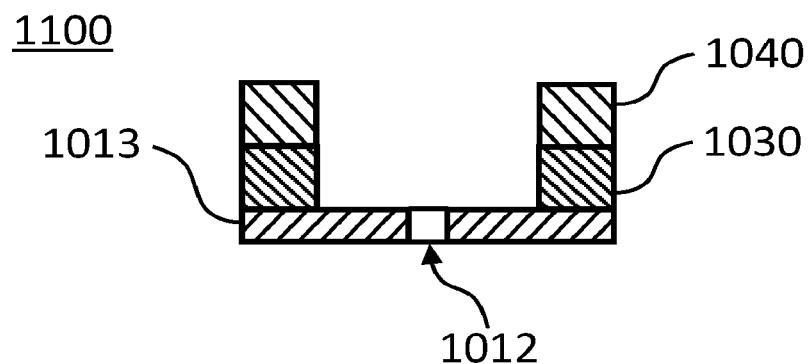
FIG. 9B is a schematic cross-sectional view of an example liquid discharging head according to a sixth embodiment.

FIG. 9A is a schematic top view of an example liquid discharging head according to the sixth embodiment. FIG. 9B is a schematic cross-sectional view of an example liquid discharging head according to the sixth embodiment.

As illustrated in FIG. 9A and FIG. 9B, in the sixth embodiment, in the liquid discharging head 1100, a discharging port (nozzle) 1012 is formed in the center of a membranous member 1013 having a circular planar shape, and a piezoelectric element 1030 as an example of a displacement member is bonded in contact with the membranous member 1013 in a manner to surround the perimeter of the membranous member 1013 and to be capable of retaining the liquid 1300 to be provided on the membranous member 1013.

In the sixth embodiment, the liquid discharging head 1100 includes a securing member 1040 disposed at membranous member 1013's one side at which the liquid is provided and configured to secure a side of the displacement member 1030 opposite to a side of the displacement member 1030 contacting the membranous member 1013.

The sixth embodiment may be the same as the fourth embodiment in any other respects than including the securing member 1040.

In the sixth embodiment, by including the securing member 1040, the liquid discharging head 1100 can be improved in the latitude in selection of the position at which the liquid discharging head 1100 is disposed. For example, this makes it easier to dispose a plurality of liquid discharging heads 1100 side by side.

Further, in the sixth embodiment, selection of a material that has a high stiffness and does not easily deform as the material of the securing member 1040 can suppress loss of displacing energy of the displacement member 1030, making it possible to displace the position of the membranous member 1013 efficiently and cause the liquid to be discharged through the discharging port 1012 more efficiently.

In this way, in the sixth embodiment, the longitudinal mode piezoelectric element 1030 as an example of the displacement member is disposed at the side at which the liquid to be discharged through the discharging port 1012 is provided. This may be an example of the first aspect described above. A case of the membranous member 1013 where the membranous member 1013 does not deform while the displacement member 1030 is displacing the position of the membranous member 1013 may be an example of the second aspect described above.

Seventh Embodiment

Figure 10A:
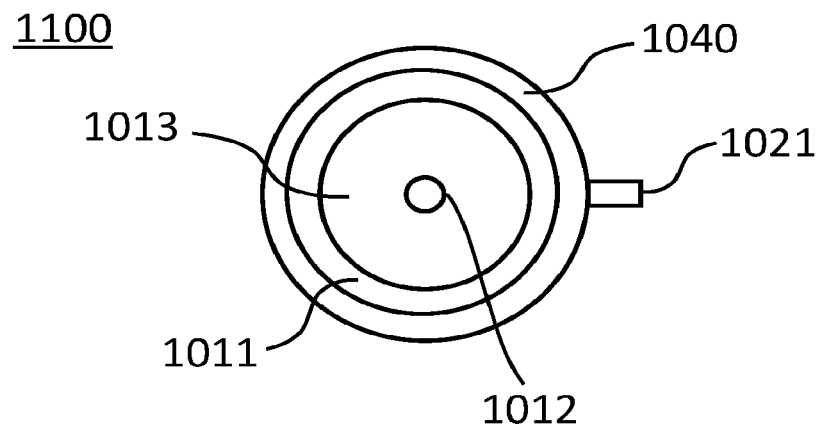
FIG. 10A is a schematic top view of an example liquid discharging head according to a seventh embodiment.
Figure 10B:
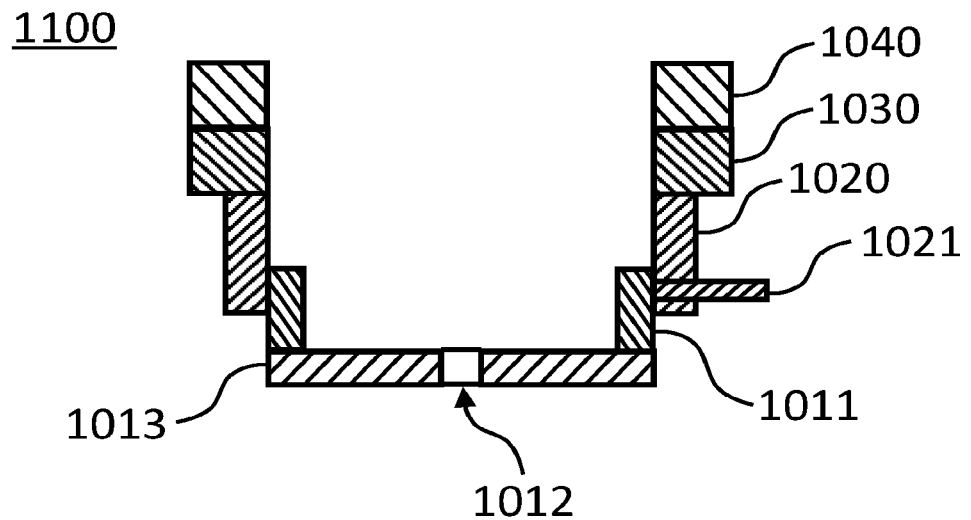
FIG. 10B is a schematic cross-sectional view of an example liquid discharging head according to a seventh embodiment.

FIG. 10A is a schematic top view of an example liquid discharging head according to the seventh embodiment. FIG. 10B is a schematic cross-sectional view of an example liquid discharging head according to the seventh embodiment.

As illustrated in FIG. 10A and FIG. 10B, in the seventh embodiment, in the liquid discharging head 1100, a discharging port (nozzle) 1012 is formed in the center of a membranous member 1013 having a circular planar shape, and a cylindrical liquid containing chamber 1011 capable of containing the liquid to be provided on the membranous member 1013 is provided on the perimeter of the membranous member 1013. Further, in the seventh embodiment, a coupling member 1020 configured to couple the liquid containing chamber 1011 and a piezoelectric element 1030 as a displacement member to each other is provided, and the coupling member 1020 couples the liquid containing chamber 1011 in a manner that the liquid containing chamber 1011 is mountable and demountable, by biasing the liquid containing chamber 1011 by means of a spring 1021 as a demounting member.

The seventh embodiment may be the same as the sixth embodiment in any other respects than including the liquid containing chamber 1011 and the coupling member 1020.

In the seventh embodiment, because a cylindrical liquid containing chamber 1011 capable of containing the liquid to be provided on the membranous member 1013 is provided, the liquid can be provided in a greater amount on the membranous member 1013. Therefore, the liquid discharging head 1100 can contain the liquid by a predetermined thickness above the membranous member 1013 and stabilize the water pressure of the liquid above the membranous member 1013 when discharging the liquid through the discharging port 1012, to enable more stable discharging of the liquid. Further, with the liquid containing chamber 1011, the liquid discharging head 1100 can provide the liquid in a greater amount above the membranous member 1013. This makes it possible to reduce the number of times of supplying the liquid into the liquid discharging head 1100 and discharge more liquid droplets in a shorter time.

The liquid containing chamber 1011 is opened at the top (i.e., has a ventilation port), to allow a gas to circulate. Hence, the atmospheric pressure inside the liquid containing chamber 1011 becomes approximately the same as the atmospheric pressure (typically, standard atmosphere) outside the liquid containing chamber 1011. This makes it possible to discharge the liquid contained in the liquid containing chamber 1011 stably by suppressing the inside of the liquid containing chamber 1011 from being a negative pressure.

In the seventh embodiment, as described above, because the coupling member 1020 configured to couple the liquid containing chamber 1011 and the piezoelectric element 1030 as a displacement member to each other is provided, it is possible to better improve the latitude in selection of the shape and disposition of the liquid discharging head 1100, and make it easier to dispose many liquid discharging heads 1100 side by side.

Further, with the coupling member 1020 coupling the liquid containing chamber 1011 in a manner that the liquid containing chamber 1011 is mountable and demountable by biasing the liquid containing chamber 1011 by means of the spring 1021 as the demounting member, it is possible to perform replacement of the membranous member 1013 and the liquid containing chamber 1011, making it possible to suppress contamination of liquids, when liquids to be discharged are changed.

In this way, in the seventh embodiment, the piezoelectric element 1030 as an example of the displacement member is disposed at the side at which the liquid to be discharged through the discharging port 1012 is provided. This may be an example of the first aspect described above. Further, the coupling member 1020 configured to couple the membranous member 1013 and the displacement member 1030 to each other in a manner that the membranous member 1013 is mountable and demountable via the liquid containing chamber 1011 is provided. This may be an example of the third aspect described above.

Eighth Embodiment

Figure 11A:
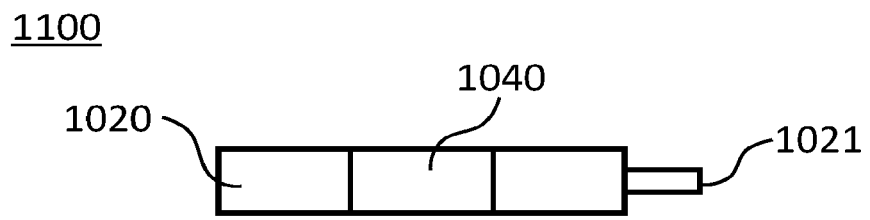
FIG. 11A is a schematic top view of an example liquid discharging head according to an eighth embodiment.
Figure 11B:
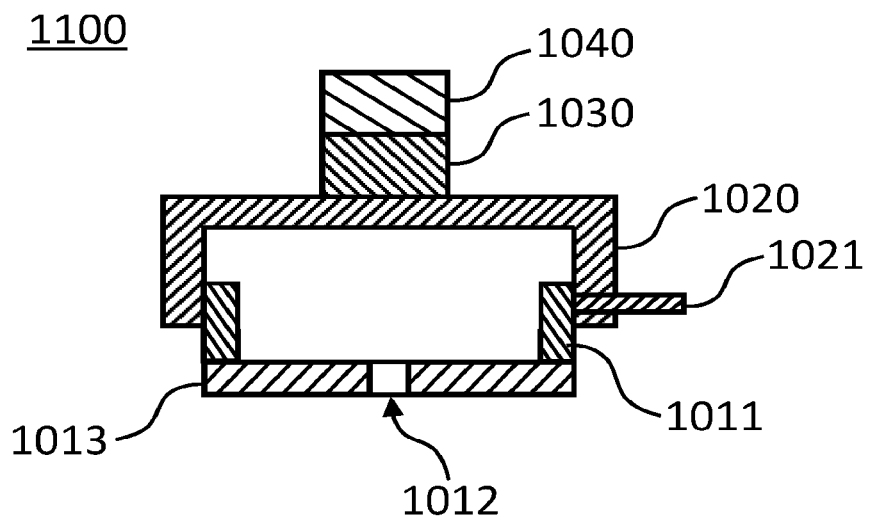
FIG. 11B is a schematic cross-sectional view of an example liquid discharging head according to an eighth embodiment.

FIG. 11A is a schematic top view of an example liquid discharging head according to the eighth embodiment. FIG. 11B is a schematic cross-sectional view of an example liquid discharging head according to the eighth embodiment.

As illustrated in FIG. 11A and FIG. 11B, the eighth embodiment is different from the seventh embodiment in the shape of each member. The eighth embodiment may be the same as the seventh embodiment in any other respects that the shape of each member.

In the eighth embodiment, the membranous member 1013 has a rectangular planar shape, and a liquid containing chamber 1011 is provided on the perimeter of the membranous member 1013. Further, the displacement member 1030 is provided at the center of a coupling member 1020, which is configured to couple the membranous member 1013 and the displacement member 1030 to each other in a manner that the membranous member 1013 is mountable and demountable via the liquid containing chamber 1011. A securing member 1040 is provided on the displacement member 1030.

In the eighth embodiment, because each member such as the membranous member 1013 has a rectangular shape, for example, it is possible to make the liquid discharging head 1100 smaller in size than in the seventh embodiment.

In this way, in the eighth embodiment, the piezoelectric element 1030 as an example of the displacement member is disposed at the side at which the liquid to be discharged through the discharging port 1012 is provided. This may be an example of the first aspect described above. Further, the coupling member 1020 configured to couple the membranous member 1013 and the displacement member 1030 to each other in a manner that the membranous member 1013 is mountable and demountable via the liquid containing chamber 1011 is provided. This may be an example of the third aspect described above.

Ninth Embodiment

Figure 12A:
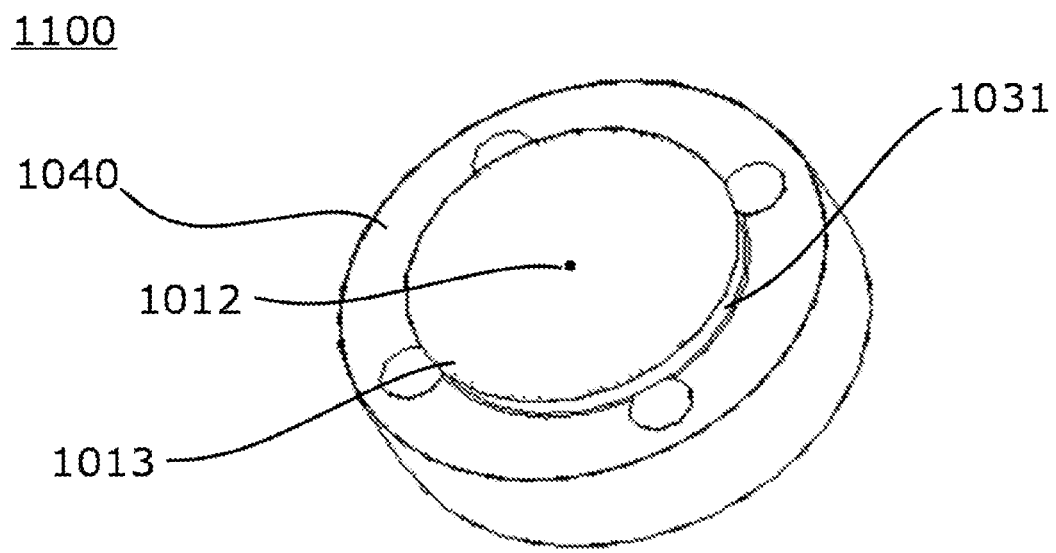
FIG. 12A is a perspective view of an example liquid discharging head according to a ninth embodiment when seen from a discharging surface side of a membranous member.
Figure 12B:
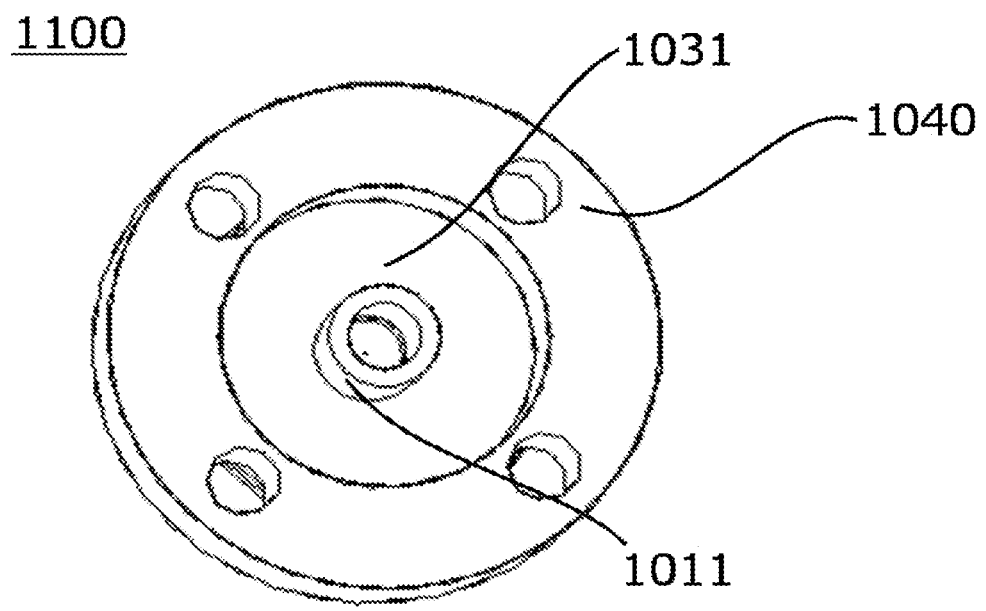
FIG. 12B is a perspective view of an example liquid discharging head according to a ninth embodiment when seen from membranous member's one side at which a liquid is provided (from a side of a membranous member toward a liquid containing chamber)

FIG. 12A is a perspective view of an example liquid discharging head according to the ninth embodiment when seen from a discharging surface side of a membranous member. FIG. 12B is a perspective view of an example liquid discharging head according to the ninth embodiment when seen from membranous member's one side at which the liquid is provided (from a side of the membranous member toward a liquid containing chamber).

As illustrated in FIG. 12A and FIG. 12B, in the ninth embodiment, a piezoelectric element 1031 of a shear mode (bimorph type) as an example of a displacement member contacts a liquid containing chamber 1011, a membranous member 1013, and a securing member 1040. In the ninth embodiment, the liquid can be retained by the internal side surface of the piezoelectric element 1031 and by the liquid containing chamber 1011.

Figure 13:
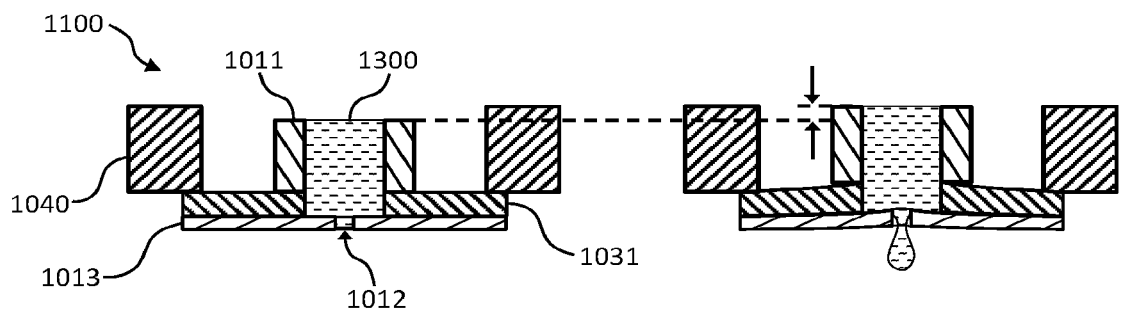
FIG. 13 is a schematic cross-sectional view illustrating an example operation of an example liquid discharging head according to a ninth embodiment when discharging a liquid through a discharging port.

FIG. 13 is a schematic cross-sectional view illustrating an example operation of the example liquid discharging head according to the ninth embodiment when discharging a liquid through a discharging port.

In the ninth embodiment, the shear mode piezoelectric element 1031 is deformed (bent), to displace the position of the liquid containing chamber 1011. Along with this displacement, a portion near the discharging port 1012 of the membranous member 1013 is deformed, to displace the position of the discharging port. In this way, the position of the liquid containing chamber 1011 and the position of the discharging port 1012 in the membranous member 1013 are displaced, to cause a liquid droplet to be discharged through the discharging port 1012. More specifically, in the ninth embodiment, the position of the liquid containing chamber 1011 and the position of the discharging port 1012 in the membranous member 1013 are reciprocated by the shear mode piezoelectric element 1031 in a direction in which a liquid droplet is to be discharged (discharging direction), to cause a liquid droplet to be discharged through the discharging port 1012.

In the ninth embodiment, use of the thin shear mode piezoelectric element 1031 can make the liquid discharging head 1100 thinner, making it possible to reduce the size of the liquid discharging head 1100.

Further, in the ninth embodiment, selection of a material that has a high stiffness and does not easily deform as the material of the securing member 1040 can suppress loss of displacing energy of the displacement member 1031, making it possible to displace the position of the membranous member 1013 efficiently and cause the liquid to be discharged through the discharging port 1012 more efficiently.

In this way, in the ninth embodiment, the piezoelectric element 1031 as an example of the displacement member is disposed at the side at which the liquid to be discharged through the discharging port 1012 is provided. This may be an example of the first aspect described above.

Tenth Embodiment

Figure 14:
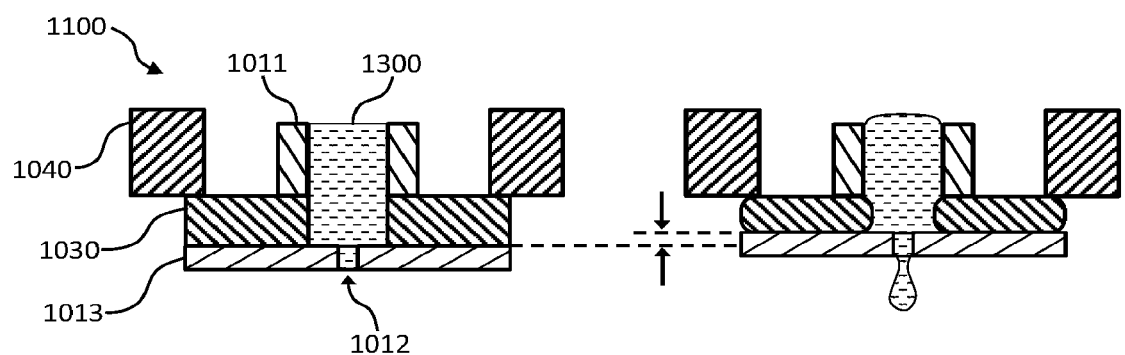
FIG. 14 is a schematic cross-sectional view illustrating an example operation of an example liquid discharging head according to a tenth embodiment when discharging a liquid through a discharging port.

FIG. 14 is a schematic cross-sectional view illustrating an example operation of an example liquid discharging head according to the tenth embodiment when discharging a liquid through a discharging port.

In the tenth embodiment, a longitudinal mode piezoelectric element 1030 is elongated and contracted, to displace the position of the whole membranous member 1013. Here, the position of the liquid containing chamber 1011 is not displaced. In this way, in the tenth embodiment, the longitudinal mode piezoelectric element 1030 is used to displace the position of the membranous member 1013, to cause a liquid droplet to be discharged through the discharging port 1012. More specifically, in the tenth embodiment, the position of the membranous member 1013 is reciprocated by the longitudinal mode piezoelectric element 1030 in a direction in which a liquid droplet is to be discharged (discharging direction), to cause a liquid droplet to be discharged through the discharging port 1012.

In the tenth embodiment, use of the longitudinal mode piezoelectric element 1030 that can be made small in the width (the size in the horizontal direction) can make the width of the liquid discharging head 1100 smaller, making it possible to reduce the size of the liquid discharging head 1100.

Further, in the tenth embodiment, selection of a material that has a high stiffness and does not easily deform as the material of the securing member 1040 can suppress loss of displacing energy of the displacement member 1030, making it possible to displace the position of the membranous member 1013 efficiently and cause the liquid to be discharged through the discharging port 1012 more efficiently.

In this way, in the tenth embodiment, the piezoelectric element 1030 as an example of the displacement member is disposed at the side at which the liquid to be discharged through the discharging port 1012 is provided. This may be an example of the first aspect described above.

Eleventh Embodiment

Figure 15A:
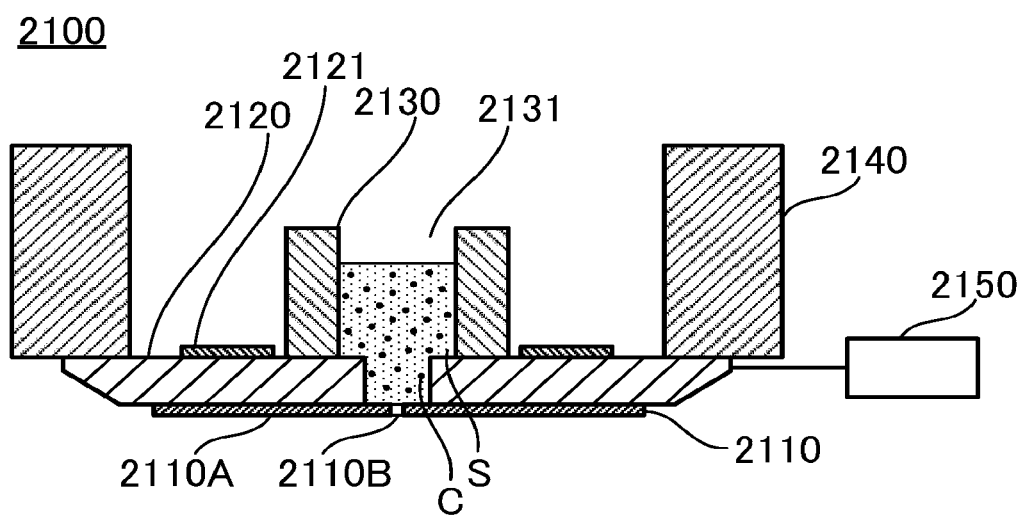
FIG. 15A is a schematic view illustrating a liquid discharging head according to an eleventh embodiment.

FIG. 15A is a schematic view illustrating a liquid discharging head according to the eleventh embodiment.

As illustrated in FIG. 15A, a liquid discharging head 2100 includes a membranous member 2110, a piezoelectric element 2120 as a displacement member, a liquid containing container 2130 as a contact shielding unit (liquid containing chamber), a housing 2140, and a head driving unit 2150. FIG. 15A illustrates a state of a cell suspension S as the liquid being contained by the membranous member 2110, the piezoelectric element 2120, and the liquid containing container 2130. The cell suspension S contains cells C.

In the present embodiment, as a matter of convenience for description, when the piezoelectric element 2120 is seen as a reference, a side toward the liquid containing container 2130 is referred to as upper side, and a side toward the membranous member 2110 is referred to as lower side. Further, when the piezoelectric element 2120 is seen as a reference, a surface at the side toward the liquid containing container 2130 is referred to as upper surface, and a surface at the side toward the membranous member 2110 is referred to as lower surface.

In the present embodiment, the membranous member 2110 is secured on the lower surface of the piezoelectric element 2120.

In the present embodiment, the membranous member 2110 has a flat plate shape and an approximately true-circular planar shape.

In the present embodiment, in the structure of the membranous member 2110, a discharging port 2110E is formed in the center of the approximately true-circular shape when seen in a plan view perspective.

The details of the discharging port 2110B will be described below.

In the present embodiment, the membranous member 2110 has a size of ϕ20 mm and an average thickness of 0.05 mm.

In the present embodiment, the material of the membranous member 2110 is stainless steel.

The discharging surface 2110A is a discharging side surface of the membranous member 2110 for discharging the cell suspension S. In the present embodiment, the discharging surface 2110A is the lower surface of the membranous member 2110.

The discharging port 2110B is a port (hole) through which the cell suspension S contained in the liquid containing container 2130 is contained is discharged. In the present embodiment, the discharging port 2110B is formed as a through hole penetrating the membranous member 2110 from the upper surface to the lower surface.

In the present embodiment, the shape of the opening of the discharging port 2110B is a true-circular shape.

In the present embodiment, the discharging port 2110B has a diameter of ϕ0.08 mm.

The piezoelectric element 2120 is formed at a side at which the cell suspension S to be discharged through the discharging port 2110B is contained, i.e., the upper surface side of the membranous member 2110.

In the present embodiment, the piezoelectric element 2120 includes an electrode 2121 through which a voltage is applied. When a voltage is applied to the electrode 2121, a shrinkage stress is generated in the lateral direction of FIG. 15A due to an inverse piezoelectric effect. As a result, the piezoelectric element 2120 can bend the membranous member 2110 disposed on the lower surface of the piezoelectric element 2120 and displace the position of the discharging port 2110B, to cause the cell suspension S to be discharged through the discharging port 2110B.

In the present embodiment, because the membranous member 2110 has an approximately true-circular planar shape and the discharging port 2110B is present in approximately the center of the approximately true-circular planar shape, the planar shape of the piezoelectric element 2120 is an annular (ring-like) shape in order to be capable of displacing the position of the discharging port 2110B.

In the present embodiment, the structure of the piezoelectric element 2120 includes an electrode 2121 (electrification unit) through which a voltage is applied to the piezoelectric material.

In the present embodiment, the piezoelectric element 2120 has an outer diameter of ϕ20 m and an inner diameter of ϕ4 mm.

In the present embodiment, the material of the piezoelectric element 2120 is lead titanate zirconate (PZT).

In the present embodiment, the liquid containing container (liquid containing chamber) 2130 can contain the cell suspension S, and is configured to shield the electrode 2121 of the piezoelectric element 2120 from being contacted by the cell suspension S. At the top, the liquid containing container 2130 has an atmospherically exposed portion 2131 for exposing the inside of the liquid containing container 2130 to the atmosphere, and can evacuate bubbles mixed in the cell suspension S through the atmospherically exposed portion 2131.

In the present embodiment, the shape and structure of the liquid containing container 2130 are cylindrical.

In the present embodiment, the liquid containing container 2130 has an inner diameter of ϕ4 mm, an outer diameter of ϕ6 mm, and a height of 10 mm.

In the present embodiment, the material of the liquid containing container 2130 is polycarbonate.

In the present embodiment, the material of the liquid containing container is polycarbonate. This is non-limiting. The material of the liquid containing container may be, for example, any of metals, resins, silicones, and ceramics.

In the present embodiment, the amount of the cell suspension S contained in the liquid containing container 2130 is 120 microliters.

In the present embodiment, the amount of the cell suspension contained in the liquid containing container is set to 120 microliters. However, this is non-limiting. For example, the amount of the cell suspension contained may be, for example 1 microliter or greater but 1 mL or less. Particularly, when using an expensive liquid such as a cell suspension, the amount of the cell suspension contained is preferably 1 microliter or greater but 200 microliters or less because it is preferable to be capable of discharging a liquid in a small amount.

In the present embodiment, a liquid containing container is used as the contact shielding unit. However, this is non-limiting. For example, the contact shielding unit may be a coating film for coating the electrode of the piezoelectric element. In this case, a liquid containing container is not needed.

In the present embodiment, the housing 2140 has a cylindrical shape and accommodates the liquid containing container 2130. The perimeter of the piezoelectric element 2120 is secured to the lower end portions of the housing 2140, i.e., the lower surface of the housing 2140.

In the present embodiment, the head driving nit 2150 is configured to input a discharging signal to the piezoelectric element 2120 to drive the piezoelectric element 2120.

<Cell Suspension (Liquid)>

In the present embodiment, the liquid to be discharged through the discharging port 2110B is the cell suspension S. The cells C contained in the cell suspension S are human-derived cells. Hence, the liquid discharging head 2100 can form a tissue for evaluation of medical efficacy or cosmetics.

In the present embodiment, the solvent of the cell suspension S is water. However, this is non-limiting.

[Liquid Discharging Operation of Liquid Discharging Head According to Eleventh Embodiment]

Figure 15B:
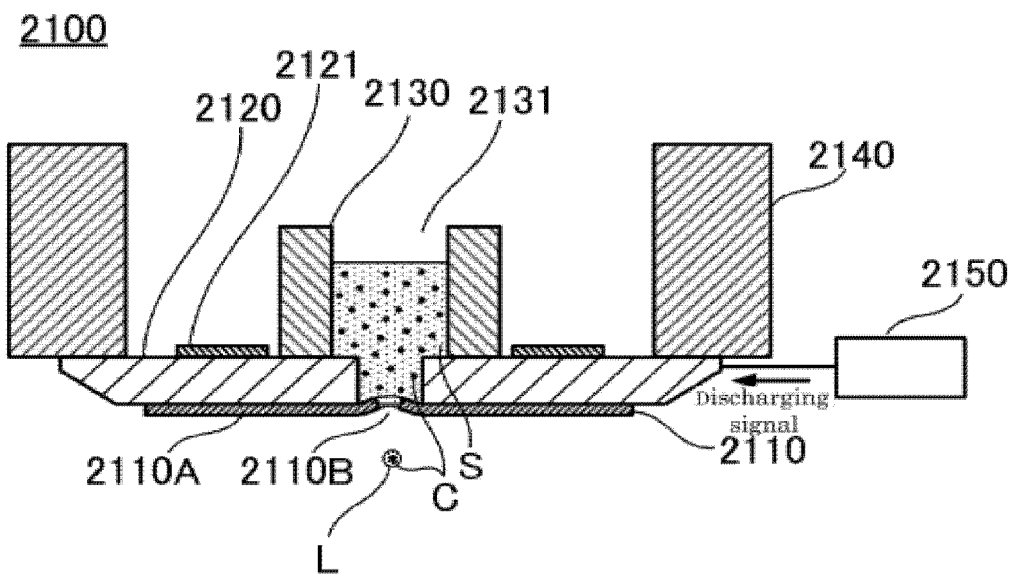
FIG. 15B is a view illustrating an operation of a liquid discharging head illustrated in FIG. 15A when discharging a liquid.

FIG. 15B is a view illustrating an operation of the liquid discharging head illustrated in FIG. 15A for discharging a liquid.

As illustrated in FIG. 15B, the head driving unit 2150 inputs a discharging signal to the piezoelectric element 2120, and the piezoelectric element 2120 contracts to bend the membranous member 2110. As a result, the position of the discharging port 2110B is displaced, to cause the cell suspension S in the liquid containing container 2130 to be discharged in the form of a liquid droplet L containing a cell C.

Next, the simple structure of the liquid discharging head of the present disclosure facilitating cleaning of the discharging port will be described, taking for example, a liquid discharging apparatus including the liquid discharging head of the present disclosure and a cleaning device configured to clean the liquid discharging head.

Figure 16A:
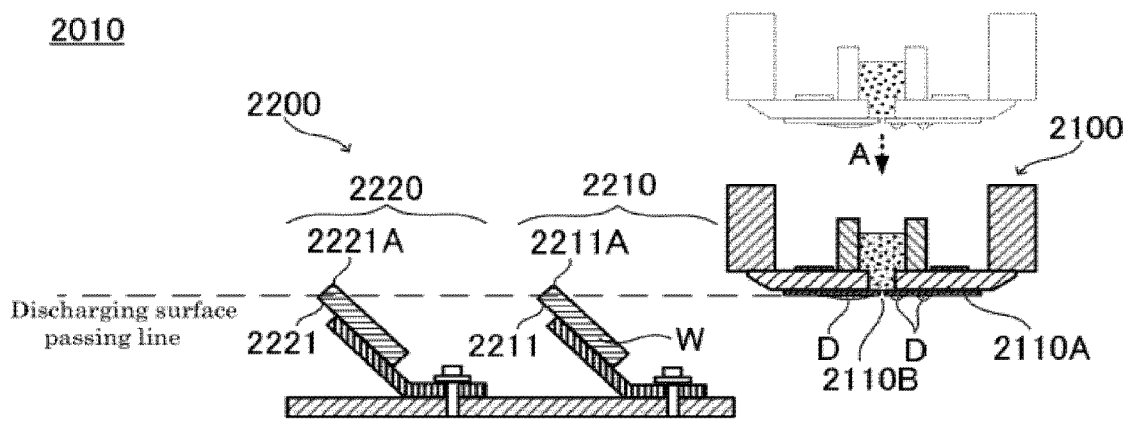
FIG. 16A is a view illustrating an operation of a liquid discharging apparatus according to an eleventh embodiment when cleaning a discharging surface of a liquid discharging head.
Figure 16B:
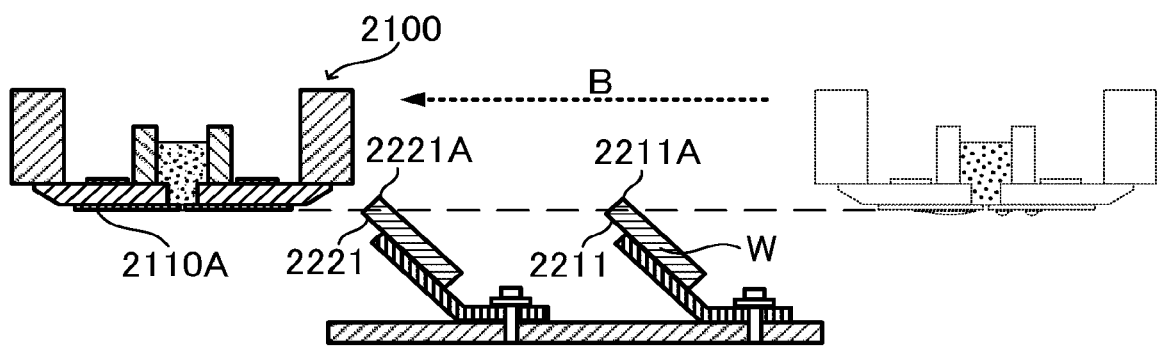
FIG. 16B is a view illustrating an operation of a liquid discharging apparatus according to an eleventh embodiment when cleaning a discharging surface of a liquid discharging head.

FIG. 16A and FIG. 16B are views illustrating an operation of a liquid discharging apparatus according to the eleventh embodiment when cleaning a discharging surface of the liquid discharging head.

As illustrated in FIG. 16A, the liquid discharging apparatus 2010 includes a liquid discharging head 2100 having a discharging surface 2110A to which stains D adhere, and a cleaning device 2200 configured to clean the discharging surface 2110A of the liquid discharging head 2100.

The liquid discharging head 2100 may have troubles such as variation of the discharging direction of the liquid to be discharged through the discharging port 2110B and liquid discharging failures, when stains D of, for example, the cell suspension S adhere to the portion near the discharging port 2110B of the discharging surface 2110A. In order for the discharging surface 2110A to be cleaned so as to prevent such troubles, first, the liquid discharging head 2100 is moved by the driving unit in the vertical direction indicated by an arrow A of FIG. 16A. Here, the height of the discharging surface 2110A is adjusted to a discharging surface passing line on which the discharging surface 2110A will contact an end 2211A of a first contacting member 2211 and an end 2221A of a second contacting member 2221.

Next, as illustrated in FIG. 16B, the liquid discharging head 2100 with the height-adjusted discharging surface 2110A is moved by the driving unit in the horizontal direction indicated by an arrow B of FIG. 16B. Then, the discharging surface 2110A first comes into contact with the first contacting member 2211, and the stains D that are made easily releasable by the effect of a wetting liquid W contained in the first contacting member 2211 are wiped off by the end 2211A of the first contacting member 2211 by the time when the liquid discharging head 2100 completely passes by.

Next, after the stains D on the discharging surface 2110A are wiped off, the discharging surface 2110A subsequently comes into contact with the end 2221A of the second contacting member 2221. Then, minute liquid droplets of the wetting liquid W having failed to be wiped by the first contacting member 2211 to remain on the discharging surface 2110A are adsorbed by the second contacting member 2221 including the end 2221A.

In this way, the liquid discharging apparatus 2010 can have the stains D, which adhere to the discharging surface 2110A of the liquid discharging head 2100, easily cleaned by the cleaning device 2200.

In this way, in the eleventh embodiment, the piezoelectric element 2120 as an example of the displacement member is disposed at the side at which the liquid to be discharged through the discharging port 2110B is provided. This may be an example of the first aspect described above.

Twelfth Embodiment

Figure 17:
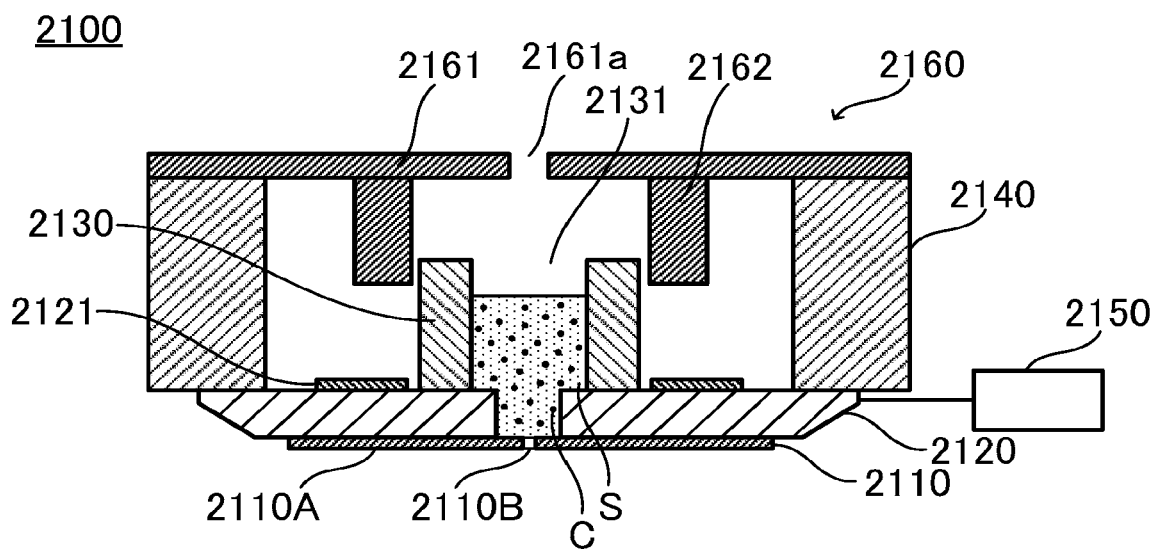
FIG. 17 is a schematic view illustrating a liquid discharging head according to a twelfth embodiment.

FIG. 17 is a schematic view illustrating a liquid discharging head according to the twelfth embodiment.

As illustrated in FIG. 17, in the twelfth embodiment, the liquid discharging head 2100 according to the eleventh embodiment is further provided with a cover 2160 for preventing evaporation of the cell suspension contained in the liquid containing chamber 2130. In other words, the liquid discharging head 2100 of the twelfth embodiment is an embodiment obtained by further providing the liquid discharging head 2100 of the eleventh embodiment with a cover 2160 disposed in a manner to cover the cell suspension contained (in a manner to face the membranous member at the membranous member's one side at which the liquid is provided).

In the present embodiment, the cover 2160 includes a flat plate member 2161 and a cylindrical member 2162.

In the present embodiment, the flat plate member 2161 has a circular planar shape and the same outer diameter as the housing 2140, and can cover the opening of the housing 2140. A through hole 2161a is provided in the center of the flat plate member 2161 so as not to tightly seal the inside of the housing 2140 and disturb discharging of the liquid through the discharging port.

In the present embodiment, the cylindrical member 2162 has a cylindrical shape. The cylindrical member 2162 has an inner diameter slightly greater than the outer diameter of the liquid containing container 2130 and is secured to the lower surface of the flat plate member 2161 at a position at which the cover 2160 surrounds the top portion of the liquid containing container 2130 when the cover 2160 is mounted.

Therefore, the inner space of the cylindrical member 2162 relatively narrower than the inner space of the housing 2140 is easily saturated with a gas of the cell suspension S when the cell suspension S is evaporated from the upper surface of the liquid containing container 2130. This make is possible to suppress the amount of the cell suspension S to be evaporated.

Figure 18:
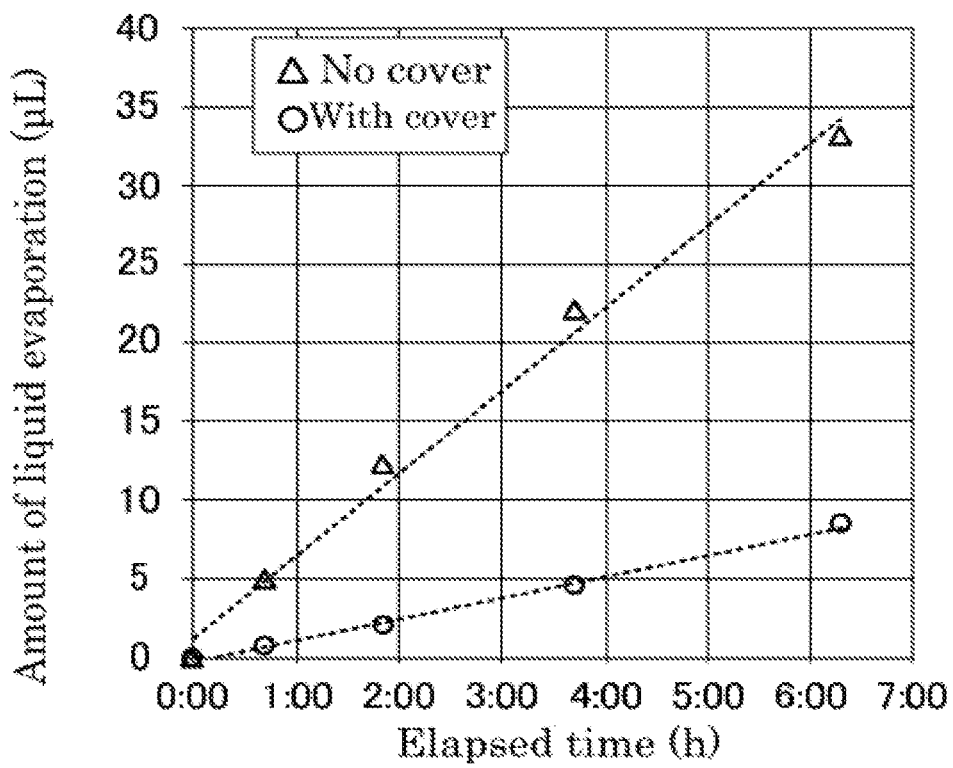
FIG. 18 is a graph plotting comparison of the amounts of temporal liquid evaporation of the liquid contained in a liquid discharging head depending on presence or absence of a cover on the liquid discharging head.

FIG. 18 is a graph plotting comparison of the amounts of temporal liquid evaporation of the liquid contained in the liquid discharging head depending on presence or absence of the cover on the liquid discharging head.

As plotted in FIG. 18, it can be seen that the amount of temporal liquid evaporation of the liquid contained in the liquid discharging head when the cover 2160 is provided is lower than the amount of temporal liquid evaporation when the cover 2160 is not provided. Specifically, the amount of temporal liquid evaporation when the cover 2160 is provided is about one third of the amount of temporal liquid evaporation when the cover 2160 is not provided.

In this way, the liquid discharging head of the twelfth embodiment obtained by further providing the liquid discharging head of the eleventh embodiment with a cover can suppress the amount of temporal liquid evaporation of the liquid contained in the liquid discharging head.

In this way, in the twelfth embodiment, the piezoelectric element 2120 as an example of the displacement member is disposed at the side at which the liquid to be discharged through the discharging port 2110B is provided. This may be an example of the first aspect described above.

Thirteenth Embodiment

Figure 19:
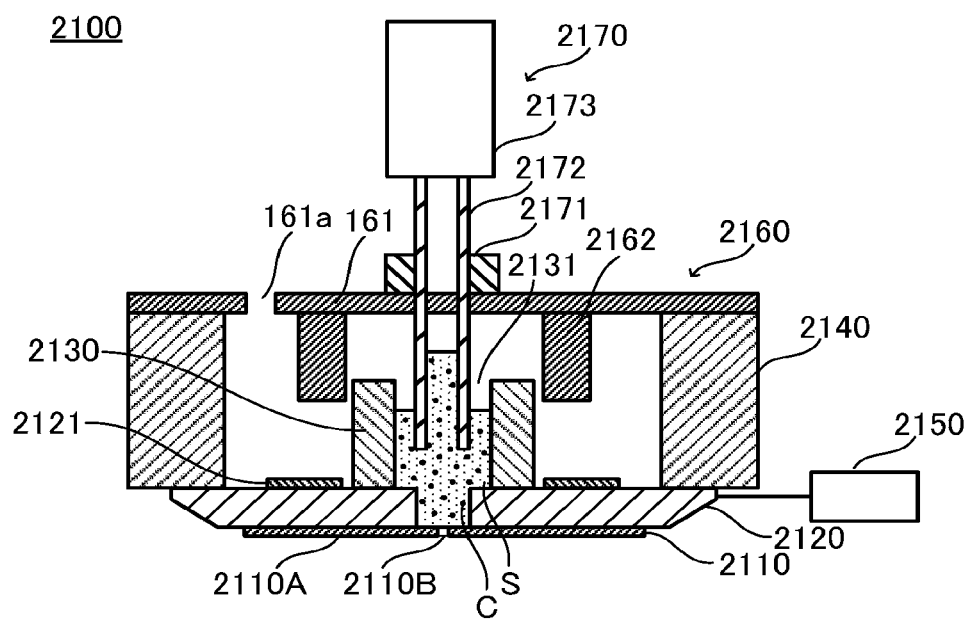
FIG. 19 is a schematic view illustrating a liquid discharging head according to a thirteenth embodiment.

FIG. 19 is a schematic view illustrating a liquid discharging head according to the thirteenth embodiment.

As illustrated in FIG. 19, in the thirteenth embodiment, the liquid discharging head 2100 of the twelfth embodiment is further provided with a stirring member 2170 configured to stir the cell suspension S contained in the liquid containing container 2130. In other words, the liquid discharging head 2100 of the thirteenth embodiment is an embodiment obtained by further providing the liquid discharging head 2100 of the twelfth embodiment with a stirring member attached on the cover 2160 and configured to stir the contained cell suspension S by conveying the cell suspension S.

In the liquid discharging head 2100 of the thirteenth embodiment, along with the installation of the stirring member 2170, the through hole 2161a is repositioned from the center of the cover 2160 to a position that is within the inner diameter of the housing 2140 and beyond the outer diameter of the cylindrical member 2162.

In the present embodiment, the stirring member 2170 includes a cylindrical member 2172, a locking member 2171, and a pump 2173.

In the present embodiment, the cylindrical member 2172 has an elongate cylindrical shape and is locked to the cover 2160 by the locking member 2171. One end of the cylindrical member 2172 is immersed in the cell suspension S contained in the liquid containing container 2130 so as not to contact the membranous member 2110. The other end of the cylindrical member 2172 is coupled to the pump 2173.

The stirring member 2170 can convey and stir the cell suspension contained in the liquid containing container 2130 by a sucking operation and an ejecting operation of the pump 2173. This makes it possible to disperse precipitated cells C and suppress the discharging port 2110B from being clogged with cells C when cells C are discharged.

The stirring member 2170 not only may convey the cell suspension S but also may supply the cell suspension S by the pump 2173. Hence, when the amount of the cell suspension S contained in the liquid containing container 2130 has become low through repeated discharging of the cell suspension S, the liquid discharging head 2100 can immediately supply the cell suspension S into the liquid containing container 2130.

The cover 2160 locked by the locking member 2171 is disposed at the upper end of the housing 2140 and the lower end of the housing 2140 is disposed at a region of the piezoelectric element 2120 not to be bent. Therefore, the stirring member 2170 is lowly susceptible to mechanical motions of the piezoelectric element 2120 during discharging.

In this way, the liquid discharging head of the thirteenth embodiment obtained by further providing the liquid discharging head of the twelfth embodiment with a stirring member can stir the cells precipitated in the cell suspension contained in the liquid containing container. Hence, the liquid discharging head of the thirteenth embodiment can suppress aggregation of cells and clogging of the discharging port with cells.

In this way, in the thirteenth embodiment, the piezoelectric element 2120 as an example of the displacement member is disposed at the side at which the liquid to be discharged through the discharging port 2110B is provided. This may be an example of the first aspect described above.

Fourteenth Embodiment

Figure 20:
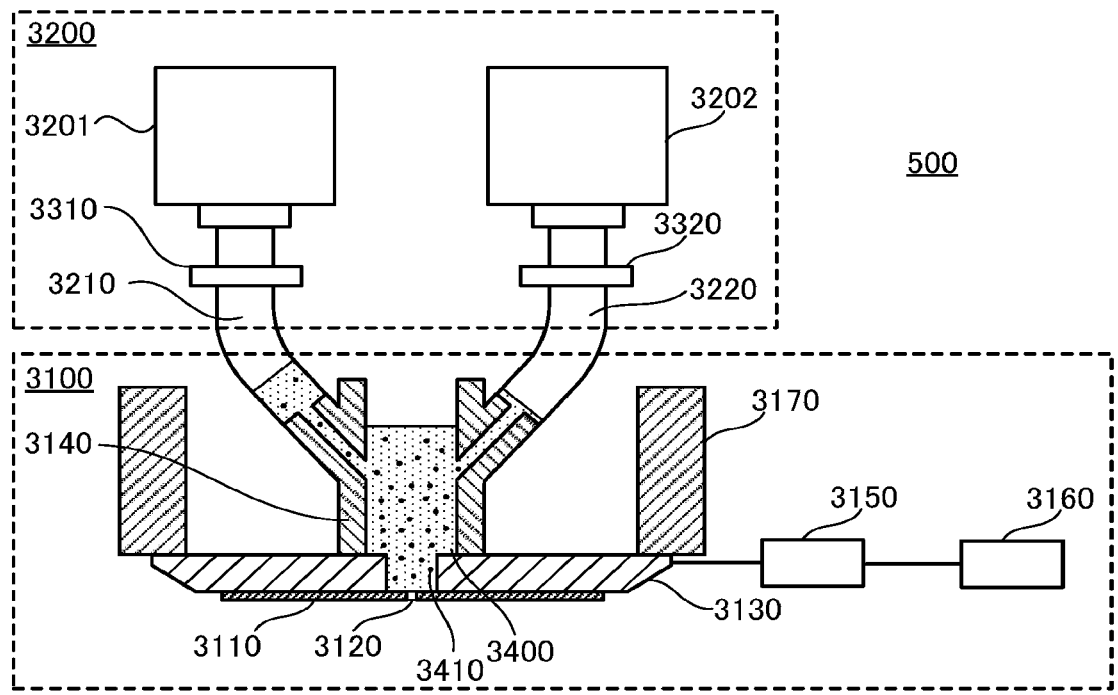
FIG. 20 is a schematic view illustrating an example liquid discharging apparatus according to a fourteenth embodiment.

FIG. 20 is a schematic view illustrating an example liquid discharging apparatus according to the fourteenth embodiment.

As illustrated in FIG. 20, the liquid discharging apparatus 3500 includes a liquid discharging head 3100 and a liquid containing chamber stirring unit 3200.

The liquid discharging head 3100 includes a liquid discharging unit including: a nozzle plate (membranous member) 3110 in which a discharging port 3120 is formed; a vibration member 3130 as a displacement unit (displacement member); a liquid containing chamber 3140; a driving unit 3150 configured to drive the vibration member 3130; a control unit 3160; and a housing 3170.

The liquid containing chamber stirring unit 3200 includes a first liquid delivering unit 3201, a second liquid delivering unit 3202, a flow path 3210 linking the first liquid delivering unit 3201 to the liquid containing chamber 3140, and a flow path 3220 linking the second liquid delivering unit 3202 to the liquid containing chamber 3140. The flow path 3210 is provided with a water stop valve 3310 and the flow path 3220 is provided with a water stop valve 3320.

The first liquid delivering unit 3201 and the second liquid delivering unit 3202 function as a pair of liquid delivering units. The flow path 3210 and the flow path 3220 function as a pair of liquid reservoirs. The water stop valve 3310 and the water stop valve 3320 function as a pair of opening/closing units.

FIG. 20 exemplarily illustrates a state that a solution 3400 containing particles 3410 is retained in the liquid containing chamber 3140.

In the present embodiment, as a matter of convenience for description, when the vibration member 3130 is seen as a reference, a side toward the liquid containing chamber 3140 is referred to as upper side, and a side toward the nozzle plate 3110 is referred to as lower side. Further, a surface of each member at the side toward the liquid containing chamber 3140 is referred to as upper surface, and a surface of each member at the side toward the nozzle plate 3110 is referred to as lower surface.

A plan view perspective means that a target is seen from above or below the target. A planar shape means the shape of a target seen from above or below the target.

The liquid containing chamber 3140 retains a solution 3400 containing particles 3410 (particles 3410 being dispersed).

The top of the liquid containing chamber 3140 is exposed to the atmosphere, to evacuate bubbles mixed in the solution 3400 to the atmosphere.

Examples of the material of the liquid containing chamber 3140 include metals, resins, silicone, and ceramics.

The nozzle plate (membranous member) 3110 is secured to the lower end of the liquid containing chamber 3140 via the vibration member 3130.

A discharging port (nozzle) 3120, which is a through hole, is formed in approximately the center of the nozzle plate 3110. The solution 3400 retained in the liquid containing chamber 3140 is discharged through the nozzle 3120 in the form of a liquid droplet in response to vibration of the nozzle plate 3110.

The planar shape of the nozzle plate 3110 may be, for example, a circular shape, but may be an elliptic shape or a quadrangular shape.

In the present embodiment, the material of the nozzle plate 3110 is stainless steel.

It is preferable that the discharging port (nozzle) 3120 be formed as a substantially true-circular through hole in approximately the center of the nozzle plate 3110. In this case, the diameter of the nozzle 3120 is not particularly limited, may be appropriately selected depending on the intended purpose, and is preferably two or more times greater than the size of the particle 3410 in order to avoid clogging the nozzle 3120 with the particle 3410.

The vibration member 3130 as the displacement member is formed on the upper surface side of the nozzle plate 3110. That is, the vibration member 3130 is disposed at the side of the nozzle plate 3110 toward the liquid containing chamber 3140 in which the solution 3400 to be discharged through the discharging port 3120 is retained.

The shape of the vibration member 3130 can be designed to match the shape of the nozzle plate 3110. For example, when the planar shape of the nozzle plate 3110 is a circular shape, it is preferable to form the vibration member 3130 having an annular (ring-like) planar shape to surround the nozzle 3120.

The vibration member 3130 is, for example, a piezoelectric element obtained by providing the upper surface and the lower surface of a piezoelectric material with electrodes across which a voltage is to be applied. When a voltage is applied across the upper and lower electrodes of the vibration member 3130, a compressive stress is applied in the lateral direction of a sheet of paper, making it possible for the nozzle plate 3110 to vibrate.

The driving unit 3150 is configured to drive the vibration member 3130. The driving unit 3150 can apply to the vibration member 3130, a discharging waveform (discharging signal) for vibrating the nozzle plate 3110 to form liquid droplets.

That is, by applying the discharging waveform to the vibration member 3130 and controlling the vibration state of the nozzle plate 3110, the driving unit 3150 can cause the solution 3400 retained in the liquid containing chamber 3140 to be discharged through the nozzle 3120 in the form of a liquid droplet.

Examples of the particles 3410 in the solution 3400 containing the particles 3410 include metallic particles, inorganic particles, and cells.

Among these particles, cells are preferable.

Water is the most common as the solvent of the solution 3400. However, the solvent is not limited to water, but various organic solvents such as alcohols, mineral oils, and vegetable oils may be used.

The amount of the solution 3400 retained in the liquid containing chamber 3140 is not particularly limited, may be appropriately selected depending on the intended purpose, and is preferably 1 microliter or greater but 1 milliliter or less. Particularly, when using an expensive liquid such as a cell suspension, the amount of the solution 3400 retained is more preferably 1 microliter or greater but 200 microliters or less in terms of forming liquid droplets with a small liquid amount.

The first liquid delivering unit 3201 and the second liquid delivering unit 3202 as a pair of liquid delivering units are coupled to the flow path 3210 and the flow path 3220 respectively, and configured to convey the solution 3400 from the flow path 3210 and flow path 3220 to the liquid containing chamber 3140 and vice versa.

It is preferable that conveying of the solution 3400 by the first liquid delivering unit 3201 and the second liquid delivering unit 3202 be performed by making an outflow of the solution 3400 stored in one flow path into the liquid containing chamber 3140 and making an inflow of the solution 3400 into the other flow path from the liquid containing chamber 3140 at the flow rate of the outflow from the one flow path into the liquid containing chamber 3140. This makes it possible for the solution 3400 in the liquid containing chamber 3140 to have a constant liquid surface height. Hence, it is possible to make the liquid pressure constant and stabilize discharging in such a liquid discharging head 3100 as of the present embodiment configured to discharge the solution 3400 by means of the liquid pressure (static pressure) applied to the discharging port 3120 by the solution 3400 contained in the liquid containing chamber 3140 and by means of the motion of displacing the discharging port 3120 (dynamic pressure).

When the amount of the solution 3400 retained in the liquid containing chamber 3140 is lower than a predetermined value, it is preferable that the liquid delivering units make an inflow of the solution 3400 into the liquid containing chamber 3140 from at least any one of the flow paths. Through this supplying of the solution 3400 into the liquid containing chamber 3140, the liquid discharging head 3100 can make the liquid pressure constant and stabilize discharging.

Examples of the first liquid delivering unit 3201 and the second liquid delivering unit 3202 include pumps capable of sucking, retaining and discharging a liquid by a constant amount, such as syringe-type or plunger-type motor pumps.

It is preferable that the flow path 3210 linking the first liquid delivering unit 3201 and the liquid containing chamber 3140 and the flow path 3220 linking the second liquid delivering unit 3202 and the liquid containing chamber 3140 be silicone rubber tubes. The inner diameter and length of the silicone rubber tubes are not particularly limited and may be appropriately selected.

The flow path 3210 and the flow path 3220 as a pair of liquid reservoirs are coupled to the liquid containing chamber 3140 in a manner to be capable of each circulating the solution 3400 into the liquid containing chamber 3140, and can temporarily store the solution 3400.

The flow path 3210 and the flow path 3220 are replaceable, and it is possible to vary the capacity by adjusting the inner diameter and length. These two flow paths are disposed to be inclined with respect to the nozzle 3120 (nozzle plate 3110). That is, these two flow paths are disposed to be inclined with respect to the center axis passing through the nozzle 3120.

As the disposition of the flow path 3210 and the flow path 3220, it is preferable to dispose the flow paths in a manner that an extension line of the center axis of each flow path at the linking portion falls on a corner portion formed by the nozzle plate 3110 and the vibration member 3130, or is slightly off from the corner portion toward the nozzle 3120.

The water stop valve 3310 and the water stop valve 3320 as a pair of opening/closing units are disposed at the flow path between the first liquid delivering unit 3201 and the flow path 3210 and at the flow path between the second liquid delivering unit 3202 and the flow path 3220 respectively, and configured to open and close the respective flow paths.

The control unit 3160 is configured to control the first liquid delivering unit 3201 and the second liquid delivering unit 3202 and the water stop valve 3310 and the water stop valve 3320 in a manner to make the liquid surface height of the solution 3400 retained in the liquid containing chamber 3140 constant.

The control unit 3160 includes, for example, a CPU (Central Processing Unit), a ROM (Read Only Memory), a RAM (Random Access Memory), and a main memory, and is configured to execute various processes based on a control program for controlling the operation of the entire liquid discharging apparatus.

In the present embodiment, the housing 3170 has a cylindrical shape, and accommodates the liquid containing chamber 3140. The circumferential portion of the vibration member 3130 is secured to the lower end, i.e., the lower surface of the housing 3170.

In this way, in the fourteenth embodiment, the vibration member 3130 as an example of the displacement member is disposed at the side at which the liquid to be discharged through the discharging port (nozzle) 3120 is provided. This may be an example of the first aspect described above.

Fifteenth Embodiment

Figure 21:
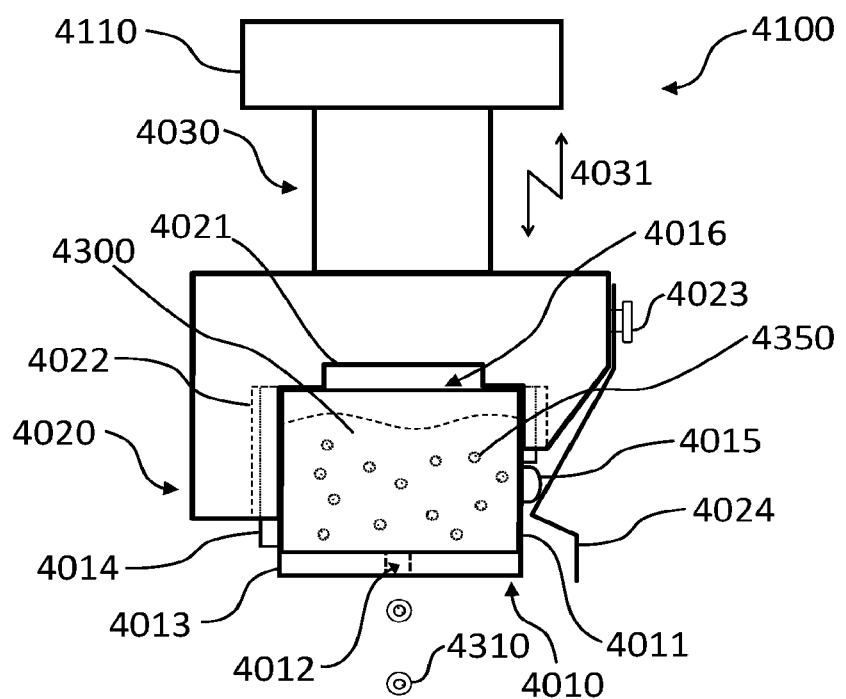
FIG. 21 is a schematic front view illustrating an example liquid discharging head (liquid discharging unit) according to a fifteenth embodiment.

FIG. 21 is a schematic front view illustrating an example liquid discharging head (liquid discharging unit) according to the fifteenth embodiment.

The liquid discharging unit 4100 includes a liquid container 4010, a coupling member 4020, and a piezoelectric element 4030 as a displacement member.

The liquid container 4010 includes a liquid chamber (liquid containing chamber) 4011, a nozzle plate (membranous member) 4013 including a nozzle (discharging port) 4012, a positioning rib 4014, a locking member 4015, and a ventilation port 4016. The nozzle plate (membranous member) 4013 is preferably formed of SUS steel. When the nozzle plate 4013 is formed of SUS steel, there is an advantage in terms of cytotoxicity.

The diameter of the nozzle plate 4013 is not particularly limited, may be appropriately selected depending on the intended purpose, and is about 8 mm in the present embodiment.

The coupling member 4020 includes a ventilation region 4021, a positioning groove 4022, and a leaf spring 4024 secured by a screw 4023.

The piezoelectric element 4030 is bonded to the coupling member 4020 and to the securing unit (securing member) 4110, and vibrates in the direction of an arrow 4031 when a voltage is applied. The ventilation port 4016 of the liquid container 4010 links to the ventilation region 4021 of the coupling member 4020, and a gas can circulate to and from between the inside and the outside of the liquid chamber 4011 of the liquid container 4010. Hence, vibrating the piezoelectric element 4030 can cause the liquid container 4010 and the coupling member 4020 to vibrate and can cause a liquid droplet 4310 of the cell suspension 4300 suspending the cells 4350 to be discharged through the nozzle 4012.

The dimension of the piezoelectric element 4030 is not particularly limited and may be appropriately selected depending on the intended purpose. In the present embodiment, a cubic lead zirconate titanate (PZT) element having a length of about 5 mm on each side is used. Existing liquid discharging heads have employed a columnar (disk-shaped) piezoelectric element having a diameter of 30 mm as a piezoelectric element, because existing liquid discharging heads are configured to form and discharge a liquid droplet by deforming a membranous member including a nozzle portion by means of bending vibration (flexural vibration) of the piezoelectric element.

In the present embodiment, displacement by the piezoelectric element 4030 is about 0.5 micrometers. Near the nozzle 4012 of the nozzle plate 4013 of the liquid container 4010, displacement by vibration of the nozzle plate 4013 is about ±0.5 micrometers (1.0 micrometer).

The pulse frequency and period of the voltage for driving the piezoelectric element 4030 are not particularly limited and may be appropriately selected depending on the intended purpose. In the present embodiment, the frequency is 10 kHz and the period is 500 Hz. The waveform of the voltage for driving the piezoelectric element 4030 is not particularly limited and may be appropriately selected depending on the intended purpose. In the present embodiment, a sinusoidal wave (sine wave) is used. As the waveform of the voltage for driving the piezoelectric element 4030, for example, a square wave may also be used.

Figure 36:
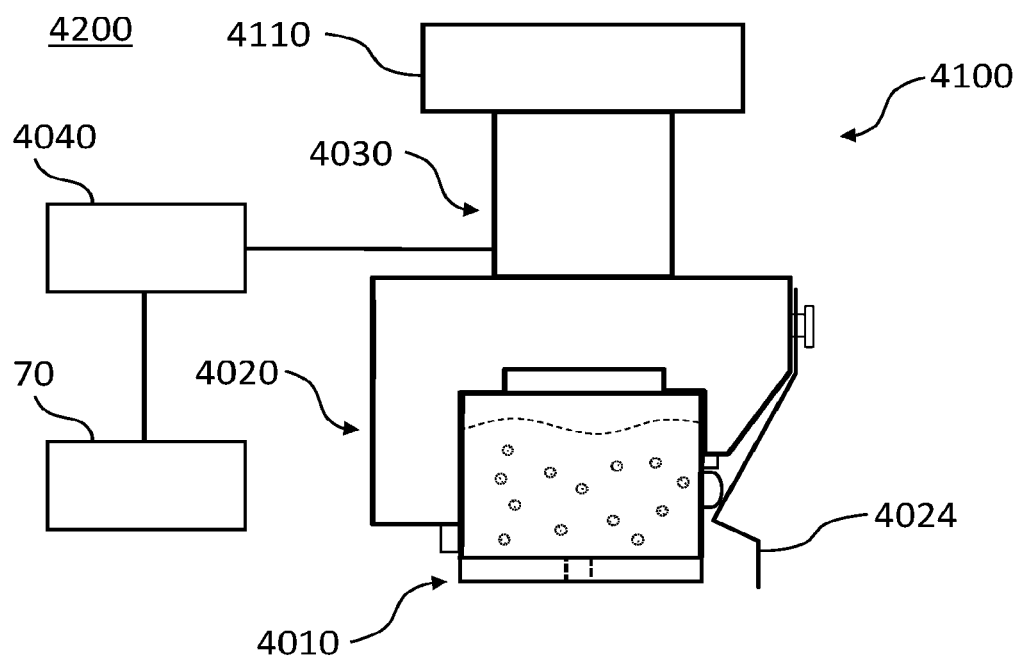
FIG. 36 is a schematic side view illustrating an example liquid discharging apparatus including a liquid discharging unit according to a fifteenth embodiment.

FIG. 36 is a schematic side view illustrating an example liquid discharging apparatus including the liquid discharging unit according to the fifteenth embodiment. The liquid discharging apparatus 4200 includes a liquid discharging unit 4100, a driving unit 4040, and a control unit 70. The control unit 70 is configured to control the voltage to be input by the driving unit 4040 to the piezoelectric element 4030, to control the operation of the piezoelectric element 4030 via the driving unit 4040.

Figure 37:
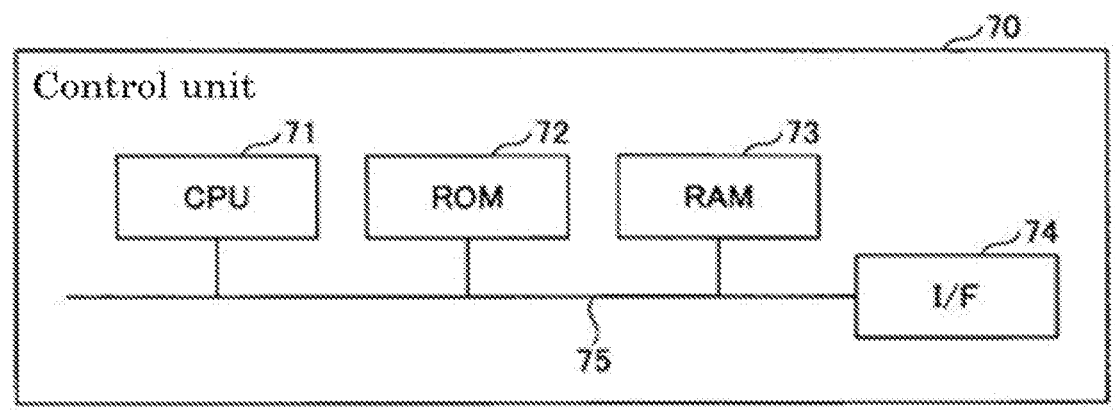
FIG. 37 is a block diagram illustrating an example of hardware of a control unit 70 illustrated in FIG. 36.

FIG. 37 is a block diagram illustrating example hardware of the control unit 70 illustrated in FIG. 36.

As illustrated in FIG. 37, the control unit 70 includes a CPU (Central Processing Unit) 71, a ROM (Read Only Memory) 72, a RAM (Random Access Memory) 73, an I/F (interface) 74, and a bus line 75. The CPU 71, the ROM 72, the RAM 73, and the I/F 74 are coupled to one another via the bus line 75.

The CPU 71 is configured to control various functions of the control unit 70. The ROM 72 serving as a memory unit is configured to store programs to be executed by the CPU 71 for controlling the various functions of the control unit 70 and various information. The RAM 73 serving as a memory unit is configured to be used as, for example, the work area of the CPU 71. The RAM 73 is also configured to be capable of storing predetermined information for a temporary period of time. The I/F 74 is configured to couple the liquid discharging apparatus 4200 to, for example, another device.

The liquid discharging apparatus 4200 may be coupled to, for example, an external network via the I/F 74.

The coupling member 4020 is configured to bias the liquid container 4010 via the locking member 4015 of the liquid container 4010 by means of the leaf spring 4024, to support the liquid container 4010 in a non-detachable manner.

Figure 22:
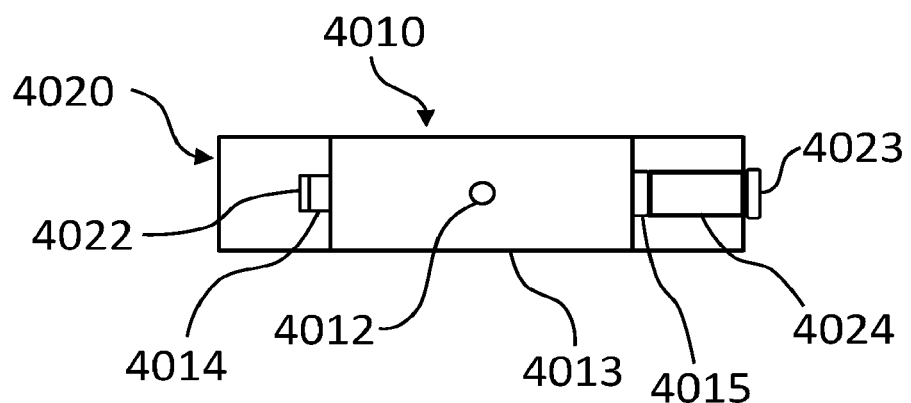
FIG. 22 is a schematic bottom view illustrating an example liquid discharging unit according to a fifteenth embodiment.

FIG. 22 is a schematic bottom view illustrating an example liquid discharging unit according to the fifteenth embodiment.

By the positioning rib 4014 of the liquid container 4010 and the positioning groove 4022 of the coupling member coming into contact with each other, the liquid container 4010 can be positioned accurately with respect to the coupling member 4020.

Figure 23A:
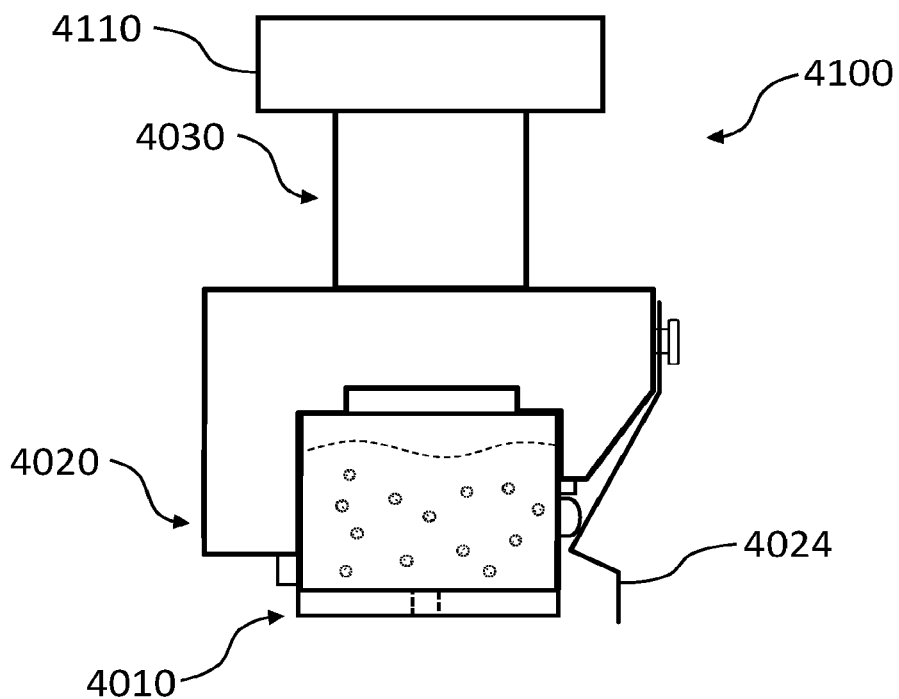
FIG. 23A is a schematic front view illustrating an example of a state of a liquid container being supported by a coupling member.
Figure 23B:
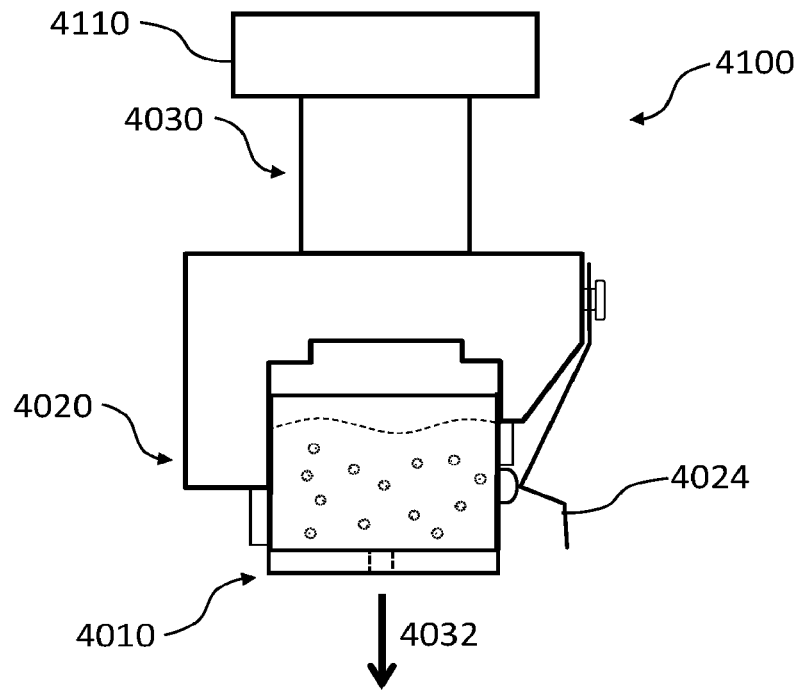
FIG. 23B is a schematic front view illustrating an example of a halfway state of a liquid container being demounted from a coupling member.
Figure 23C:
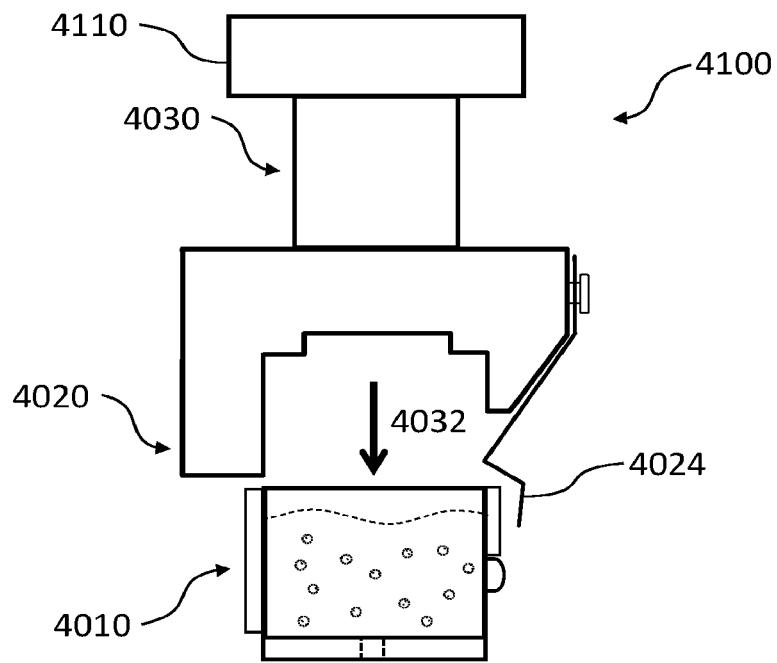
FIG. 23C is a schematic front view illustrating an example of a state after a liquid container is demounted from a coupling member.

With reference to FIG. 23A to FIG. 23C, the process flow of demounting the liquid container 4010 from the coupling member 4020 will be described.

FIG. 23A is a schematic front view illustrating an example of a state of the liquid container being supported by the coupling member. FIG. 23B is a schematic front view illustrating an example of a halfway state of the liquid container being demounted from the coupling member. FIG. 23C is a schematic front view illustrating an example of a state after the liquid container is demounted from the coupling member.

As illustrated in FIG. 23B, for example, by a user pulling the liquid container 4010 in the direction of an arrow 4032, the leaf spring 4024 is deformed by the liquid container 4010 while the liquid container 4010 is moving in the direction of the arrow 4032. Then, as illustrated in FIG. 23C, for example, by the user further puling the liquid container 4010 in the direction of the arrow 4032, the liquid container 4010 can be demounted.

When mounting the liquid container 4010, for example, by the user pushing the liquid container 4010 in a direction opposite to the arrow 4032, the liquid container 4010 can be mounted on the coupling member 4020 by a procedure reversed from when demounting the liquid container 4010.

Figure 24:
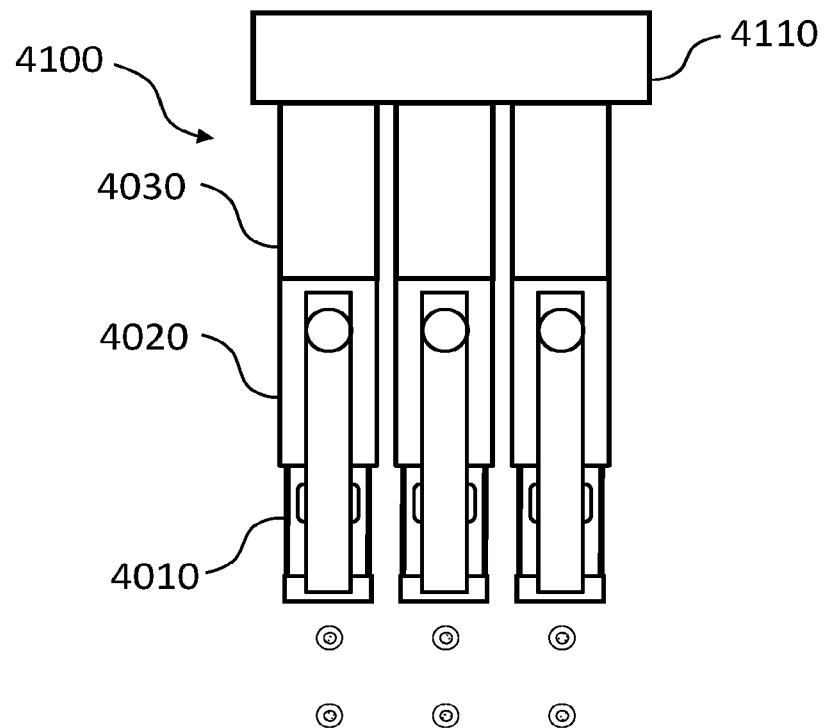
FIG. 24 is a schematic side view illustrating an example of a case where a plurality of liquid discharging units according to a fifteenth embodiment are disposed.
Figure 25:
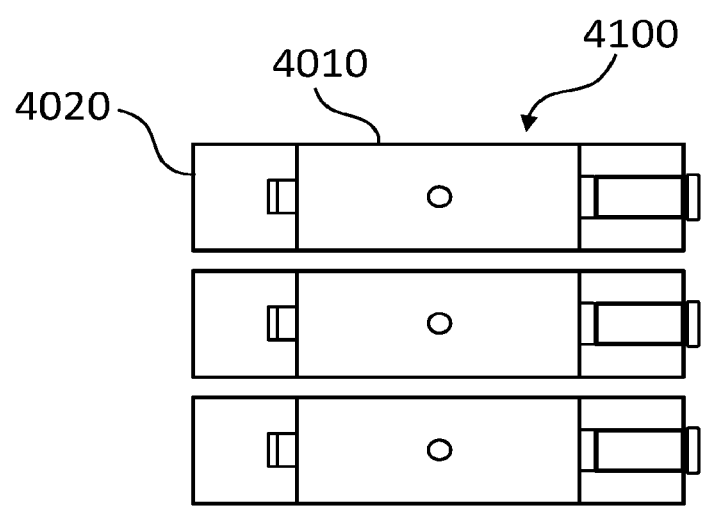
FIG. 25 is a schematic bottom view illustrating an example of a case where a plurality of liquid discharging units according to a fifteenth embodiment are disposed.

FIG. 24 is a schematic side view illustrating an example of a case where a plurality of liquid discharging units according to the fifteenth embodiment are disposed. FIG. 25 is a schematic bottom view illustrating an example of a case where a plurality of liquid discharging units according to the fifteenth embodiment are disposed.

As illustrated in FIG. 24 and FIG. 25, in the liquid discharging unit according to the fifth embodiment, the liquid container 4010, the coupling member 4020, and the piezoelectric element 4030 have the same horizontal length on the side surface. Therefore, the liquid discharging unit according to the fifteenth embodiment can be installed densely in the liquid discharging apparatus, making it possible to complete discharging the cell suspension 4300 in a shorter time.

Sixteenth Embodiment

Figure 26:
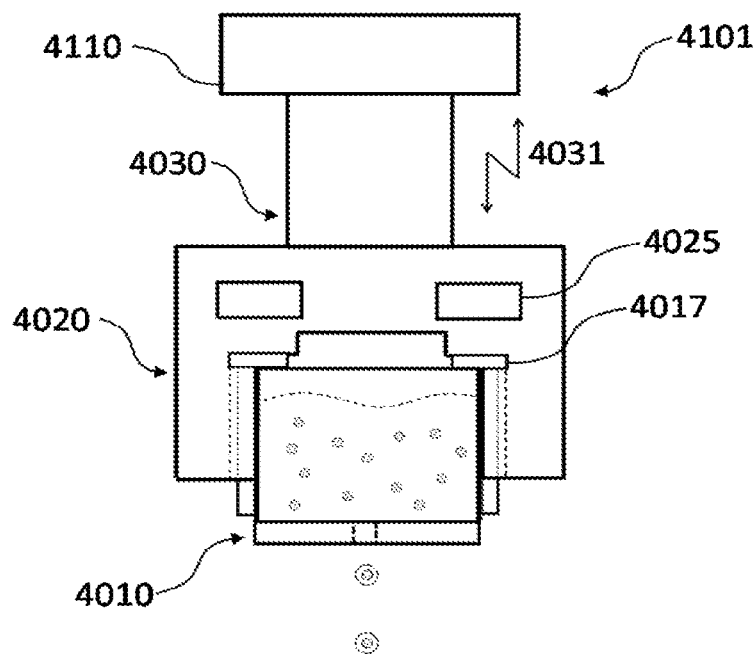
FIG. 26 is a schematic front view illustrating an example liquid discharging unit according to a sixteenth embodiment.

FIG. 26 is a schematic front view illustrating an example of a liquid discharging unit according to the sixteenth embodiment.

In the sixteenth embodiment, the coupling member 4020 of the liquid discharging unit 4101 is configured to support the liquid container 4010 by means of an attractive force based on a magnetic force generated between a permanent magnet 4025 serving as a magnetic body and an iron member 4017 serving as an adsorbing member.

Seventeenth Embodiment

Figure 27:
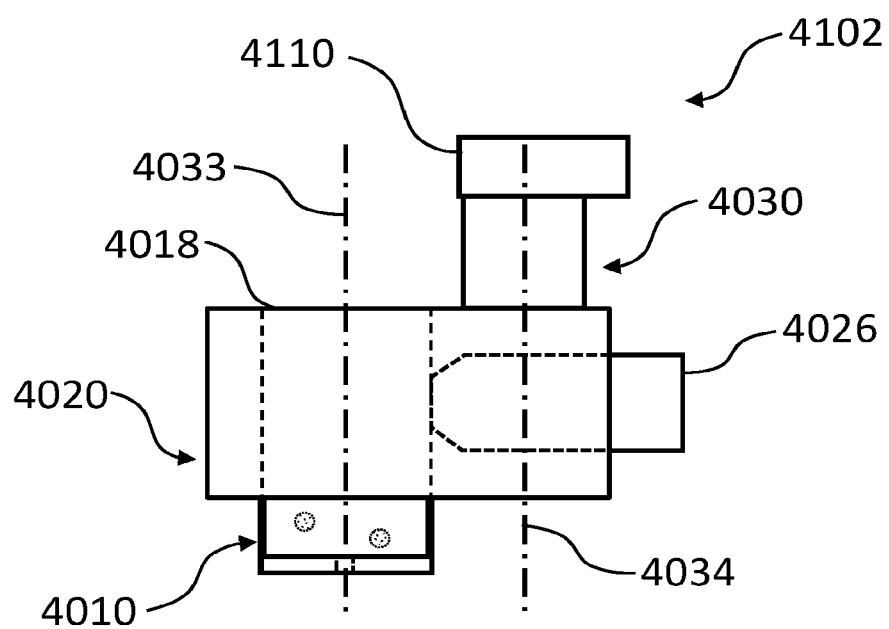
FIG. 27 is a schematic front view illustrating an example liquid discharging unit according to a seventeenth embodiment.
Figure 28:
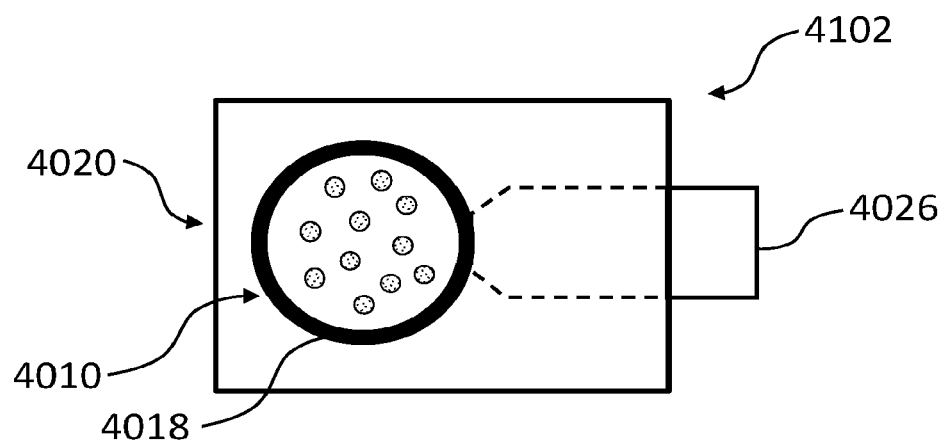
FIG. 28 is a schematic top view illustrating an example liquid discharging unit according to a seventeenth embodiment.
Figure 29:
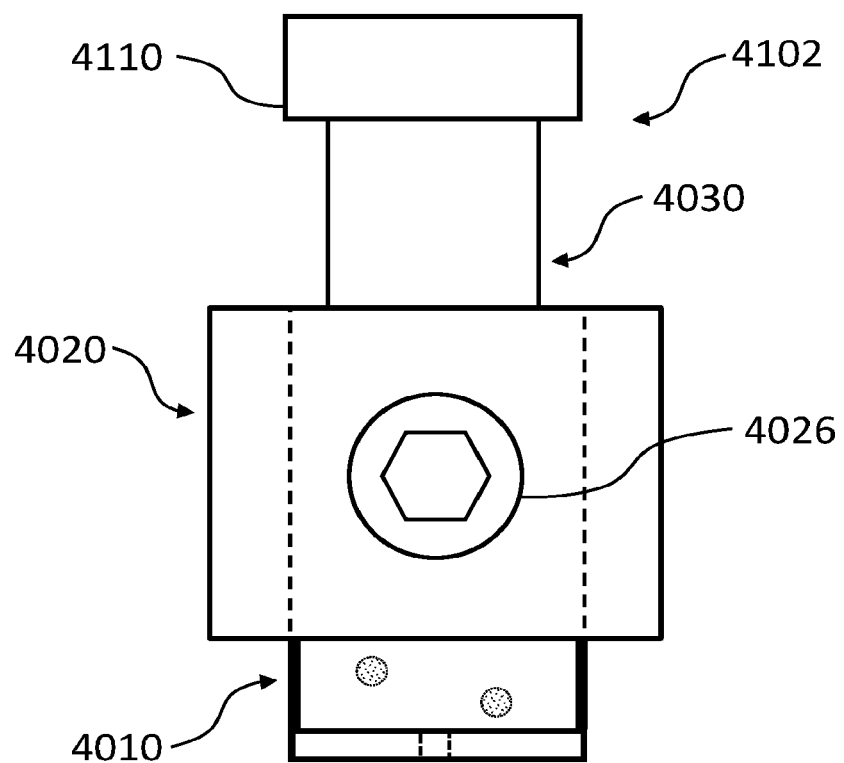
FIG. 29 is a schematic side view illustrating an example liquid discharging unit according to a seventeenth embodiment.
Figure 30:
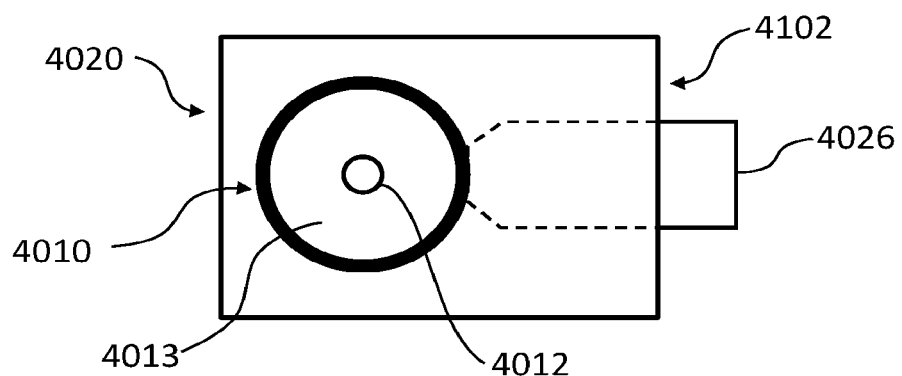
FIG. 30 is a schematic bottom view illustrating an example liquid discharging unit according to a seventeenth embodiment.

FIG. 27 is a schematic front view illustrating an example liquid discharging unit according to the seventeenth embodiment. FIG. 28 is a schematic top view illustrating an example liquid discharging unit according to the seventeenth embodiment. FIG. 29 is a schematic side view illustrating an example liquid discharging unit according to the seventeenth embodiment. FIG. 30 is a schematic bottom view illustrating an example liquid discharging unit according to the seventeenth embodiment.

As illustrated in FIG. 27, in the liquid discharging unit 4102 according to the seventeenth embodiment, the center axis 4033 of the liquid container 4010 in the gravity direction and the drive axis 4034 of the piezoelectric element 4030 are at positions shifted in the horizontal direction. This makes it possible for no other member to be disposed above an opening 4018, making it possible to operate the cell suspension 4300 contained in the liquid container 4010 easily with a pipette 4111 serving as an operation tool (see FIG. 31).

Further, in the liquid discharging unit 4102 according to the seventeenth embodiment, the liquid container 4010 and the coupling member 4020 are, when regarded as one member, disposed to have a center of gravity come close to the drive axis 4034 in order to suppress destabilization of vibration due to the horizontal shift between the center axis 4033 and the drive axis 4034. This makes it possible to suppress destabilization of vibration and discharge liquid droplets 4310 more stably.

In the liquid discharging unit 4102 according to the seventeenth embodiment, the coupling member 4020 supports the liquid container 4010 by biasing the liquid container 4010 with a hex socket screw 4026. Hence, in the liquid discharging unit 4102 according to the seventeenth embodiment, by having a cylindrical shape, the liquid container 4010 is suppressed from being deformed by the biasing force from the hex socket screw 4026.

Further, as illustrated in FIG. 27 to FIG. 30, in the liquid discharging unit according to the seventeenth embodiment, the liquid container 4010 has the opening 4018 through which the cell suspension 4300 contained in the liquid container 4010 is exposed to the outside of the liquid container 4010. In the liquid discharging unit according to the seventeenth embodiment, a ventilation port 4016 and the opening 4018 are the same member.

Figure 31:
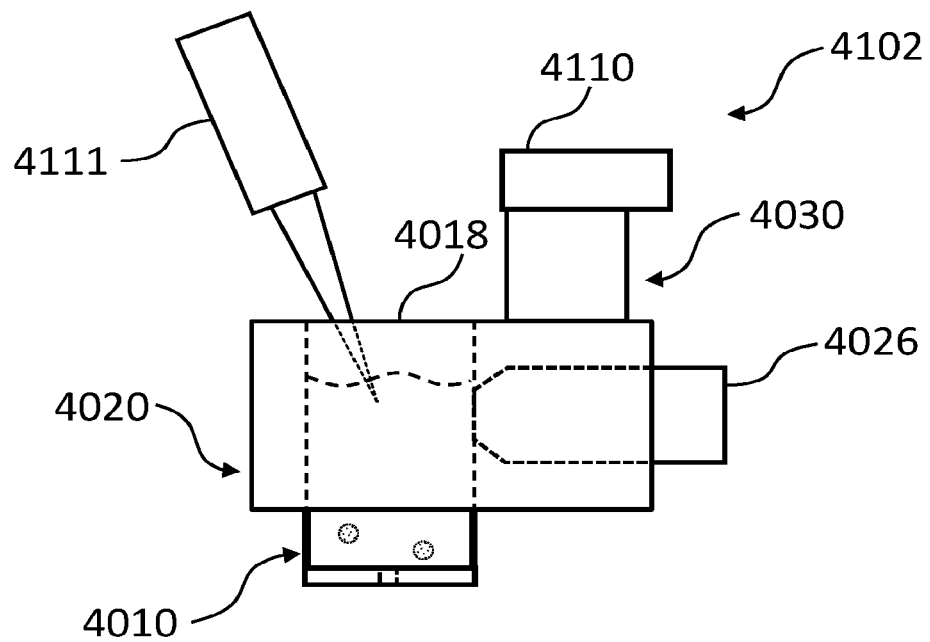
FIG. 31 is a schematic view illustrating an example of a state when a liquid contained in a liquid container is operated without the liquid container being demounted from a coupling member in a liquid discharging unit according to a seventeenth embodiment.

FIG. 31 is a schematic view illustrating an example of a state when the liquid contained in the liquid container is operated without the liquid container being demounted from the coupling member in the liquid discharging unit according to the seventeenth embodiment.

As illustrated in FIG. 31, in the liquid discharging unit 4102 according to the seventeenth embodiment, owing to the presence of the opening 4018, it is possible to operate the cell suspension 4300 contained in the liquid container 4010 with a pipette 4111 as an operation tool, without demounting the liquid container 4010 from the coupling member 4020.

Figure 32A:
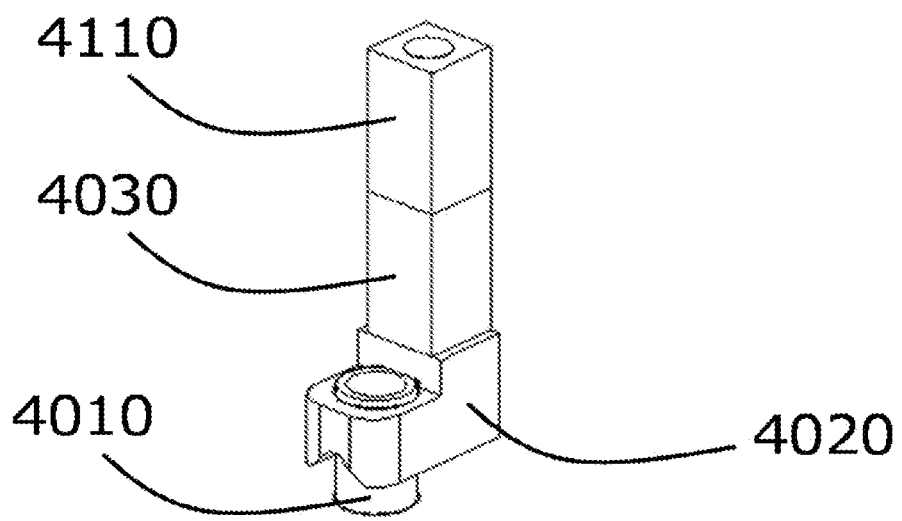
FIG. 32A is a perspective view of a modified liquid discharging unit according to a seventeenth embodiment when seen from one side.
Figure 32B:
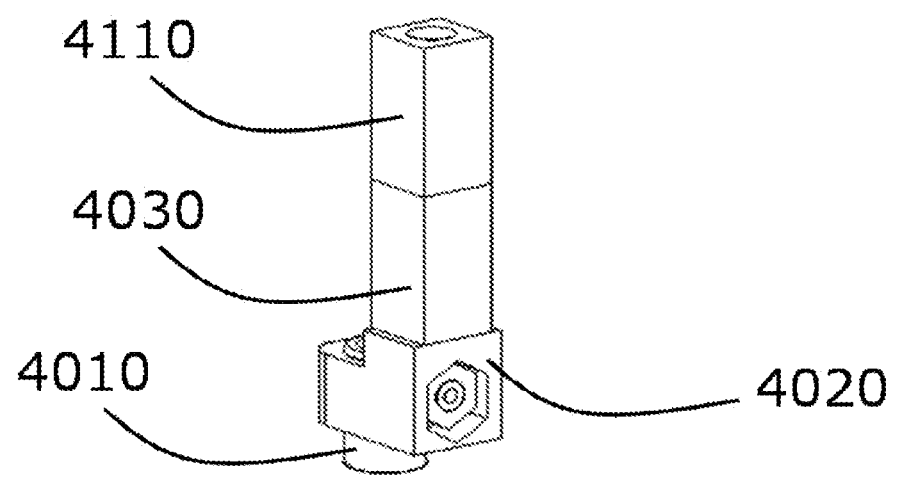
FIG. 32B is a perspective view of a modified liquid discharging unit according to a seventeenth embodiment when seen from another side.

FIG. 32A is a perspective view of a modified example of the liquid discharging unit according to the seventeenth embodiment when seen from one side. FIG. 32B is a perspective view of the modified example of the liquid discharging unit according to the seventeenth embodiment when seen from another side.

In the example illustrated in FIG. 32A and FIG. 32B, the hex socket screw 4026 is configured to be accommodated inside the coupling member 4020. This makes it possible to further reduce the size of the liquid discharging head.

Figure 33A:
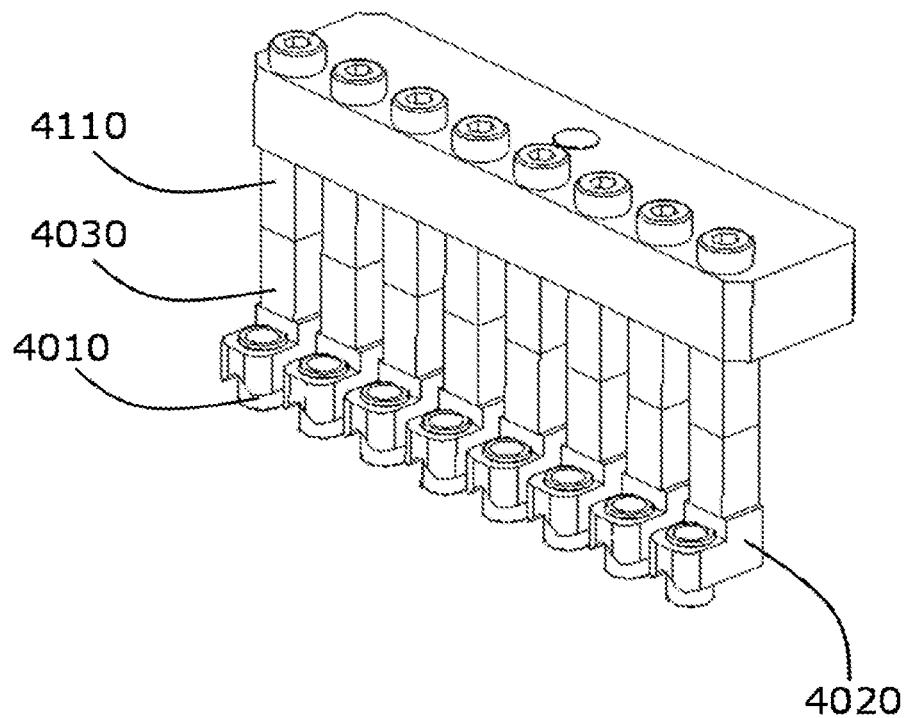
FIG. 33A is a perspective view, when seen from one side, of a multichannel in which a plurality of modified liquid discharging units according to a seventeenth embodiment are disposed side by side.
Figure 33B:
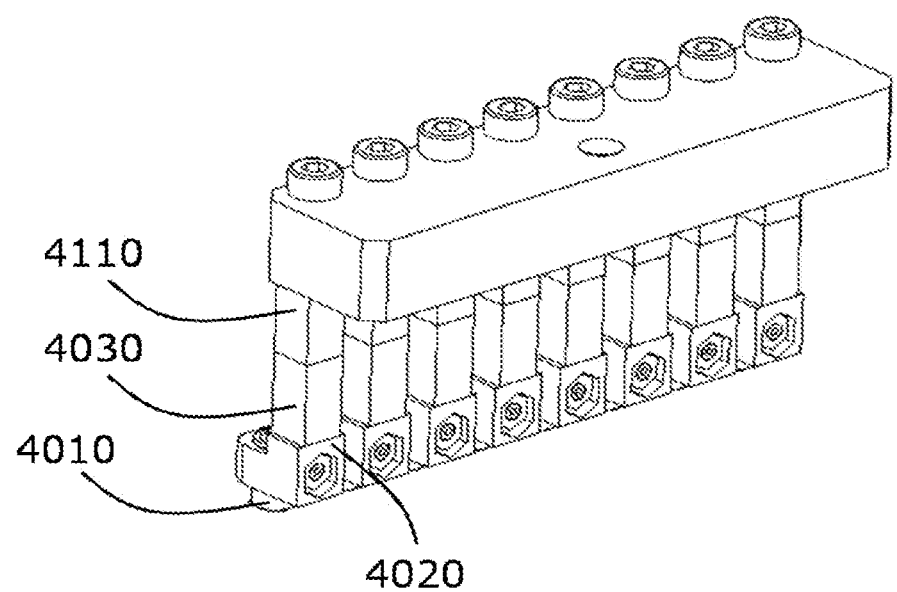
FIG. 33B is a perspective view, when seen from another side, of a multichannel in which a plurality of modified liquid discharging units according to a seventeenth embodiment are disposed side by side.

FIG. 33A is a perspective view, when seen from one side, of a multichannel in which a plurality of modified liquid discharging units according to the seventeenth embodiment are disposed side by side. FIG. 33B is a perspective view, when seen from another side, of a multichannel in which a plurality of modified liquid discharging units according to the seventeenth embodiment are disposed side by side.

As illustrated in FIG. 33A and FIG. 33B, because the liquid discharging unit according to the seventeenth embodiment can be made small in size, the liquid discharging unit can be suitably used when forming a multichannel by disposing a plurality of liquid discharging units side by side.

Eighteenth Embodiment

Figure 34:
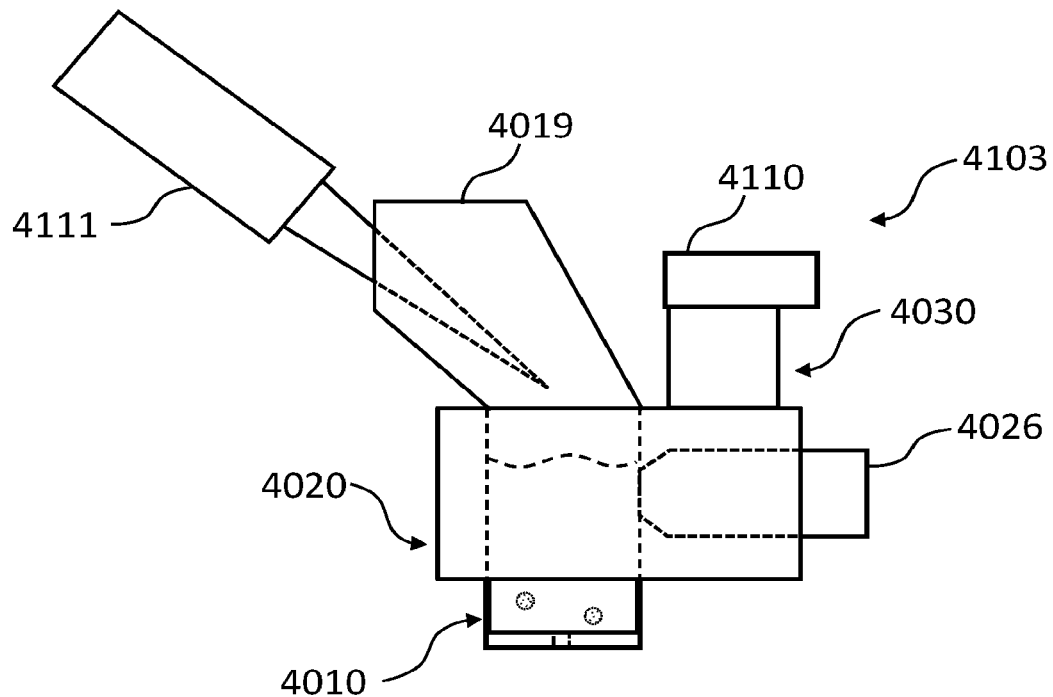
FIG. 34 is a schematic view illustrating an example of a state when a liquid contained in a liquid container is operated via an adhesion preventing unit without the liquid container being demounted from a coupling member in a liquid discharging unit according to an eighteenth embodiment.

FIG. 34 is a schematic view illustrating an example of a state when a liquid contained in a liquid container is operated via an adhesion preventing unit without the liquid container being demounted from the coupling member in a liquid discharging unit according to the eighteenth embodiment.

Figure 35:
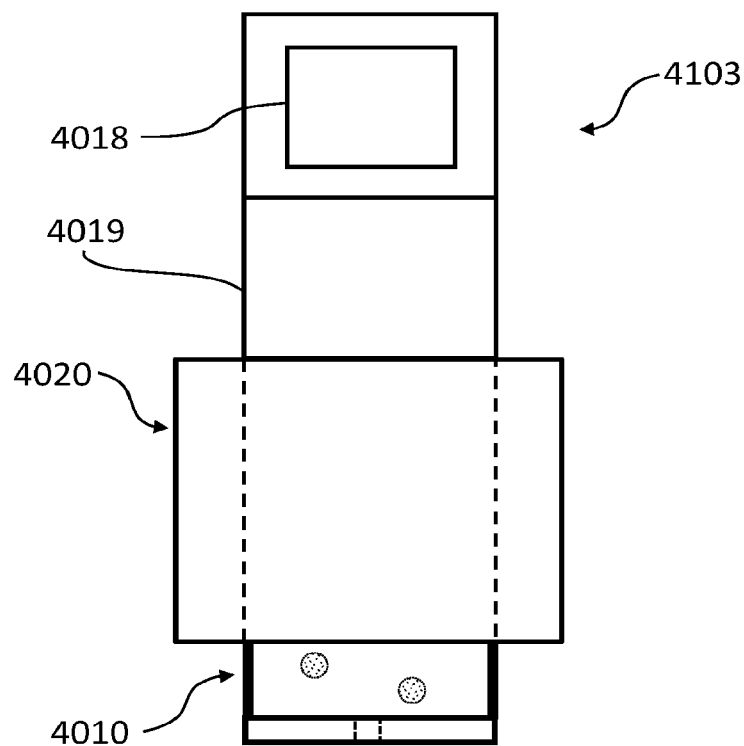
FIG. 35 is a schematic side view illustrating an example liquid discharging unit according to an eighteenth embodiment.

FIG. 35 is a schematic side view illustrating an example liquid discharging unit according to the eighteenth embodiment.

As illustrated in FIG. 34 and FIG. 35, in the liquid discharging unit 4103 according to the eighteenth embodiment, the liquid container 4010 includes an adhesion preventing unit 4019 configured to prevent adhesion of the cell suspension 4300 to the outside of the liquid container 4010.

In the liquid discharging unit 4103 according to the eighteenth embodiment, the adhesion preventing unit 4019 has an opening 4018, making it possible to operate the cell suspension 4300 contained in the liquid container 4010 via the adhesion preventing unit 4019 without demounting the liquid container 4010 from the coupling member 4020.

In this way, in the fifteenth to eighteenth embodiments, the piezoelectric element 4030 as an example of the displacement member is disposed at the side at which the liquid to be discharged through the discharging port (nozzle) 4012 is provided. This may be an example of the first aspect described above. Further, there is provided the coupling member 4020 configured to couple the membranous member 4013 and the displacement member 4030 to each other in a manner that the membranous member 4013 is mountable and demountable. This may be an example of the third aspect described above. Furthermore, in the fifteenth to eighteenth embodiments, there are provided the liquid container (liquid retaining unit) 4010 including the discharging port 4012 through which a liquid is discharged, and the piezoelectric element 4030 as an example of the displacement member configured to displace the position of the liquid container 4010 to cause the liquid to be discharged through the discharging port 4012. This may be an example of the fourth aspect described above.

Nineteenth Embodiment

Figure 38:
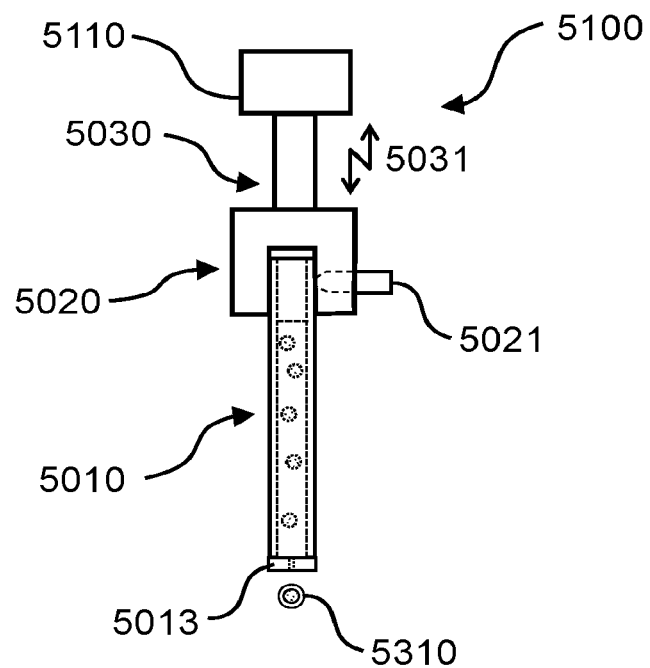
FIG. 38 is a schematic front view illustrating an example liquid discharging head according to a nineteenth embodiment.
Figure 39A:
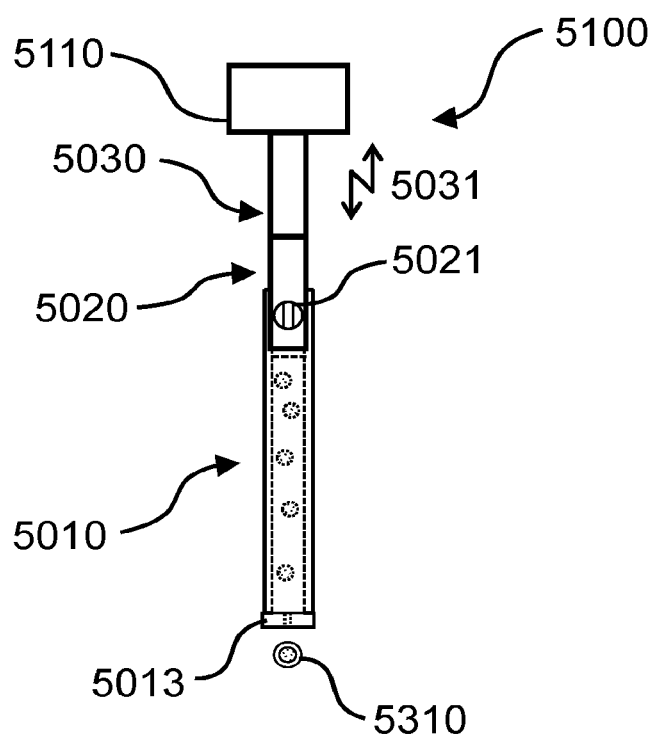
FIG. 39A is a schematic side view illustrating an example liquid discharging head according to a nineteenth embodiment.
Figure 39B:
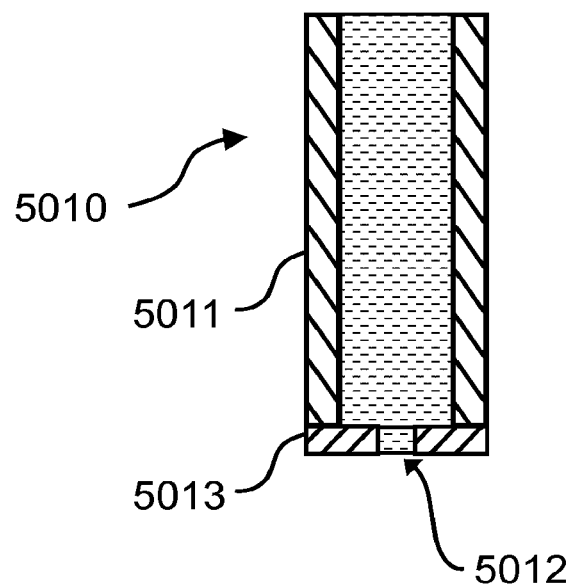
FIG. 39B is a schematic cross-sectional view illustrating a portion near a discharging port in an example liquid discharging head according to a nineteenth embodiment.
Figure 39C:
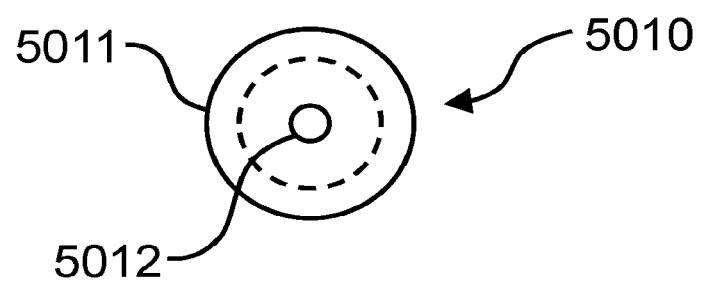
FIG. 39C is a schematic bottom view illustrating a portion near a discharging port in an example liquid discharging head according to a nineteenth embodiment.

FIG. 38 is a schematic front view illustrating an example liquid discharging head according to the nineteenth embodiment. FIG. 39A is a schematic side view illustrating the example liquid discharging head according to the nineteenth embodiment. FIG. 39B is a schematic cross-sectional view illustrating a portion near the discharging port in the example liquid discharging head according to the nineteenth embodiment. FIG. 39C is a schematic bottom view illustrating a portion near the discharging port in the example liquid discharging head according to the nineteenth embodiment.

As illustrated in FIG. 38 to FIG. 39C, in the nineteenth embodiment, the liquid discharging head 5100 includes a liquid retaining unit 5010, a coupling member 5020, and a piezoelectric element 5030 as a displacement member.

The nineteenth embodiment may be the same as the fifteenth embodiment in any respects that are not particularly described below.

In the nineteenth embodiment, the liquid retaining unit 5010 includes a liquid chamber (liquid containing chamber) 5011 and a membranous member (nozzle plate) 5013 including a discharging port (nozzle) 5012.

The coupling member 5020 is configured to couple (support) the liquid retaining unit 5010 by biasing the liquid retaining unit 5010 with a spring 5021.

The piezoelectric element 5030 is bonded to the coupling member 5020 and the securing member 5110, and vibrates in the direction of an arrow 5031 when a voltage is applied. Hence, vibrating the piezoelectric element 5030 can cause the liquid retaining unit 5010 and the coupling member 5020 to vibrate and can cause a liquid droplet 5310 of the cell suspension suspending the cells to be discharged through the discharging port 5012.

In the nineteenth embodiment, the coupling member 5020 is configured to couple the liquid retaining unit 5010 including the membranous member 5013 in a manner that liquid retaining units can be disposed adjacently. More specifically, in the nineteenth embodiment, the coupling member 5020 enables liquid retaining units 5010 including membranous members 5013 to be disposed closely adjacently to each other in the direction in which the liquid retaining units 5010 including the membranous members 5013 are disposed side by side.

Figure 40A:
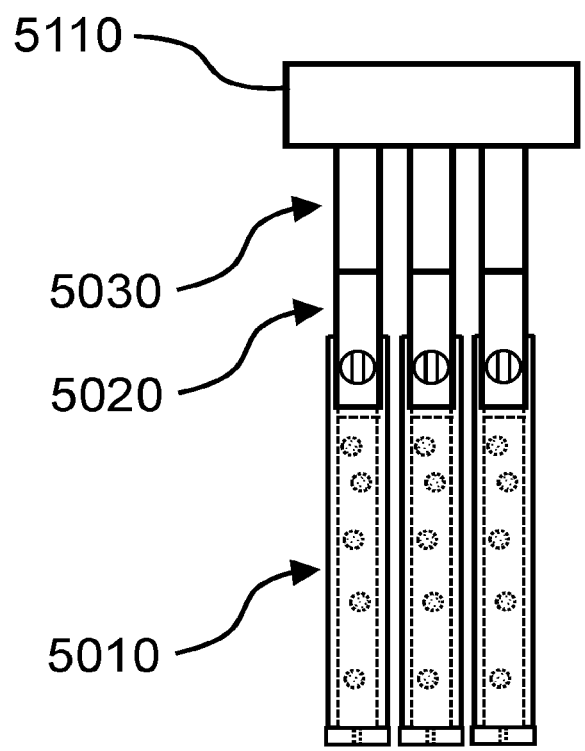
FIG. 40A is a schematic side view of a multichannel in which three liquid discharging heads according to a nineteenth embodiment are disposed adjacently.
Figure 40B:
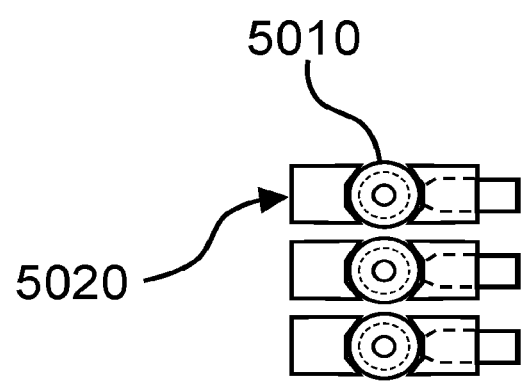
FIG. 40B is a schematic bottom view of a multichannel in which three liquid discharging heads according to a nineteenth embodiment are disposed adjacently.

FIG. 40A is a schematic side view illustrating a multichannel in which three liquid discharging heads according to the nineteenth embodiment are disposed adjacently. FIG. 40B is a schematic bottom view illustrating a multichannel in which three liquid discharging heads according to the nineteenth embodiment are disposed adjacently.

As illustrated in FIG. 40A and FIG. 40B, the diameter of the coupling member 5020 is shorter than the diameter of the liquid retaining unit 5010 in the direction in which the liquid retaining units 5010 including the membranous members 5013 are disposed side by side, and the liquid retaining units 5010 including the membranous members 5013 are disposed adjacently.

Figure 41A:
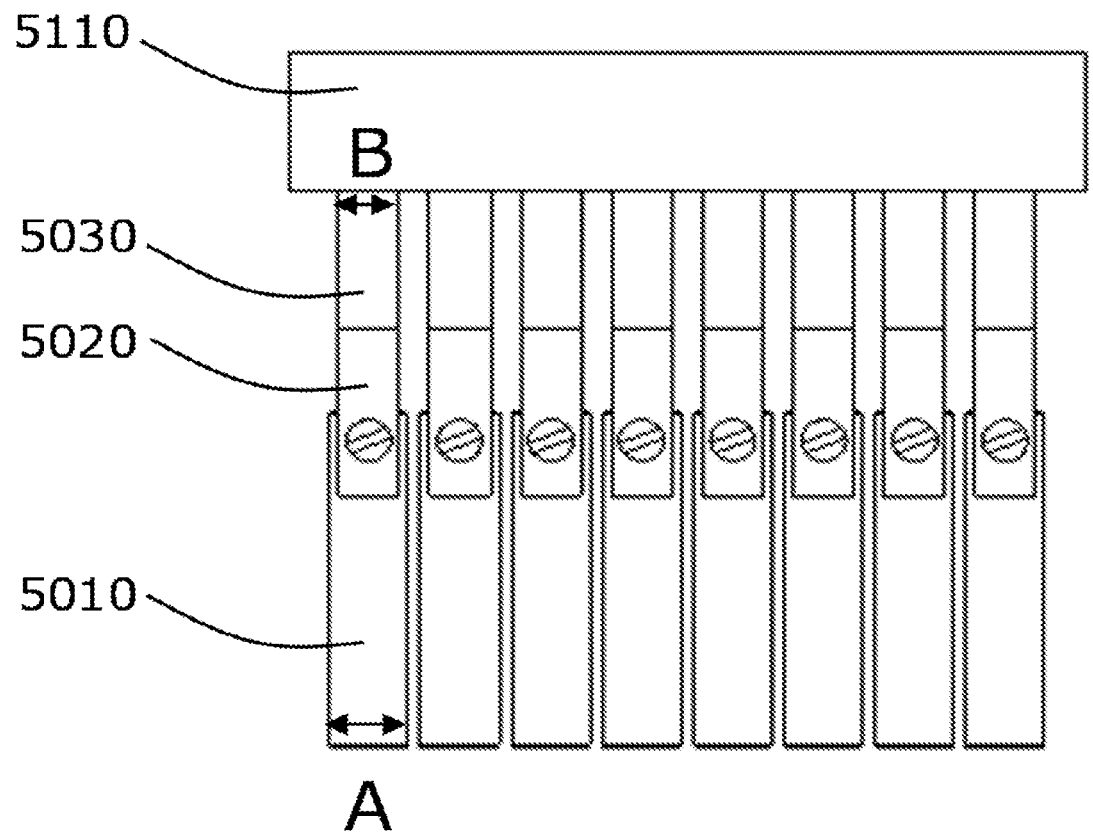
FIG. 41A is a side view of a multichannel in which eight liquid discharging heads according to a nineteenth embodiment are disposed adjacently.
Figure 41B:
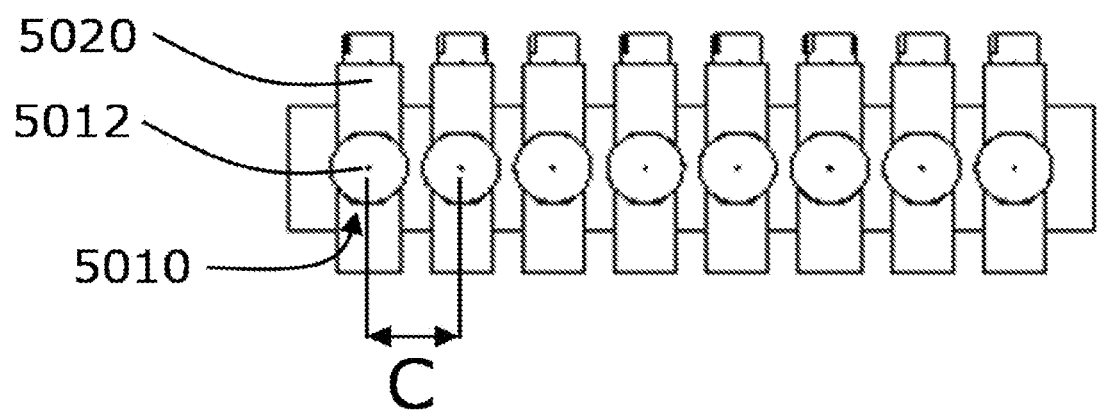
FIG. 41B is a bottom view of a multichannel in which eight liquid discharging heads according to a nineteenth embodiment are disposed adjacently.
Figure 41C:
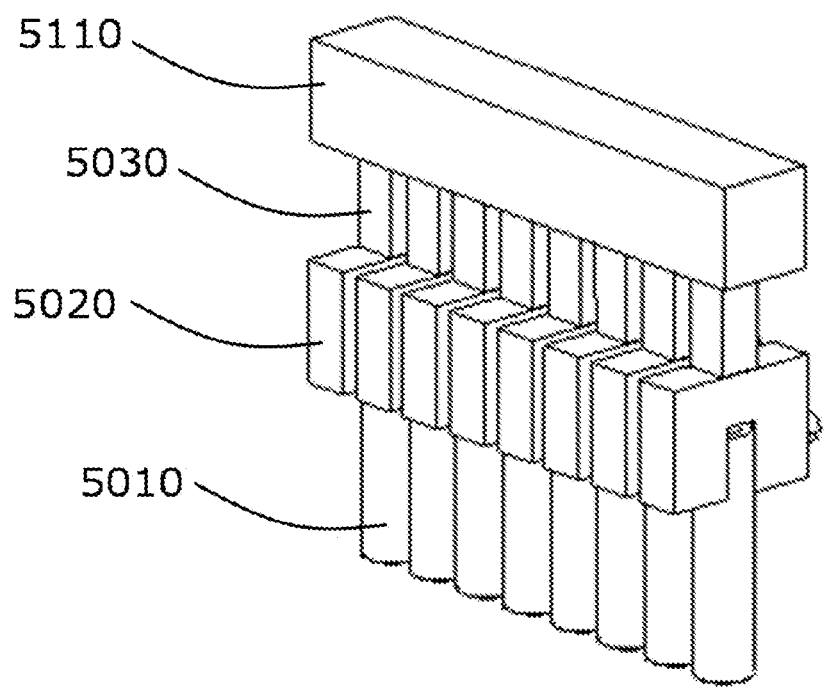
FIG. 41C is a perspective view, when seen from one side, of a multichannel in which eight liquid discharging heads according to a nineteenth embodiment are disposed adjacently.
Figure 41D:
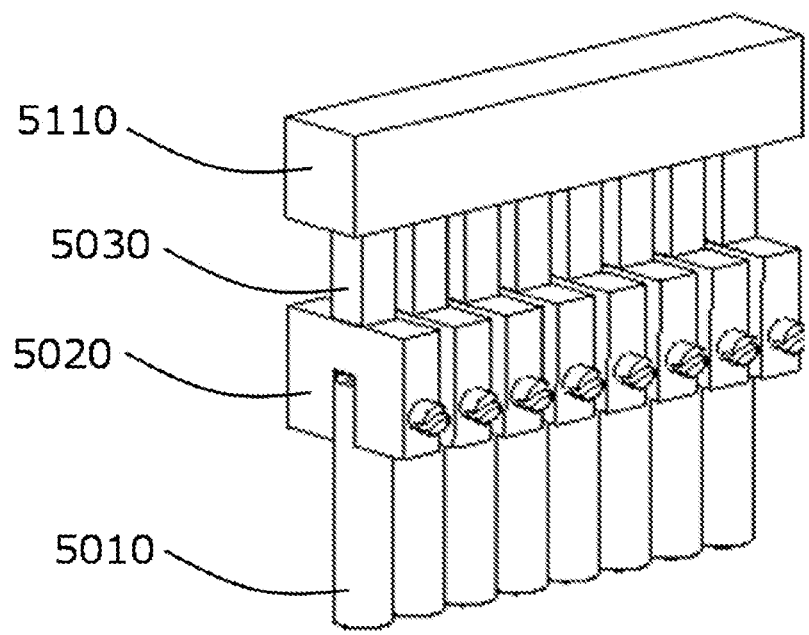
FIG. 41D is a perspective view, when seen from another side, of a multichannel in which eight liquid discharging heads according to a nineteenth embodiment are disposed adjacently.

FIG. 41A is a side view illustrating a multichannel in which eight liquid discharging heads according to the nineteenth embodiment are disposed adjacently. FIG. 41B is a bottom view illustrating a multichannel in which eight liquid discharging heads according to the nineteenth embodiment are disposed adjacently. FIG. 41C is a perspective view, when seen from one side, of a multichannel in which eight liquid discharging heads according to the nineteenth embodiment are disposed adjacently. FIG. 41D is a perspective view, when seen from another side, of a multichannel in which eight liquid discharging heads according to the nineteenth embodiment are disposed adjacently.

In the example illustrated in FIG. 41A to FIG. 41D, the diameter B of the coupling member 5020 is shorter than the diameter A of the liquid retaining unit 5010 in the direction in which the liquid retaining units 5010 are disposed side by side, and the liquid retaining units 5010 including the membranous members 5013 are disposed adjacently. This makes it possible to make the pitch C between the discharging ports shorter while maintaining the amount of the liquid that can be retained in the liquid retaining unit 5010.

In the example illustrated in FIG. 41A to FIG. 41D, in the direction in which the liquid retaining units 5010 are disposed side by side, the diameter A of the liquid retaining unit 5010 is 2.5 mm, the diameter B of the coupling member 5020 is 2.0 mm, and the pitch C between the discharging ports is 3.0 mm.

Twentieth Embodiment

Figure 42A:
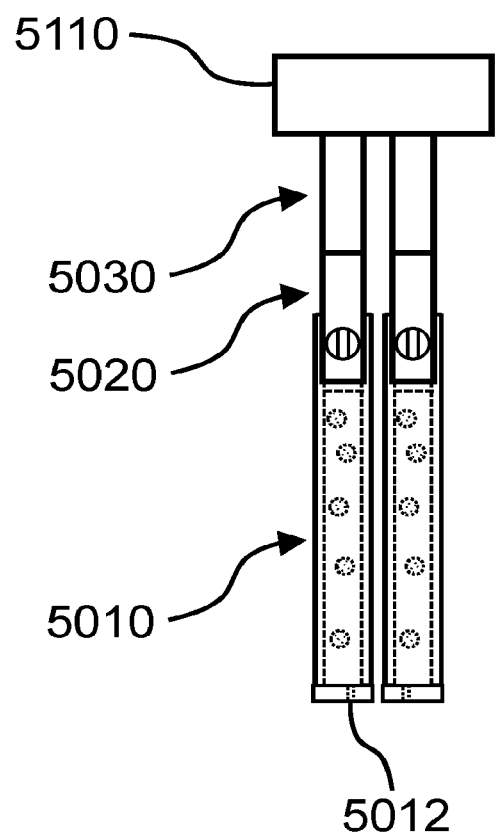
FIG. 42A is a schematic side view of a multichannel in which two liquid discharging heads according to a twentieth embodiment are disposed adjacently.
Figure 42B:
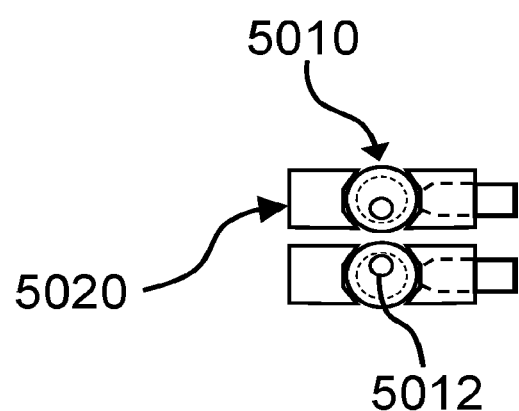
FIG. 42B is a schematic bottom view of a multichannel in which three liquid discharging heads according to a twentieth embodiment are disposed adjacently.
Figure 42C:
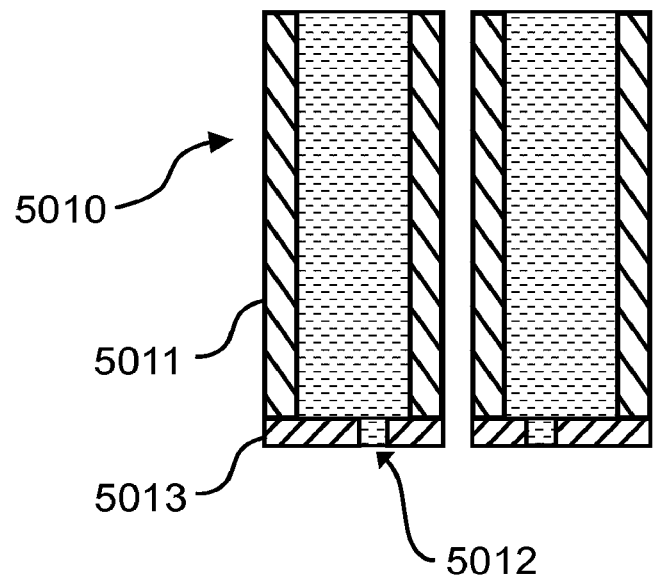
FIG. 42C is a schematic cross-sectional view illustrating a portion near discharging ports of a multichannel in which two liquid discharging heads according to a twentieth embodiment are disposed adjacently.
Figure 42D:
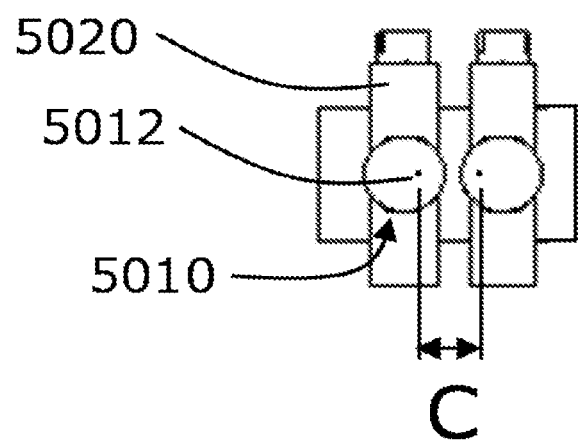
FIG. 42D is a bottom view of a multichannel in which two liquid discharging heads according to a twentieth embodiment are disposed adjacently.

FIG. 42A is a schematic side view of a multichannel in which two liquid discharging heads according to the twentieth embodiment are disposed adjacently. FIG. 42B is a schematic bottom view of a multichannel in which three liquid discharging heads according to the twentieth embodiment are disposed adjacently. FIG. 42C is a schematic cross-sectional view illustrating a portion near discharging ports of a multichannel in which two liquid discharging heads according to the twentieth embodiment are disposed adjacently. FIG. 42D is a bottom view of a multichannel in which two liquid discharging heads according to the twentieth embodiment are disposed adjacently.

As illustrated in FIG. 42A to FIG. 42D, in the liquid discharging head according to the twentieth embodiment, the discharging port 5012 is provided not in the center of the membranous member 5013, but at an off-center position. More specifically, in the twentieth embodiment, the discharging ports 5012 are provided at positions at which the discharging ports 5012 of the two liquid discharging heads adjacent to each other are closer to each other. In other words, the discharging ports 5012 are provided in a manner to make the pitch C shorter between the discharging ports of the two liquid discharging heads adjacent to each other. In this way, in the twenties embodiment, it is possible to discharge liquid droplets more densely, with a shorter pitch C between the discharging ports.

Figure 43A:
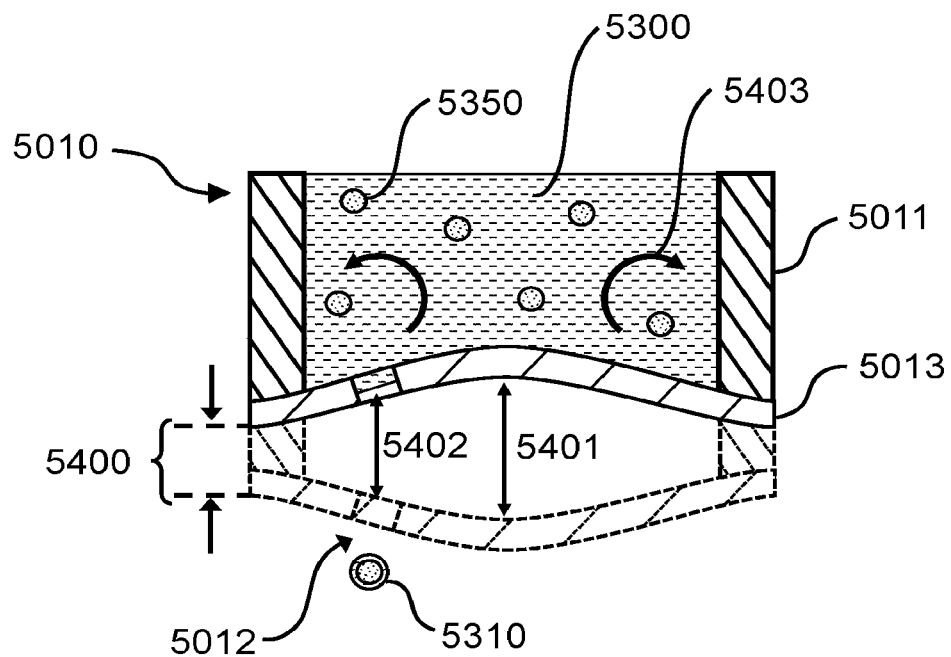
FIG. 43A is a schematic cross-sectional view illustrating an example of a state when a liquid discharging head according to a twentieth embodiment is displaced to cause a liquid to be discharged through a discharging port.
Figure 43B:
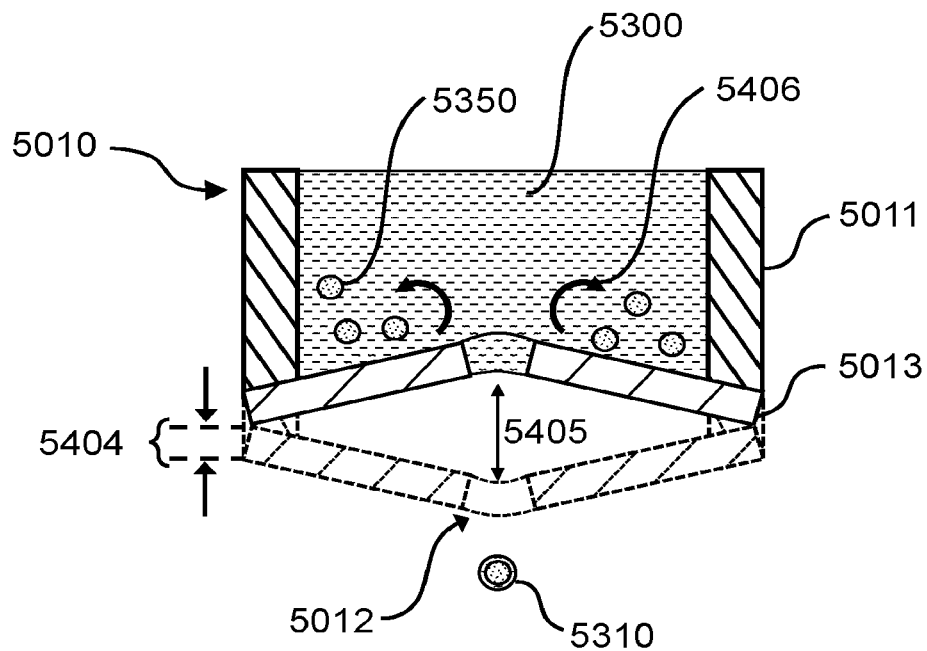
FIG. 43B is a schematic cross-sectional view illustrating an example of a state when a liquid discharging head according to a twentieth embodiment is displaced to cause a liquid to be discharged through a discharging port.

FIG. 43A is a schematic cross-sectional view illustrating an example of a state when the liquid discharging head according to the twentieth embodiment is displaced to cause a liquid to be discharged through the discharging port. FIG. 43B is a schematic cross-sectional view illustrating a state when the liquid discharging head according to the twentieth embodiment is displaced to cause a liquid to be discharged through the discharging port.

As illustrated in FIG. 43A, a case of discharging a cell suspension 5300 suspending cells 5350 as particles through the discharging port 5012 in the form of a liquid droplet 5310 is considered. When the position of the membranous member 5013 is displaced in order to cause the cell suspension 5300 to be discharged through the discharging port 5012, the membranous member 5013 minutely vibrates in the secondary mode depending on a displacement 5400 of the position of the membranous member 5013. Here, the displacement of the position of the discharging port 5012 is the sum of the displacement 5400 of the whole membranous member 5013 and a displacement of the membranous member 5013 by the own minute vibration in the secondary mode.

The displacement of the discharging port 5012 suitable for discharging the cell suspension 5300 through the discharging port 5012 is almost a constant value regardless of the position of the discharging port 5012. That is, it is preferable that a displacement 5402 of the discharging port 5012 in FIG. 43A be roughly the same value as a displacement 5405 of the discharging port 5012 in FIG. 43B. On the other hand, a displacement of the membranous member 5013 by the own minute vibration in the secondary mode is considered the maximum at the center of the membranous member. Therefore, the displacement 5402 of the discharging port 5012 in FIG. 43A is smaller than a displacement 5401 of the center of the membranous member 5013.

Hence, as illustrated in FIG. 43A and FIG. 43B, when the discharging port 5012 is positioned off the center, the displacement 5400 of the position of the membranous member 5013 in FIG. 43A is set greater than a displacement 5404 of the position of the membranous member 5013 in FIG. 43B in order to make the displacement 5402 of the discharging port 5012 in FIG. 43A roughly the same as the displacement 5405 of the discharging port 5012 in FIG. 43B.

In this way, when the displacement 5400 of the position of the membranous member 5013 in FIG. 43A is set greater than the displacement 5404 of the position of the membranous member 5013 in FIG. 43B, the displacement 5401 of the center of the membranous member 5013 also becomes greater. Therefore, a liquid stirring force indicated by an arrow 5403 in FIG. 43A is greater than a liquid stirring force indicated by an arrow 5406 in FIG. 43B.

That is, for example, in the case of discharging a particle-containing liquid such as the cell suspension 5300, the twentieth embodiment is more effective than the nineteenth embodiment in stirring the liquid, making it possible to disperse the particles and suppress the discharging port from being clogged with the particles when the liquid is discharged.

Twenty-First Embodiment

Figure 44A:
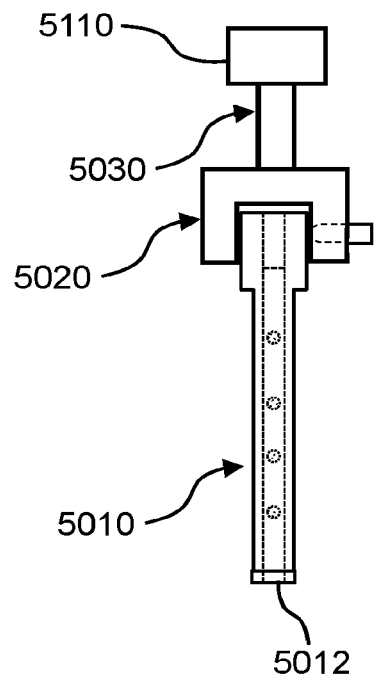
FIG. 44A is a schematic front view illustrating an example liquid discharging head according to a twenty-first embodiment.
Figure 44B:
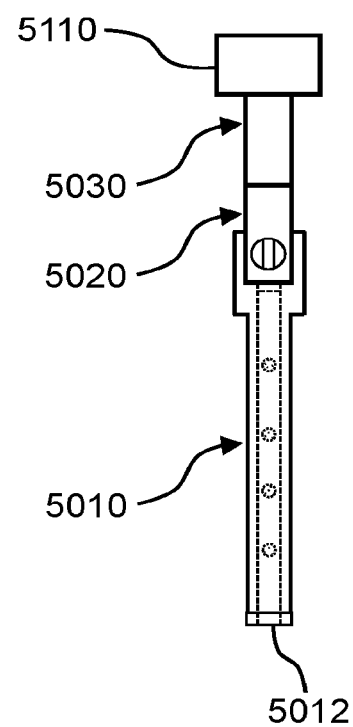
FIG. 44B is a schematic side view illustrating an example liquid discharging head according to a twenty-first embodiment.
Figure 44C:
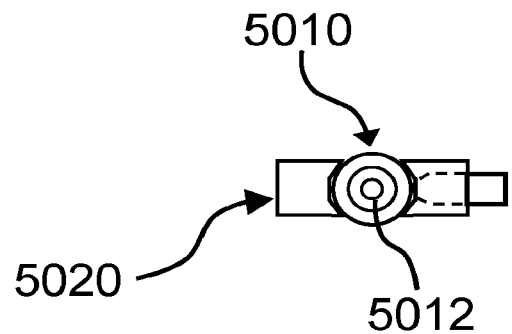
FIG. 44C is a schematic bottom view illustrating an example liquid discharging head according to a twenty-first embodiment.
Figure 44D:
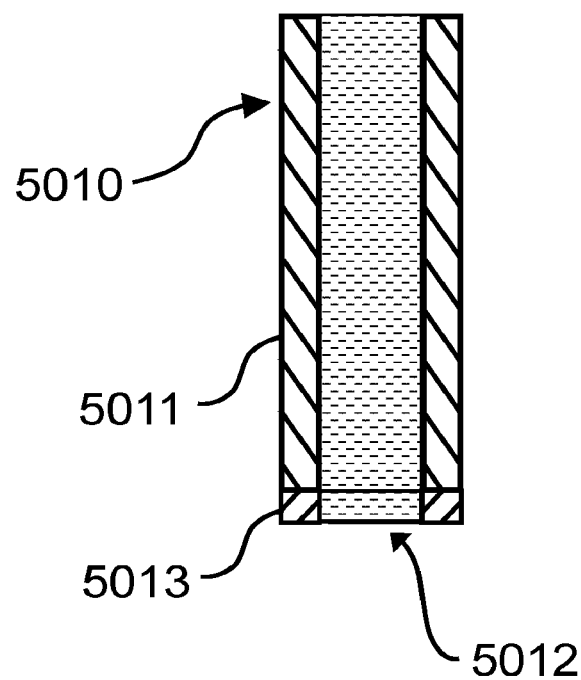
FIG. 44D is a schematic cross-sectional view illustrating a portion near a discharging port of an example liquid discharging head according to a twenty-first embodiment.

FIG. 44A is a schematic front view illustrating an example liquid discharging head according to the twenty-first embodiment. FIG. 44B is a schematic side view illustrating an example liquid discharging head according to the twenty-first embodiment. FIG. 44C is a schematic bottom view illustrating an example liquid discharging head according to the twenty-first embodiment. FIG. 44D is a schematic cross-sectional view illustrating a portion near a discharging port of an example liquid discharging head according to the twenty-first embodiment.

As illustrated in FIG. 44A to FIG. 44D, in the twenty-first embodiment, the inner diameter of the liquid retaining unit 5010 is roughly the same as the diameter of the discharging port 5012. This makes it possible to make the liquid retaining unit 5010 even smaller in size.

Figure 45:
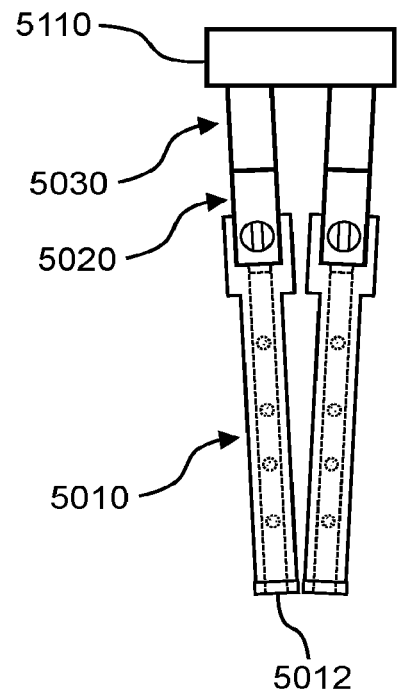
FIG. 45 is a schematic side view illustrating an example of a multichannel in which two liquid discharging heads according to a twenty-first embodiment are disposed adjacently.

FIG. 45 is a schematic side view illustrating an example of a multichannel in which two liquid discharging heads according to the twenty-first embodiment are disposed adjacently.

In the example illustrated in FIG. 45, the liquid discharging heads according to the twenty-first embodiment are disposed in a manner to be inclined toward each other in order to make the distance between the discharging ports 5012 shorter. This can make the pitch between the discharging ports 5012 shorter.

Figure 46:
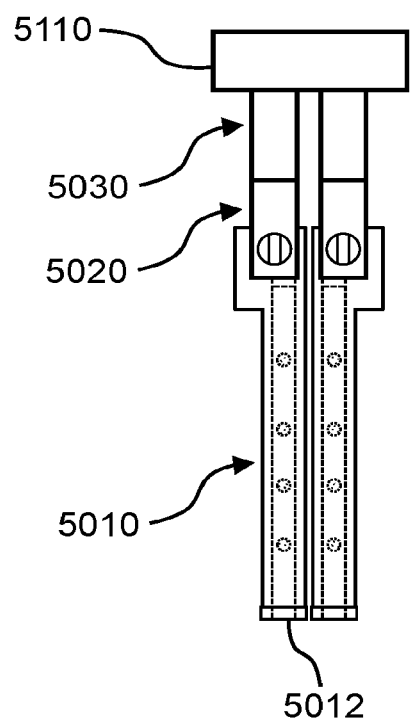
FIG. 46 is a schematic side view illustrating an example of a multichannel in which two modified liquid discharging heads according to a twenty-first embodiment are disposed adjacently.

FIG. 46 is a schematic side view illustrating an example of a multichannel in which modified two liquid discharging heads according to the twenty-first embodiment are disposed adjacently.

By shaping the portion of the liquid retaining unit 5010 coupling to the coupling member 5020 as illustrated in FIG.

46, it is possible to bring the liquid retaining units 5010 closer to each other and make the pitch between the discharging ports 5012 shorter.

Twenty-Second Embodiment

Figure 47A:
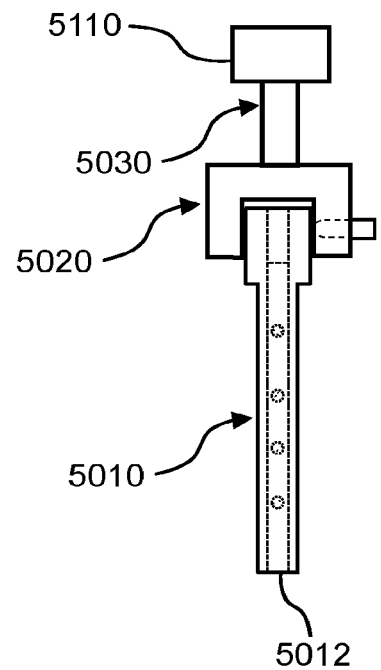
FIG. 47A is a schematic front view illustrating an example liquid discharging head according to a twenty-second embodiment.
Figure 47B:
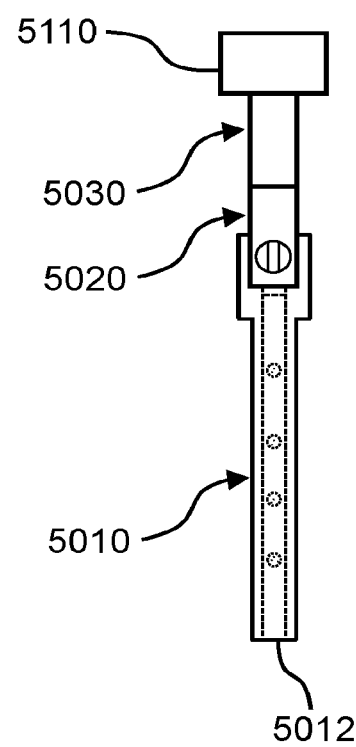
FIG. 47B is a schematic side view illustrating an example liquid discharging head according to a twenty-second embodiment.
Figure 47C:
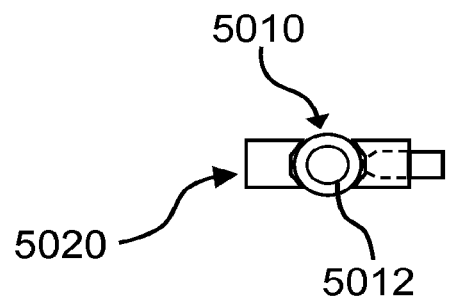
FIG. 47C is a schematic bottom view illustrating an example liquid discharging head according to a twenty-second embodiment.
Figure 47D:
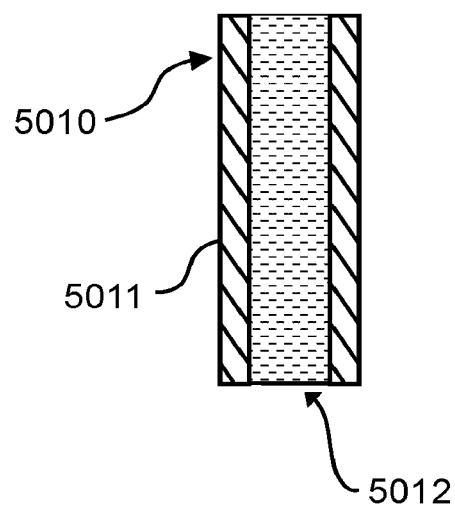
FIG. 47D is a schematic cross-sectional view illustrating an example of a state near a discharging port in an example liquid discharging head according to a twenty-second embodiment.
Figure 47E:
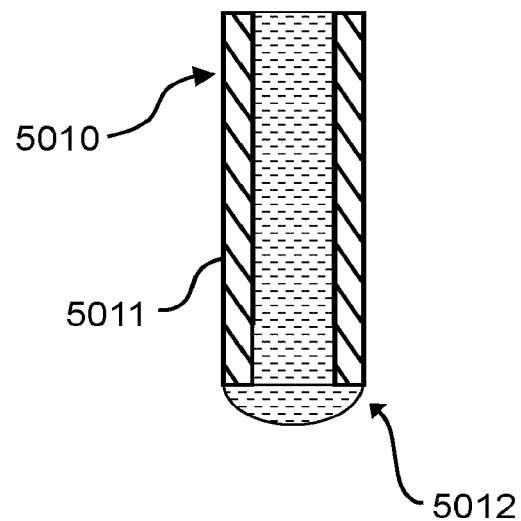
FIG. 47E is a schematic cross-sectional view illustrating another example of a state near a discharging port in an example liquid discharging head according to a twenty-second embodiment.

FIG. 47A is a schematic front view illustrating an example liquid discharging head according to the twenty-second embodiment. FIG. 47B is a schematic side view illustrating an example liquid discharging head according to the twenty-second embodiment. FIG. 47C is a schematic bottom view illustrating an example liquid discharging head according to the twenty-second embodiment. FIG. 47D is a schematic cross-sectional view illustrating an example of a state near a discharging port in an example liquid discharging head according to the twenty-second embodiment. FIG. 47E is a schematic cross-sectional view illustrating another example of a state near a discharging port in an example liquid discharging head according to the twenty-second embodiment.

As illustrated in FIG. 47A to FIG. 47E, when the inner diameter of the liquid retaining unit 5010 is sufficiently small, the liquid discharging head needs not include the membranous member 5013.

When the inner diameter of the liquid retaining unit 5010 (the diameter of the discharging port 5012) is in the range described above, there is no need to suppress the wetting/spreading range of the liquid by means of a membranous member 5013 having water repellency, but it is possible to suppress wetting/spreading of the liquid by a physical limitation as illustrated in FIG. 47D and FIG. 47E.

In the twenty-second embodiment, it is possible to more simplify the structure of the liquid discharging head because there is no need for the membranous member 5013.

Twenty-Third Embodiment

Figure 48A:
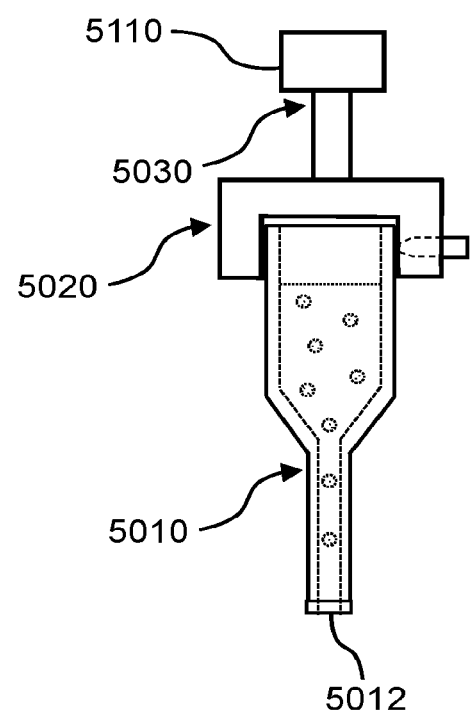
FIG. 48A is a schematic front view illustrating an example liquid discharging head according to a twenty-third embodiment.
Figure 48B:
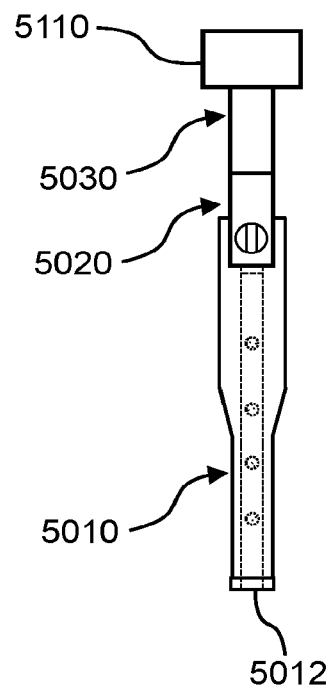
FIG. 48B is a schematic side view illustrating an example liquid discharging head according to a twenty-third embodiment.
Figure 48C:
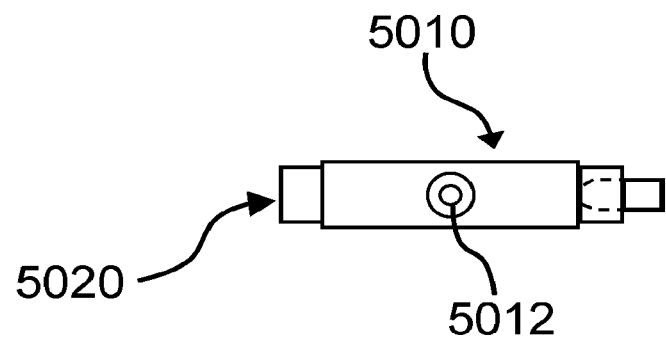
FIG. 48C is a schematic bottom view illustrating an example liquid discharging head according to a twenty-third embodiment.

FIG. 48A is a schematic front view illustrating an example liquid discharging head according to the twenty-third embodiment. FIG. 48B is a schematic side view illustrating an example liquid discharging head according to the twenty-third embodiment. FIG. 48C is a schematic bottom view illustrating an example liquid discharging head according to the twenty-third embodiment.

In the twenty-third embodiment, the liquid retaining unit 5010 includes a membranous member 5013, and the planar shape of the liquid discharging unit 5010 is a rectangular shape as illustrated in FIG. 48C.

As illustrated in FIG. 48A to FIG. 48C, in the twenty-third embodiment, the inner diameter of the liquid retaining unit 5010 increases from the opening of the liquid retaining unit 5010 functioning as the discharging port 5012 toward the opening of the liquid retaining unit 5010 at the opposite side. In this way, in the twenty-third embodiment, it is possible to suppress the diameter at the discharging port 5012 side and make the liquid retaining unit 5010 capable of retaining the liquid in a high amount. This makes it possible to make the liquid retaining unit 5010 retain the liquid in a high amount without making the liquid discharging head large in size, making it possible to reduce the number of times of supplying the liquid into the liquid discharging head and discharge more liquid droplets in a shorter time.

Twenty-Fourth Embodiment

Figure 49:
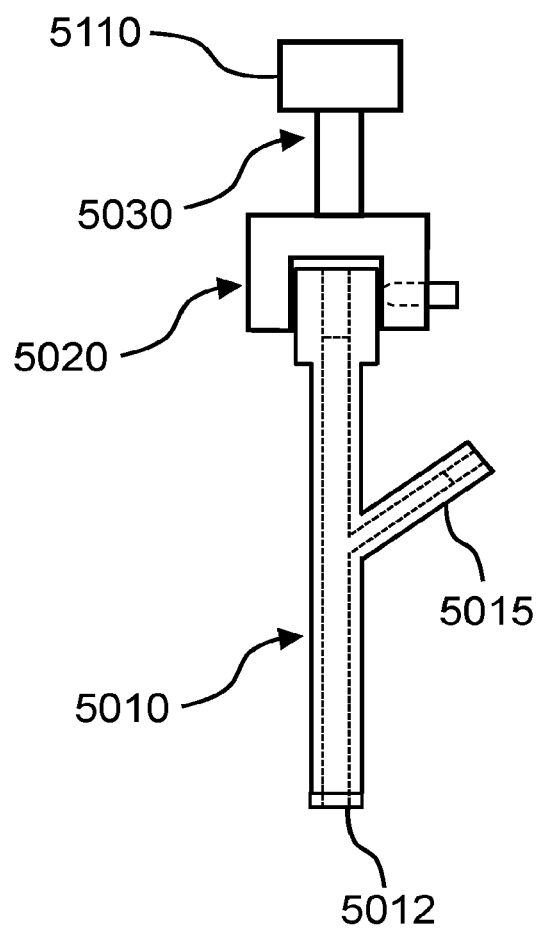
FIG. 49 is a schematic front view illustrating an example liquid discharging head according to a twenty-fourth embodiment.

FIG. 49 is a schematic front view illustrating an example liquid discharging head according to the twenty-fourth embodiment.

As illustrated in FIG. 49, in the twenty-fourth embodiment, the liquid retaining unit 5010 has a branched structure 5015 and can discharge a plurality of kinds of liquids after mixing the liquids in the liquid retaining unit. More specifically, in the twenty-fourth embodiment, different kinds of liquids can be retained in the flow paths constituting the branched structure 5015 of the liquid retaining unit 5010, and the liquids can be mixed at an immediate upstream of the discharging port as a mixture liquid, which can be discharged through the discharging port. In this way, in the twenty-fourth embodiment, by mixing and discharging liquids that are chemically reactive with each other, it is possible to discharge the liquids while allowing the liquids to undergo a chemical reaction.

In this way, in the nineteenth to twenty-first embodiments and the twenty-third and twenty-fourth embodiments, the piezoelectric element 5030 as an example of the displacement member is disposed at the side at which the liquid to be discharged through the discharging port (nozzle) 5012 is provided. This may be an example of the first aspect described above. Further, there is provided the coupling member 5020 configured to couple the membranous member 5013 and the displacement member 5030 to each other in a manner that the membranous member 5013 is mountable and demountable via the liquid retaining unit 5010. This may be an example of the third aspect described above. Furthermore, in the nineteenth to twenty-first embodiments and the twenty-third and twenty-fourth embodiments, there are provided the liquid retaining unit 5010 including the discharging port 5012 through which a liquid is discharged, and the piezoelectric element 5030 as an example of the displacement member configured to displace the position of the liquid retaining unit 5010 to cause the liquid to be discharged through the discharging port 5012. This may be an example of the fourth aspect described above.

In the twenty-second embodiment, there are provided the liquid retaining unit 5010 including the discharging port 5012 through which a liquid is discharged, and a piezoelectric element 5030 as an example of the displacement member configured to displace the position of the liquid retaining unit 5010 to cause the liquid to be discharged through the discharging port 5012. This may be an example of the fourth embodiment described above.

As described above, the liquid discharging head of the present disclosure including the first to fourth aspects can discharge a liquid with a simple structure.

Aspects of the present disclosure are, for example, as follows.

<1> A liquid discharging head including:

a membranous member including a discharging port through which a liquid is discharged; and a displacement member disposed at membranous member's one side at which the liquid to be discharged through the discharging port is provided and configured to displace a position of the membranous member to cause the liquid to be discharged through the discharging port.

<2> The liquid discharging head according to <1>, wherein the displacement member contacts the membranous member.

<3> The liquid discharging head according to <1> or <2>, wherein the displacement member is disposed in a manner to surround a perimeter of the membranous member to be capable of retaining the liquid to be provided on the membranous member.

<4> The liquid discharging head according to any one of <1> to <3>,
wherein at least part of a surface of the displacement member has a coating film to shield contact with the liquid.
<5> The liquid discharging head according to any one of <1> to <4>, further including
a securing member disposed at the membranous member's one side at which the liquid is provided and configured to secure a side of the displacement member opposite to a side of the displacement member contacting the membranous member.
<6> The liquid discharging head according to any one of <3> to <5>, further including
a liquid containing chamber that can contain the liquid to be provided on the displacement member.
<7> The liquid discharging head according to <6>, further including
an electrode that is provided outside the liquid containing chamber and through which a voltage is applied to the displacement member.
<8> The liquid discharging head according to <6> or <7>, further including
a cover disposed at the membranous member's one side at which the liquid is provided in a manner to face the membranous member.
<9> The liquid discharging head according to <1>, further including:
a liquid containing chamber that can contain the liquid to be provided on the membranous member; and
a coupling member configured to couple the liquid containing chamber and the displacement member to each other.
<10> The liquid discharging head according to <9>,
wherein the liquid containing chamber includes an opening.
<11> The liquid discharging head according to <9> or <10>,
wherein the coupling member couples the liquid containing chamber in a manner that the liquid containing chamber is mountable and demountable.
<12> The liquid discharging head according to any one of <9> to <11>,
wherein the membranous member includes a plurality of membranous members and the coupling member couples the membranous member in a manner that the membranous members can be disposed adjacently.
<13> A liquid discharging head including:
a membranous member including a discharging port through which a liquid is discharged; and
a displacement member coupled to at least a part of a perimeter of the membranous member and configured to displace a position of the membranous member to cause the liquid to be discharged through the discharging port,
wherein the membranous member does not deform while the displacement member is displacing the position of the membranous member.
<14> The liquid discharging head according to <13>,
wherein the displacement member is disposed at membranous member's one side at which the liquid is provided.
<15> A liquid discharging head including:
a membranous member including a discharging port through which a liquid is discharged;
a displacement member configured to displace a position of the membranous member to cause the liquid to be discharged through the discharging port; and
a coupling member configured to couple the membranous member and the displacement member to each other in a manner that the membranous member is mountable and demountable.
<16> The liquid discharging head according to <15>, further including
a liquid containing chamber that can contain the liquid to be provided on the membranous member.
<17> A liquid discharging head including:
a liquid retaining unit including a discharging port through which a liquid is discharged; and
a displacement member configured to displace a position of the liquid retaining unit to cause the liquid to be discharged through the discharging port.
<18> The liquid discharging head according to <17>,
wherein the displacement member displaces the position of the liquid retaining unit by reciprocating the liquid retaining unit in a direction approximately parallel with a direction in which the liquid is discharged through the discharging port.
<19> The liquid discharging head according to any one of <1> to <18>,
wherein the liquid to be discharged through the discharging port contains particles.
<20> A liquid discharging apparatus including
the liquid discharging head according to any one of <1> to <19>.

The liquid discharging head according to any one of <1> to <19> and the liquid discharging apparatus according to <20> can solve the various problems in the related art and achieve the object of the present disclosure.

What is claimed is:

1. A liquid discharging head, comprising:
   a membranous member that comprises a discharging port through which a liquid is discharged;
   a liquid containing chamber to contain the liquid to be provided to the membranous member, the liquid containing chamber having an atmospherically exposed portion; and
   a displacement member disposed at a side of the membranous member at which the liquid to be discharged through the discharging port is provided, and configured to displace a position of the membranous member to cause the liquid to be discharged through the discharging port.

2. The liquid discharging head according to claim 1, wherein the displacement member contacts the membranous member.

3. The liquid discharging head according to claim 1, wherein the displacement member is disposed in a manner to surround a perimeter of the membranous member and is configured to retain the liquid to be provided on the membranous member.

4. The liquid discharging head according to claim 1, wherein at least part of a surface of the displacement member has a coating film to shield contact with the liquid.

5. The liquid discharging head according to claim 1, further comprising:
   a securing member disposed at the side of the membranous member at which the liquid is provided, and configured to secure a side of the displacement member opposite to a side of the displacement member contacting the membranous member.

6. The liquid discharging head according to claim 3, further comprising an electrode provided outside the liquid containing chamber and through which a voltage is applied to the displacement member.

7. The liquid discharging head according to claim 3, further comprising a cover disposed at the side of the membranous member at which the liquid is provided so as to to face the membranous member.

8. The liquid discharging head according to claim 1, further comprising:
a coupling member configured to couple the liquid containing chamber and the displacement member to each other.

9. The liquid discharging head according to claim 8, wherein the liquid containing chamber comprises an opening.

10. The liquid discharging head according to claim 8, wherein the coupling member couples the liquid containing chamber in a manner that the liquid containing chamber is mountable and demountable.

11. The liquid discharging head according to claim 8, wherein the membranous member comprises a plurality of membranous members and the coupling member couples the membranous member so that the membranous members can be disposed adjacently.

12. A liquid discharging head, comprising:
a membranous member that comprises a discharging port through which a liquid is discharged; and
a displacement member coupled to at least a part of a perimeter of the membranous member and configured to displace a position of the membranous member to cause the liquid to be discharged through the discharging port,
wherein the displacement member is a piezoelectric element; and
wherein the membranous member does not deform while the displacement member is displacing the position of the membranous member.

13. The liquid discharging head according to claim 12, wherein the displacement member is disposed at a side of the membranous membrane at which the liquid is provided.

14. The liquid discharging head according to claim 1, further comprising a coupling member configured to couple the membranous member and the displacement member to each other in a manner that the membranous member is mountable and demountable.

15. A liquid discharging head, comprising:
a liquid retaining chamber that comprises a discharging port through which a liquid is discharged; and
a displacement member configured to displace a position of the liquid chamber, without deforming the liquid retaining chamber, to cause the liquid to be discharged through the discharging port, wherein the displacement member is a piezoelectric element.

16. The liquid discharging head according to claim 15, wherein the displacement member displaces the position of the liquid retaining chamber by reciprocating the liquid retaining chamber in a direction approximately parallel with a direction in which the liquid is discharged through the discharging port.

17. The liquid discharging head according to claim 1, wherein the liquid to be discharged through the discharging port contains particles.

18. The liquid discharging head according to claim 12, wherein the liquid to be discharged through the discharging port contains particles.

* * * * *